(12) United States Patent
Knox et al.

(10) Patent No.: US 11,479,779 B2
(45) Date of Patent: Oct. 25, 2022

(54) SYSTEMS AND METHODS FOR HIGH-THROUGHPUT AUTOMATED STRAIN GENERATION FOR NON-SPORULATING FUNGI

(71) Applicant: Zymergen Inc., Emeryville, CA (US)

(72) Inventors: Benjamin Knox, Oakland, CA (US); Nasim Mansoori Zangir, San Francisco, CA (US); Ryan Evan Martinez, Oakland, CA (US); Hassan Abdulla, Oakland, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 17/387,634

(22) Filed: Jul. 28, 2021

(65) Prior Publication Data

US 2022/0033831 A1 Feb. 3, 2022

Related U.S. Application Data

(60) Provisional application No. 63/059,577, filed on Jul. 31, 2020.

(51) Int. Cl.
*C12N 15/80* (2006.01)
*C12N 15/10* (2006.01)

(52) U.S. Cl.
CPC ......... *C12N 15/80* (2013.01); *C12N 15/1034* (2013.01)

(58) Field of Classification Search
None
See application file for complete search history.

(56) References Cited

U.S. PATENT DOCUMENTS

| | | | |
|---|---|---|---|
| 4,935,349 A | 6/1990 | Mcknight et al. |
| 5,198,345 A | 3/1993 | Gwynne et al. |
| 5,252,726 A | 10/1993 | Woldike |
| 5,516,670 A | 5/1996 | Kuehnle et al. |
| 5,578,463 A | 11/1996 | Berke et al. |
| 5,605,793 A | 2/1997 | Stemmer |
| 5,705,358 A | 1/1998 | Gouka et al. |
| 5,741,665 A | 4/1998 | Kato et al. |
| 5,753,477 A | 5/1998 | Chan |
| 5,837,458 A | 11/1998 | Minshull et al. |
| 5,876,988 A | 3/1999 | Selten et al. |
| 5,965,384 A | 10/1999 | Boel et al. |
| 6,040,439 A | 3/2000 | Hayakawa |
| 8,871,493 B2 | 10/2014 | Emalfarb et al. |
| 9,574,199 B2 | 2/2017 | Udagawa |
| 9,744,533 B2 | 8/2017 | Breinlinger et al. |
| 9,815,056 B2 | 11/2017 | Wu et al. |
| 9,857,333 B2 | 1/2018 | Chapman et al. |
| 9,889,445 B2 | 2/2018 | Chapman et al. |
| 9,895,699 B2 | 2/2018 | Short et al. |
| 9,908,115 B2 | 3/2018 | Hobbs et al. |
| 9,988,624 B2 | 6/2018 | Serber et al. |
| 9,996,920 B2 | 6/2018 | Du et al. |
| 10,010,882 B2 | 7/2018 | White et al. |
| 10,047,358 B1 | 8/2018 | Serber et al. |
| 10,058,865 B2 | 8/2018 | Breinlinger et al. |
| 10,101,250 B2 | 10/2018 | White et al. |
| 10,239,058 B2 | 3/2019 | Lavieu et al. |
| D844,471 S | 4/2019 | Stone et al. |
| 10,245,588 B2 | 4/2019 | Khandros et al. |
| 10,252,907 B2 | 4/2019 | Breinlinger et al. |
| 10,336,998 B2 | 7/2019 | Serber et al. |
| 10,350,594 B2 | 7/2019 | Hobbs et al. |
| 10,351,861 B2 | 7/2019 | Olsen |
| 10,384,204 B2 | 8/2019 | Mcfarland et al. |
| 10,407,658 B2 | 9/2019 | Newstrom et al. |
| 10,457,933 B2 | 10/2019 | Serber et al. |
| 10,569,271 B2 | 2/2020 | Wu et al. |
| 10,578,630 B2 | 3/2020 | Du |
| 10,646,871 B2 | 5/2020 | White et al. |
| D887,296 S | 6/2020 | Stone et al. |
| 10,675,625 B2 | 6/2020 | Lionberger et al. |
| 10,690,628 B2 | 6/2020 | Chapman et al. |
| 10,705,082 B2 | 7/2020 | Beaumont et al. |
| 10,712,344 B2 | 7/2020 | Chapman et al. |
| 10,723,988 B2 | 7/2020 | Lowe, Jr. et al. |
| 10,751,715 B1 | 8/2020 | Guan et al. |
| 10,954,511 B2 | 3/2021 | SunSpiral et al. |
| 10,973,227 B2 | 4/2021 | White et al. |

(Continued)

FOREIGN PATENT DOCUMENTS

| | | |
|---|---|---|
| EP | 0238023 A2 | 9/1987 |
| EP | 0635574 B1 | 4/2003 |

(Continued)

OTHER PUBLICATIONS

Diaz et al., Genetic Transformation of the Filamentous Fungus *Pseudogymnoascus verrucosus* of Antarctic Origin. Frontiers in Microbiology (2019) 10:2675, 1-10 (Year: 2019).*
U.S. Appl. No. 17/207,376, filed Mar. 19, 2021, SunSpiral, et al.
U.S. Appl. No. 17/387,634, filed Jul. 28, 2021, Knox, et al.
Aoyama, et al., "Spy1, a Histidine-Containing Phosphotransfer Signaling Protein, Regulates the Fission Yeast Cell Cycle through the Mcs4 Response Regulator." Journal of Bacteriology (Sep. 2000); 182(17): 4868-4874.
Arentshorst, et al., "Efficient Generation of Aspergillus niger Knock Out Strains by Combining NHEJ Mutants and a Split Marker Approach". In: van den Berg M., Maruthachalam K. (eds) Genetic Transformation Systems in Fungi (2014), vol. 1. Fungal Biology, pp. 263-272, 10 pages.

(Continued)

*Primary Examiner* — Neil P Hammell
*Assistant Examiner* — Catherine Konopka
(74) *Attorney, Agent, or Firm* — Cooley LLP

(57) ABSTRACT

Embodiments disclosed include systems and methods to generate and/or improve non-sporulating filamentous fungal cells using high-throughput techniques. Embodiments disclosed also include systems and methods for evaluation and iterative adjustment of methods to generate and/or isolate and select desired strains of non-sporulating filamentous fungal cells using high-throughput techniques.

30 Claims, 16 Drawing Sheets

(56) References Cited

U.S. PATENT DOCUMENTS

| | | |
|---|---|---|
| 11,007,520 B2 | 5/2021 | Lowe, Jr. et al. |
| 11,028,401 B2 | 6/2021 | Bruno et al. |
| 11,151,497 B2 | 10/2021 | Frewen et al. |
| 11,180,753 B2 | 11/2021 | Sunspiral et al. |
| 11,242,524 B2 | 2/2022 | Sunspiral et al. |
| 11,299,741 B2 | 4/2022 | Bruno et al. |
| 2009/0280529 A1 | 11/2009 | Berg et al. |
| 2009/0317798 A1 | 12/2009 | Heid et al. |
| 2010/0216648 A1 | 8/2010 | Staehler et al. |
| 2011/0272127 A1 | 7/2011 | Jacobson et al. |
| 2011/0223671 A1 | 9/2011 | Yoder et al. |
| 2013/0149742 A1 | 6/2013 | Bower et al. |
| 2013/0319861 A1 | 12/2013 | Khandros et al. |
| 2014/0017791 A1 | 1/2014 | Chapman et al. |
| 2014/0116881 A1 | 5/2014 | Chapman et al. |
| 2014/0120558 A1 | 5/2014 | Chapman |
| 2014/0124370 A1 | 5/2014 | Short et al. |
| 2014/0220689 A1 | 8/2014 | Bodie et al. |
| 2015/0111784 A1 | 4/2015 | Chapman |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0166326 A1 | 6/2015 | Chapman et al. |
| 2015/0211013 A1 | 7/2015 | Emalfarb et al. |
| 2015/0306598 A1 | 10/2015 | Khandros et al. |
| 2015/0306599 A1 | 10/2015 | Khandros et al. |
| 2015/0352547 A1 | 12/2015 | Breinlinger et al. |
| 2016/0158748 A1 | 6/2016 | Wu et al. |
| 2016/0158757 A1 | 6/2016 | Breinlinger et al. |
| 2016/0160259 A1 | 6/2016 | Du |
| 2016/0171686 A1 | 6/2016 | Du et al. |
| 2016/0184821 A1 | 6/2016 | Hobbs et al. |
| 2016/0193604 A1 | 7/2016 | Mcfarland et al. |
| 2016/0199837 A1 | 7/2016 | Breinlinger et al. |
| 2016/0257918 A1 | 9/2016 | Chapman et al. |
| 2016/0304905 A1 | 10/2016 | Hansen et al. |
| 2016/0312165 A1 | 10/2016 | Lowe, Jr. et al. |
| 2016/0318038 A1 | 11/2016 | Short et al. |
| 2016/0338347 A1 | 11/2016 | White et al. |
| 2016/0340632 A1 | 11/2016 | Breinlinger et al. |
| 2016/0370266 A1 | 12/2016 | White et al. |
| 2017/0021366 A1 | 1/2017 | Chapman et al. |
| 2017/0043343 A1 | 2/2017 | Khandros et al. |
| 2017/0113231 A9 | 4/2017 | Breinlinger et al. |
| 2017/0114316 A1 | 4/2017 | Newstrom et al. |
| 2017/0159045 A1 | 6/2017 | Serber et al. |
| 2017/0165667 A1 | 6/2017 | Beaumont et al. |
| 2017/0173580 A1 | 6/2017 | Lowe, Jr. et al. |
| 2017/0184583 A1 | 6/2017 | Beaumont et al. |
| 2017/0224734 A1 | 8/2017 | Chapman et al. |
| 2017/0276679 A1 | 9/2017 | Chapman et al. |
| 2017/0316353 A1 | 11/2017 | Frewen et al. |
| 2017/0354969 A1 | 12/2017 | Lionberger et al. |
| 2017/0355595 A1 | 12/2017 | Breinlinger et al. |
| 2018/0037919 A1 | 2/2018 | Bodie et al. |
| 2018/0099282 A1 | 4/2018 | Breinlinger et al. |
| 2018/0126380 A1 | 5/2018 | Khandros et al. |
| 2018/0135011 A1 | 5/2018 | Bronevetsky et al. |
| 2018/0147576 A1 | 5/2018 | Lavieu et al. |
| 2018/0193835 A1 | 7/2018 | Hobbs et al. |
| 2018/0259482 A1 | 9/2018 | Chapman et al. |
| 2018/0272350 A1 | 9/2018 | Chapman et al. |
| 2018/0298318 A1 | 10/2018 | Kurz et al. |
| 2018/0362991 A1 | 12/2018 | Serber et al. |
| 2019/0060900 A1 | 2/2019 | Breinlinger et al. |
| 2019/0060907 A1 | 2/2019 | Bao et al. |
| 2019/0064038 A1 | 2/2019 | White et al. |
| 2019/0083983 A1 | 3/2019 | Breinlinger et al. |
| 2019/0085375 A1 | 3/2019 | Mcewen |
| 2019/0134630 A1 | 5/2019 | White |
| 2019/0152771 A1 | 5/2019 | Breinlinger et al. |
| 2019/0172196 A1 | 6/2019 | Du et al. |
| 2019/0194692 A1 | 6/2019 | Meijrink et al. |
| 2019/0217297 A1 | 7/2019 | Lavieu et al. |
| 2019/0240665 A1 | 8/2019 | Lionberger et al. |
| 2019/0275516 A1 | 9/2019 | Lowe, Jr. et al. |
| 2019/0283026 A1 | 9/2019 | Loutherback et al. |
| 2019/0323036 A1 | 10/2019 | Bruno et al. |
| 2019/0345488 A1 | 11/2019 | Soumillon et al. |
| 2019/0374944 A1 | 12/2019 | Lundquist et al. |
| 2019/0376070 A1 | 12/2019 | Bruno et al. |
| 2019/0384963 A1 | 12/2019 | Kim et al. |
| 2020/0017817 A1 | 1/2020 | Kelly-greene et al. |
| 2020/0032193 A1 | 1/2020 | Newstrom et al. |
| 2020/0038857 A1 | 2/2020 | Mcfarland et al. |
| 2020/0064337 A1 | 2/2020 | Park et al. |
| 2020/0071693 A1 | 3/2020 | SunSpiral et al. |
| 2020/0078785 A1 | 3/2020 | Hobbs et al. |
| 2020/0078788 A1 | 3/2020 | Chapman et al. |
| 2020/0115680 A1 | 4/2020 | Bronevetsky et al. |
| 2020/0123491 A1 | 4/2020 | Beemiller et al. |
| 2020/0123535 A1 | 4/2020 | SunSpiral et al. |
| 2020/0139362 A1 | 5/2020 | Beemiller et al. |
| 2020/0171501 A1 | 6/2020 | Mcewen et al. |
| 2020/0230601 A1 | 7/2020 | White et al. |
| 2021/0102150 A1 | 4/2021 | Kurz et al. |
| 2021/0114020 A1 | 4/2021 | Lowe, Jr. et al. |
| 2021/0115436 A1 | 4/2021 | Ramenani et al. |
| 2021/0129142 A1 | 5/2021 | Hobbs et al. |
| 2021/0254080 A1 | 8/2021 | Bruno et al. |
| 2021/0284993 A1 | 9/2021 | SunSpiral et al. |
| 2022/0145288 A1 | 5/2022 | Sunspiral et al. |

FOREIGN PATENT DOCUMENTS

| | | |
|---|---|---|
| JP | H11304666 A | 11/1999 |
| JP | 2012504390 A | 2/2012 |
| JP | 2013017408 A | 1/2013 |
| JP | 2013533737 A | 8/2013 |
| WO | WO 1993/007277 A1 | 4/1993 |
| WO | WO 1993/025663 A1 | 12/1993 |
| WO | WO 1997/006261 A2 | 2/1997 |
| WO | WO 1997/008332 A1 | 3/1997 |
| WO | WO 2000/020555 A2 | 4/2000 |
| WO | WO 2005/021772 A1 | 3/2005 |
| WO | WO 2005/095624 A2 | 10/2005 |
| WO | WO 2008/113847 A2 | 9/2008 |
| WO | WO 2009/085135 A2 | 7/2009 |
| WO | WO-2010039889 A2 | 4/2010 |
| WO | WO 2011/154147 A1 | 12/2011 |
| WO | WO-2012142591 A2 | 10/2012 |
| WO | WO 2013/135729 A1 | 9/2013 |
| WO | WO 2015/082535 A1 | 6/2015 |
| WO | WO 2015/168184 A1 | 11/2015 |
| WO | WO 2016/073990 A2 | 5/2016 |
| WO | WO 2016/100272 A1 | 6/2016 |
| WO | WO 2016/100568 A1 | 6/2016 |
| WO | WO 2016/100571 A1 | 6/2016 |
| WO | WO 2017/100376 A2 | 6/2017 |
| WO | WO 2017/100377 A1 | 6/2017 |
| WO | WO 2017/189784 A1 | 11/2017 |
| WO | WO 2018/126207 A1 | 12/2017 |
| WO | WO 2018/009372 A1 | 1/2018 |
| WO | WO 2018/050666 A1 | 3/2018 |
| WO | WO 2018/226900 A2 | 6/2018 |
| WO | WO 2018/123134 A1 | 7/2018 |
| WO | WO 2019/236848 A1 | 12/2019 |
| WO | WO 2021/081432 A1 | 4/2021 |
| WO | WO 2021/097449 A1 | 5/2021 |
| WO | WO-2022026709 A1 | 2/2022 |

OTHER PUBLICATIONS

Arras and Fraser, "Chemical Inhibitors of Non-Homologous End Joining Increase Targeted Construct Integration in Cryptococcus neoformans". PLoS One (Sep. 2016); 11(9): e0163049.

Aslanidis, et al., "Ligation-independent cloning of PCR products (LIC-PCR)." Nucleic Acids Research 18.20 (1990): 6069-6074.

Azhayev, et al., "Amide group assisted 3'-dephosphorylation of oligonucleotides synthesized on universal A-supports." Tetrahedron 57.23 (2001): 4977-4986.

(56) References Cited

OTHER PUBLICATIONS

Barcellos, et al. "Genetic analysis of Aspergillus nidulans unstable transformants obtained by the biolistic process." Canadian Journal of Microbiology (1998); 44(12): 1137-1141.
Basu, et al., "Purification of specific cell population by fluorescence activated cell sorting (FACS)". J Vis Exp. (2010); (41):1546. Published Jul. 10, 2010.
Becker and Guarente, "[12] High-efficiency transformation of yeast by electroporation." Methods in Enzymology (1991); 194: 182-187.
Bégueret, et al., "Cloning gene ura5 for the orotidylic acid pyrophosphorylase of the filamentous fungus Podospora anserina: transformation of protoplasts". Gene (Dec. 1984); 32(3): 487-492.
Beydon, et al., "Microbiological High Throughput Screening: An Opportunity for the Lead Discovery Process". Journal of Biomolecular Screening (2000); 5(1): 13-22.
Bischof, et al., "A versatile platform for creating a comprehensive UAS-ORFeome library in Drosophila", Development (Jun. 2013); 140(11): 2434-2442. Epub May 1, 2013.
Blumhoff, et al., "Targeting enzymes to the right compartment: metabolic engineering for itaconic acid production by Aspergillus niger". Metab Eng. (2013); 19: 26-32.
Brown, et al., "Yeast Skn7p functions in a eukaryotic two-component regulatory pathway." The EMBO Journal (1994); 13(21): 5186-5194.
Casqueiro, et al., "Gene Targeting in Penicillium chrysogenum: Disruption of the lys2 Gene Leads to Penicillin Overproduction". Journal of Bacteriology (Feb. 1999); 181(4): 1181-1188.
Catlett, et al., "Split-Marker Recombination for Efficient Targeted Deletion of Fungal Genes". Fungal Genetics Reports (2003); 50(Article 4): 9-11.
Chakraborty and Kapoor, "Transformation of filamentous fungi by electroporation." Nucleic Acids Research (1990); 18(22): 6737.
Cheng and Bélanger, "Protoplast preparation and regeneration from spores of the biocontrol fungus Pseudozyma flocculosa". FEMS Microbiology Letters (Sep. 2000); 190(2): 287-291.
Choi, et al., "Single spore isolation of fungi". Fungal Diversity (Oct. 1999); 3: 29-38.
Christiansen, et al., "Biolistic transformation of the obligate plant pathogenic fungus, Erysiphe graminis f. sp. hordei." Current Genetics (1995); 29(1): 100-102.
Christie and Gordon, "The Agrobacterium Ti plasmids." Microbiology Spectrum (2014); 2(6): 10.1128.
Collado, et al., "High-throughput culturing of fungi from plant litter by a dilution-to-extinction technique". FEMS Microbiol Ecol. (2007); 60(3): 521-533.
Crameri, et al. "DNA shuffling of a family of genes from diverse species accelerates directed evolution." Nature (1998); 391(6664): 288-291.
Crameri, et al. "Molecular evolution of an arsenate detoxification pathway by DNA shuffling." Nature Biotechnology (1997); 15(5): 436-438.
Czar, et al. "Gene synthesis demystified" Trends in biotechnology 27.2 (2009): 63-72.
Dai, et al., "Identification of Genes Associated with Morphology in Aspergillus niger by Using Suppression Subtractive Hybridization". Applied and Environmental Microbiology (Apr. 2004); 70(4): 2474-2485.
Dai, et al., "Impact of alg3 gene deletion on growth, development, pigment production, protein secretion, and functions of recombinant Trichoderma reesei cellobiohydrolases in Aspergillus niger". Fungal Genetics and Biology (Dec. 2013); 61:120-132. Epub Sep. 25, 2013.
Damha, et al., "An improved procedure for derivatization of controlled-pore glass beads for solid-phase oligonucleotide synthesis." Nucleic Acids Research 18.13 (1990): 3813-3821.
De Almeida, et al. "Transgenic expression of two marker genes under the control of an Arabidopsis rbcS promoter: Sequences encoding the Rubisco transit peptide increase expression levels." Molecular and General Genetics MGG (1989); 218(1): 78-86.
De Boer, et al., "Highly efficient gene targeting in Penicillium chrysogenum using the bi-partite approach in Δlig4 or Δku70 mutants". Fungal Genet Biol. (Oct. 2010); 47(10): 839-846. Epub Jul. 24, 2010.
Durand, et al. "Transient expression of the β-glucuronidase gene after biolistic transformation of the anaerobic fungus Neocallimastix frontalis." Current Genetics (1997); 31(2): 158-161.
Engler, et al., "A one pot, one step, precision cloning method with high throughput capability." PLoS One 3.11 (2008): e3647.
Extended European Search Report for European Patent Application No. EP 17886439.3, dated Jul. 3, 2020, 12 pages.
Eyini, et al., "Isolation, Regeneration and PEG-Induced Fusion of Protoplasts of Pleurotus pulmonarius and Pleurotus florida." Mycobiology (Jun. 2006); 34(2): 73-78.
Farrow and Arnold, "High Throughput Screening of Fungal Endoglucanase Activity in Escherichia coli". J. Vis. Exp. (54), e2942. Epub Aug. 13, 2011.
Fincham, J.R., "Transformation in fungi." Microbiological Reviews (Mar. 1989); 53(1): 148-170.
Gibson, et al., "Enzymatic assembly of DNA molecules up to several hundred kilobases." Nature Methods 6.5 (2009): 343-345.
Goosen, et al., "Transformation of Aspergillus niger using the homologous orotidine-5'-phosphate-decarboxylase gene". Current Genetics (Mar. 1987); 11(6-7): 499-503.
Hagiwara, et al., "Characterization of NikA histidine kinase and two response regulators with special reference to osmotic adaptation and asexual development in Aspergillus nidulans". Bioscience, Biotechnology, and Biochemistry (Jul. 23, 2009); 73(7): 1566-1571.
Ho and Ko, "A simple method for obtaining single-spore isolates of fungi", Bot. Bull. Acad. Sin. (1997); 38(1): 41-43.
Huang, et al., "Microfluidic screening and whole-genome sequencing identifies mutations associated with improved protein secretion by yeast". PNAS (Aug. 25, 2015); 112 (34): E4689-E4696. Epub Aug. 10, 2015.
Hynes, M.J., "Genetic transformation of filamentous fungi". J. Genet. (Dec. 1996); 75(3): 297-311.
Ito, et al., "Transformation of intact yeast cells treated with alkali cations." Journal of Bacteriology (1983); 153(1): 163-168.
Ji, et al., "Iterative combinatorial mutagenesis as an effective strategy for generation of deacetoxycephalosporin C synthase with improved activity toward penicillin". G. Appl Environ Microbiol. (2012); 78(21): 7809-7812.
Jiang, et al., "Molecular tools for functional genomics in filamentous fungi: Recent advances and new strategies". Biotechnol Adv. (Dec. 2013); 31(8): 1562-1574. Epub Aug. 26, 2013.
Jones, et al., "High level expression of introduced chimaeric genes in regenerated transformed plants." The EMBO Journal (1985); 4(10): 2411-2418.
Khanna, N.C., et al. "Identification of the template binding polypeptide in the pea chloroplast transcriptional complex." Nucleic Acids Research (1992); 20.1: 69-74.
Kotera, et al., "A high-throughput and single-tube recombination of crude PCR products using a DNA polymerase inhibitor and type IIS restriction enzyme." Journal of Biotechnology 137.1-4 (2008): 1-7.
Kozlov, et al., "Significant improvement of quality for long oligonucleotides by using controlled pore glass with large pores." Nucleosides, Nucleotides and Nucleic Acids 24.5-7 (2005): 1037-1041.
Krijgsheld, et al., "Development in Aspergillus". Studies in Mycology (Mar. 2013); 74: 1-29. Epub Sep. 12, 2012.
Li, et al., "Methods for genetic transformation of filamentous fungi". Microb Cell Fact. (Oct. 3, 2017); 16(1): 168, pp. 1-13.
Li, et al., "The yeast histidine protein kinase, Sln1p, mediates phosphotransfer to two response regulators, Ssk1p and Skn7p". The EMBO Journal (1998); 17(23): 6952-6962.
Liu, et al., "Efficient genome editing in filamentous fungus Trichoderma reesei using the CRISPR/Cas9 system". Cell Discov (2015); 1, 15007, 11 pages.
Liu, et al., "Improved Production of a Heterologous Amylase in Saccharomyces cerevisiae by Inverse Metabolic Engineering". Appl Environ Microbiol (Sep. 2014); 80(17): 5542-5550. Epub Jun. 27, 2014.

(56) References Cited

OTHER PUBLICATIONS

Loske, et al., "Tandem shock waves to enhance genetic transformation of Aspergillus niger". Ultrasonics (Aug. 2014); 54(6): 1656-1662.
Magaña-Ortíz, et al., "A novel and highly efficient method for genetic transformation of fungi employing shock waves". Fungal Genetics and Biology (Jul. 2013); 56: 9-16.
Moore, et al. "Strategies for the in vitro evolution of protein function: enzyme evolution by random recombination of improved sequences." Journal of Molecular Biology (1997); 272(3): 336-347.
Nakashima, et al., "Bacterial cellular engineering by genome editing and gene silencing." International Journal of Molecular Sciences (2014); 15(2): 2773-2793.
Nakasone, et al., "Preservation and distribution of fungal cultures". Biodiversity of Fungi, G.M. Mueller et al., (ED), (2004), Ch. 3, pp. 37-47, 13 pages.
Nielsen, et al., "Efficient PCR-based gene targeting with a recyclable marker for Aspergillus nidulans". Fungal Genet Biol. (Jan. 2006); 43(1): 54-64. Epub Nov. 11, 2005.
Nielsen, et al., "Transient disruption of non-homologous end-joining facilitates targeted genome manipulations in the filamentous fungus *Aspergillus nidulans*". Fungal Genet Biol. (Mar. 2008); 45(3): 165-170. Epub Jul. 20, 2007.
Nielsen, et al., "Transient Marker System for Iterative Gene Targeting of a Prototrophic Fungus". Appl Environ Microbiol. (Nov. 2007); 73(22): 7240-7245. Epub Oct. 5, 2007.
Nódvig, et al., "A CRISPR-Cas9 System for Genetic Engineering of Filamentous Fungi". PLoS One (Jul. 2015); 10(7): e0133085.
Park, et al., "High-throughput production of gene replacement mutants in Neurospora crassa". Methods Mol Biol. (2011); Ch. 13, 722: 179-189.
PCT/US2017/069086, International Preliminary Report on Patentability, dated Jul. 2, 2019, 10 pages.
PCT/US2017/069086, International Search Report and Written Opinion dated May 14, 2018, 13 pages.
PCT/US2017/069086, Invitation to Pay Additional Fees, dated Mar. 12, 2018, 2 pages.
PCT/US2018/036360, International Preliminary Report on Patentability dated Dec. 10, 2019, 20 pages.
PCT/US2018/036360, International Search Report and Written Opinion dated Nov. 23, 2018, 39 pages.
PCT/US2018/036360, Invitation to Pay Additional Fees, dated Sep. 21, 2018, 28 pages.
PCT/US2019/035793, International Preliminary Report on Patentability dated Dec. 8, 2020, 9 pages.
PCT/US2019/035793, International Search Report and Written Opinion dated Nov. 8, 2019, 16 pages.
PCT/US2019/035793, Invitation to Pay Additional Fees, dated Aug. 22, 2019, 4 pages.
Pohl, et al., "CRISPR/Cas9 Based Genome Editing of Penicillium chrysogenum". ACS Synth Biol. (Jul. 15, 2016); 5(7): 754-764. Epub May 3, 2016.
Reyrat, et al., "Counterselectable markers: untapped tools for bacterial genetics and pathogenesis." Infection and Immunity 66.9 (1998): 4011-4017.
Ricciardelli, et al., "Development and characterization of primary cultures of smooth muscle cells from the fibromuscular stroma of the guinea pig prostate." In Vitro Cellular & Developmental Biology (1989); 25(11): 1016-1024.

Roncero, et al., "Mutagenesis in multinucleate cells: the effects of N-methyl-N'-nitro-N-nitrosoguanidine on phycomyces sporres". Mutation Research/Fundamental and Molecular Mechanisms of Mutagenesis (Feb. 1984); 125(2): 195-204.
Ruiz-Díez, B., "Strategies for the transformation of filamentous fungi". J. Appl. Microbiologogy (Jan. 2002); 92(2): 189-195.
Sierzchala, et al., "Solid-phase oligodeoxynucleotide synthesis: a two-step cycle using peroxy anion deprotection." Journal of the American Chemical Society 125.44 (2003): 13427-1344.
Stemmer, Willem P.C., "DNA shuffling by random fragmentation and reassembly: In vitro recombination for molecular evolution." Proceedings of the National Academy of Sciences (1994); 91(22): 10747-10751.
Stemmer, Willem P.C., "Rapid evolution of a protein in vitro by DNA shuffling." Nature (1994); 370(6488): 389-391.
Szewczyk, et al., "Fusion PCR and gene targeting in Aspergillus nidulans". Nat Protoc. (Jan. 1, 2006); 1(6): 3111-3120.
Tear, et al., "Excision of Unstable Artificial Gene-Specific Inverted Repeats Mediates Scar-Free Gene Deletions in *Escherichia coli*." Applied Biochemistry and Biotechnology (2014); 175(4): 1858-1867.
Tian, et al., "Advancing high-throughput gene synthesis technology." Molecular BioSystems 5.7 (2009): 714-722.
Weber, et al., "Assembly of designer TAL effectors by Golden Gate cloning." PLoS One 6.5 (2011): e19722.
Wyatt, et al., "Essential Roles for Polymerase θ-Mediated End Joining in the Repair of Chromosome Breaks". Molecular Cell (Aug. 2016); 63(4): 662-673.
Yabuki, et al., "Rapid method for converting fungal cells into protoplasts with a high regeneration frequency". Experimental Mycology (Dec. 1984); 8(4): 386-390.
Yelton, et al., "Transformation of Aspergillus nidulans by using a trpC plasmid." Proceedings of the National Academy of Sciences (1984); 81(5): 1470-1474.
Yu, et al., "Double-joint PCR: a PCR-based molecular tool for gene manipulations in filamentous fungi." Fungal Genetics and Biology 41.11 (2004): 973-981.
Zhang, et al., "An Optimized Protocol of Single Spore Isolation for Fungi". Cryptogamie, Mycologie (Dec. 2013); 34(4): 349-356.
Zhang, et al., "Directed evolution of a fucosidase from a galactosidase by DNA shuffling and screening." Proceedings of the National Academy of Sciences (1997); 94 (9): 4504-4509.
PCT/US2021/043704, International Search Report and Written Opinion, dated Dec. 30, 2021, 17 pages.
PCT/US2021/043704, Invitation to Pay Additional Fees, dated Oct. 13, 2021, 2 pages.
U.S. Appl. No. 16/453,260, filed Dec. 29, 2017, US 2019-0323036 A1, Oct. 24, 2019, Pending.
U.S. Appl. No. 16/600,062, filed Jun. 6, 2018, US 2020-0071693 A1, Mar. 5, 2020, U.S. Pat. No. 10,954,511, Mar. 23, 2021, Registered.
U.S. Appl. No. 16/723,594, filed Dec. 20, 2019, US 2020-0123535 A1, Apr. 23, 2020, Pending.
U.S. Appl. No. 17/207,376, filed Mar. 19, 2021, Pending.
U.S. Appl. No. 16/433,624, filed Jun. 6, 2019, US 2019-0376070 A1, Dec. 12, 2019, U.S. Pat. No. 11,028,401, Jun. 8, 2021, Registered.
U.S. Appl. No. 17/245,928, filed Apr. 30, 2021, US 2021-0254080 A1, Aug. 19, 2021, Pending.
Znidsaric and Pavko, "The Morphology of Filamentous Fungi in Submerged Cultivations as a Bioprocess Parameter". Morphology of Filamentous Fungi, Food technol. biotechnol. (2001); 39(3): 237-252.

* cited by examiner

620

---

Select a set of volumes of liquid suspension including a DNA source sample and a protoplast source associated with a cell, each volume of the liquid suspension being different, by at least one predetermined property, from the remaining volumes of the set of volumes of the liquid suspension.
671

↓

Dispense the set of volumes of the liquid suspension across a plurality of reaction areas, each reaction area from the plurality of reaction areas including a discrete quantity of the liquid suspension 673

↓

Transform the quantity of liquid suspension included in each reaction area from the plurality of reaction areas to generate a transformation output from a set of transformation outputs 675

↓

Evaluate the set of transformation outputs to calculate at least one of (i) a number of transformation outputs that included a successful transformant, and (ii) a number of transformation outputs that include a desired number of transformants 677

Dispense discrete volumes of a liquid suspension, obtained from a reaction area from a plurality of reaction areas in a first substrate, to a series of growth areas from a plurality of series of growth areas distributed across a plurality of second substrates, the plurality of reaction areas including a set of transformants, the dispensing configured to generate a set of growth outputs including colonies derived from the set of transformants. 771

Evaluate the set of growth outputs to calculate at least one of (i) a number of growth outputs that included growth of colonies derived from a successful transformant, and (ii) a number of growth outputs that included colonies derived from a single clonal transformant. 772

FIG. 7

SYSTEMS AND METHODS FOR HIGH-THROUGHPUT AUTOMATED STRAIN GENERATION FOR NON-SPORULATING FUNGI

CROSS-REFERENCE TO RELATED APPLICATIONS

This application claims the benefit of priority to U.S. Provisional Application No. 63/059,577, filed on Jul. 31, 2020, entitled "SYSTEMS AND METHODS FOR HIGH-THROUGHPUT AUTOMATED STRAIN GENERATION FOR NON-SPORULATING FUNGI," which is incorporated by reference herein in its entirety for all purposes.

FIELD OF DISCLOSURE

The present disclosure generally relates to systems and methods for automated fungal genomic engineering. The disclosed systems and methods are directed to facilitate high-throughput generation of clonal strains of non-sporulating fungi using liquid media. The resultant fungal production strains are well-suited for growth in sub-merged cultures, e.g., for the large-scale production of products of interest (e.g., antibiotics, metabolites, proteins, etc.) for commercial applications.

BACKGROUND

Eukaryotic cells are preferred organisms for the production of polypeptides and secondary metabolites. Filamentous fungi are capable of expressing native and heterologous proteins to high levels, making them well-suited for the large-scale production of enzymes and other proteins for industrial, pharmaceutical, animal health and food and beverage applications. The use of filamentous fungi for large-scale production of products of interest, however, often requires genetic manipulation of the selected fungi for improving strain performance in industrial applications. Moreover, genetically pure strains are desired to achieve efficient large-scale production of products of interest. Currently available high-throughput methods for genetic engineering of filamentous fungi rely on fungal strains going through sporulation for the isolation of genetically pure strains. It is not uncommon for industrial filamentous fungal strains to have lost the ability to sporulate, or sporulate very poorly, thereby precluding or severely limiting the application of existing high-throughput methods for strain improvement programs. This presents a challenge for adapting these useful strains into scalable high-throughput genetic manipulation workflows. Thus, there is an ongoing and unmet need for methods, systems, and tools for the isolation and large-scale selection of genetically pure clonal strains of non-sporulating fungi using automated and HTP capabilities.

SUMMARY OF THE DISCLOSURE

Embodiments disclosed herein include a method for isolating clonal transformants from a transformation mixture containing homokaryotic and heterokaryotic transformants. The method comprises (a) dispensing a discrete volume of a liquid suspension including a predetermined concentration of a DNA source and a predetermined concentration of a protoplast source to a reaction area in a first substrate. The first substrate includes a plurality of reaction areas. The dispensing is configured to generate, in each reaction area from the plurality of reaction areas, a transformation output in liquid media that is subjected to a one-to-many distribution to a series of growth areas. The dispensing the transformation output is such that a percentage of growth areas, from the series of growth areas, that result in a growth that is derived from the transformation output is below a predetermined threshold value. The method further comprises (b) distributing equal volumes of the transformation output in liquid media from each individual reaction area from the plurality of reaction areas, to the series of growth areas to spatially separate transformants. The series of growth areas are distributed across a plurality of second substrates. The method further comprises (c) determining, from the series of growth areas, a subset of growth areas that include clonal populations derived from a single transformant.

Embodiments disclosed herein include a method for isolating clonal populations derived from single clonal transformants. The method comprises (a) dispensing a discrete volume of a liquid suspension including a DNA source and a protoplast to each individual reaction area in a first substrate including a plurality of reaction areas. The dispensing is configured to generate, in each reaction area from the plurality of reaction areas, a transformation output in liquid media. The dispensing is such that the transformation output when subjected to a one-to-many distribution to a series of growth areas leads to a percentage of growth areas, from the series of growth areas, that result in a growth. The growth is such that it is derived from no more than a single transformant. The percentage of growth areas is at least one of above or below a predefined threshold value. The method further comprises (b) dispensing, in a high-throughput one-to-many manner, a discrete volume of transformation output in liquid media from each individual reaction area from the plurality of reaction areas, to the series of growth areas distributed across a plurality of second substrates. Each second substrate from the plurality of second substrates includes a plurality of growth areas mapped to correspond to the plurality of reaction areas included in the first substrate. The method further comprises (c) culturing growth in each growth area of the series of growth areas distributed across the plurality of second substrates. The method further comprises (d) selecting, from the series of growth areas, a subset of growth areas that include clonal populations derived from a single viable clonal transformant.

Embodiments disclosed include a high-throughput method for engineering a transformant cell that comprises (a) selecting a set of volumes of liquid suspension including a DNA source sample and a protoplast source associated with the cell. Each volume of the liquid suspension from the set of volumes of the liquid suspension is different, by at least one predetermined property, from the remaining volumes of the set of volumes of the liquid suspension. The method further comprises (b) distributing the set of volumes of the liquid suspension across a plurality of reaction areas, each reaction area from the plurality of reaction areas including a discrete quantity of the liquid suspension. The method further comprises (c) transforming the quantity of liquid suspension included in each reaction area from the plurality of reaction areas to generate a transformation output from a set of transformation outputs. The method further comprises (d) distributing the transformation output from the set of transformation outputs in a one-to-many manner to a series of growth areas from a plurality of growth areas. The method further comprises (e) evaluating the plurality of growth areas to calculate at least one of (i) a number of growth areas that included a successful transformant, or (ii) a number of growth areas that included growth of a clonal population derived from a single clonal transformant.

Embodiments disclosed include a high-throughput method for engineering a transformant cell, that comprises (a) dispensing discrete volumes of a liquid suspension, obtained from a reaction area from the plurality of reaction areas in a first substrate, to a series of growth areas from a plurality of series of growth areas. The series of growth areas are distributed across a plurality of second substrates. The plurality of reaction areas includes a set of transformants, and the dispensing is configured to generate a set of growth outputs including colonies derived from the set of transformants. The method further comprises (b) evaluating the set of growth outputs to calculate at least one of (i) a number of growth outputs that included colonies derived from a successful transformant, or (ii) a number of growth outputs that included colonies derived from a single clonal transformant.

Embodiments disclosed include a high-throughput method for engineering a transformant cell, that comprises (a) selecting a set of volumes of a liquid suspension including a DNA source and a protoplast source. Each volumes of the liquid suspension from the set of volumes of the liquid suspension is different from the remaining volumes of the set of volumes of the liquid suspension. The method further comprises (b) dispensing a discrete quantity of the liquid suspension to a plurality of reaction areas in a first substrate such that each volume of the liquid suspension from the set of volumes of the liquid suspension is dispensed to an individual reaction area in the first substrate including the plurality of reaction areas. The method further comprises (c) transforming the quantity of liquid suspension in each reaction area from the plurality of reaction areas to generate a transformation output from a set of transformation outputs. The method further comprises (d) distributing equal quantities of each transformation output from the set of transformation outputs from each individual reaction area from the plurality of reaction areas, to a series of growth areas from a plurality of series of growth areas distributed across a plurality of second substrates. The distributing is directed to generate a set of growth outputs including colonies derived from the set of transformation outputs. The method further comprises (d) evaluating the set of growth outputs to calculate at least one of (i) a number of transformation outputs that included a growth output derived from a successful transformant, or (ii) a number of transformation outputs that resulted in growth output derived from a single clonal transformant.

Embodiments disclosed include a system for highthroughput engineering of a cell. The system comprises a memory including a set of instructions, and a processor coupled to the memory and configured to execute the set of instructions. The set of instructions includes instructions to select a set of volumes of a reaction mixture in liquid media, the reaction mixture including a DNA source and a protoplast source. Each volume of the reaction mixture from the set of volumes of the reaction mixture is selected to be used to generate a transformant output from a set of transformant outputs. The set of instructions further includes instructions to receive data associated with the set of transformant outputs generated using the set of dilutions of the reaction mixture in liquid media. The set of instructions further includes instructions to receive data associated with a set of growth outputs generated using the set of transformation outputs, each transformation output from the set of transformation outputs being used to generate a series of growth outputs from a plurality of series of growth outputs in a one-to-many manner. The set of instructions further includes instructions to calculate a measure of rate of transformation based on at least one of the data associated with the set of transformant outputs or the data associated with a set of growth outputs.

A system for high-throughput liquid handling. The system comprises a pipetting unit including a pipettor including a shaft and a pipetting end extending from a distal end of the pipettor shaft. The system further comprises a motor unit coupled to the pipetting unit. The motor unit is configured to actuate the pipetting unit over a predefined path. The motor unit is further configured to releasably engage the pipetting end with a tip configured to hold a discreet amount of a liquid suspension including a predetermined concentration of at least one of a DNA source, a protoplast, and a transformation output. The motor unit is further configured to transfer the discreet amount of liquid suspension from a source of the liquid suspension to the tip when the pipetting end is engaged with the tip and when the pipetting unit is transitioned from a first configuration to a second configuration. The motor unit is further configured to transfer the discreet amount of liquid suspension from the tip to a destination of the mixture, when the pipetting end is engaged with the tip and when the pipetting unit is transitioned from the second configuration to the first configuration. The system further comprises an electronics unit that is operatively coupled to the pipetting unit and the motor unit. The electronics unit is configured to control the motor unit.

BRIEF DESCRIPTION OF THE DRAWINGS

FIG. 6 is a flowchart describing a method for evaluation of automated, high throughput strain generation using liquid media, according to some embodiments FIG. 7 is a flowchart describing a method for evaluation of automated, high throughput strain generation using liquid media, according to some embodiments.

FIG. 10 includes a schematic illustration of an example substrate with growth areas having potential growth of clonal transformant strains resulting from transformation outputs, according to some implementations.

FIG. 12 is a picture of a 96-well media plate of *A. niger* transformants. Transformed cultures comprise a mutation in the aygA, which causes the cells to appear lighter yellow instead of black (transformed wells are circled in white).

DETAILED DESCRIPTION

Definitions

Figure 1:
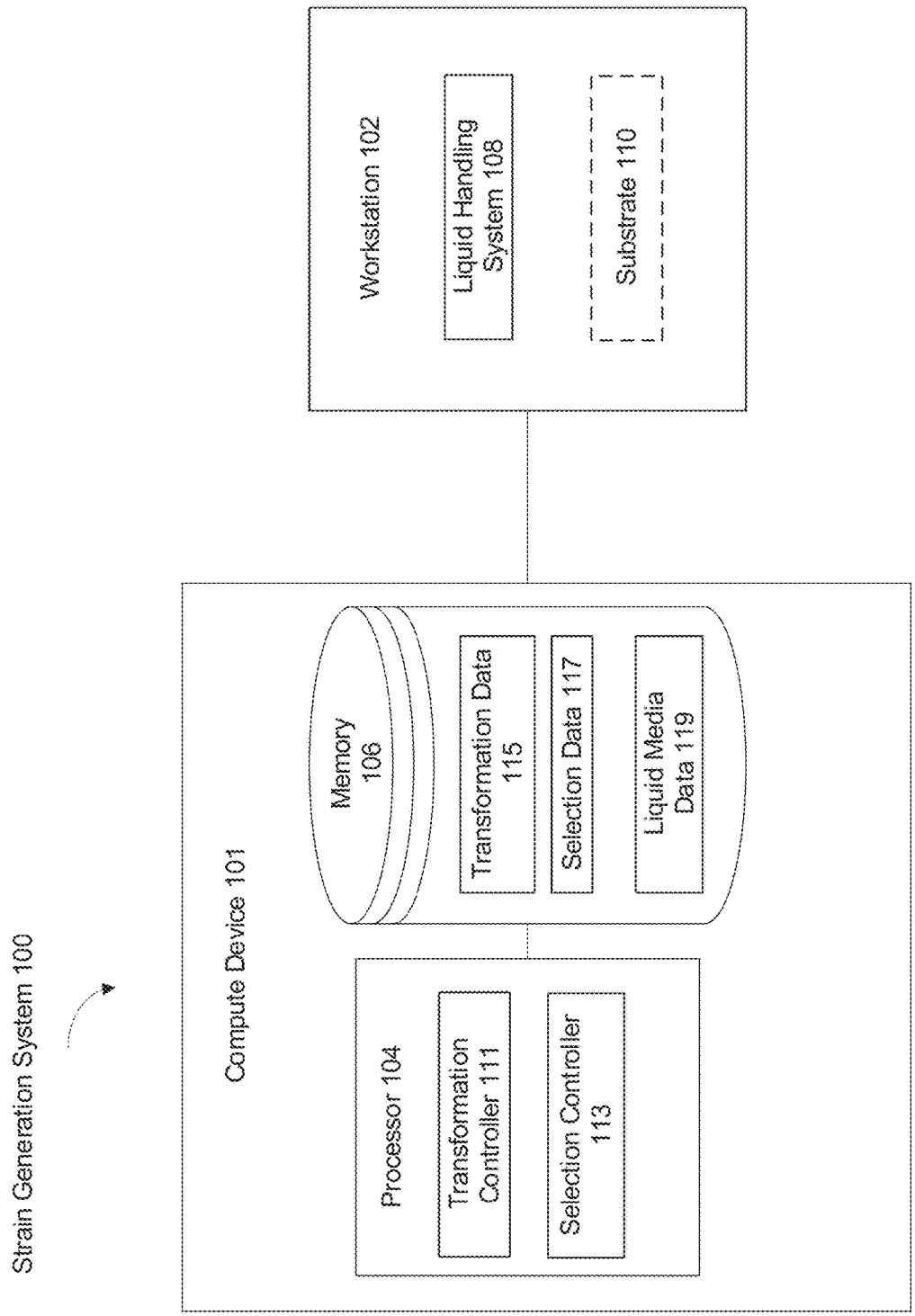
FIG. 1 is a schematic illustration of a strain generation system for performing automated, high throughput isolation and selection of clonal strains using liquid media, according to some embodiments.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16 S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell. In some embodiments, the present disclosure teaches the use of parent strains as control host cells (e.g., the S1 strain that was used as the basis for the strain improvement program). In other embodiments, a host cell may be a genetically identical cell that lacks a specific promoter or SNP being tested in the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing. A "recombination" or "recombination event" as used herein refers to a chromosomal crossing over or independent assortment.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art. As used herein, the term "at least a portion" or "fragment" of a nucleic acid or polypeptide means a portion having the minimal size characteristics of such sequences, or any larger fragment of the full-length molecule, up to and including the full-length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full-length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91: 10747-10751; Stemmer (1994) Nature 370: 389-391; Crameri et al. (1997) Nature Biotech. 15: 436-438; Moore et al. (1997) J. Mol. Biol. 272: 336-347; Zhang et al. (1997) PNAS 94: 4504-4509; Crameri et al. (1998) Nature 391: 288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from plasmid templates and/or cDNA or genomic DNA extracted from an organism of interest. Methods for designing PCR primers and PCR cloning are generally known in the art and are disclosed in Sambrook et al. (2001) Molecular Cloning: A Laboratory Manual (3rd ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source but arranged in a manner different than that found in nature. Such construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4: 2411-2418; De Almeida et al., (1989) Mol. Gen. Genetics 218: 78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others.

The term "carbon source" generally refers to a substance suitable to be used as a source of carbon for cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product of interest (e.g. small molecule, peptide, synthetic compound, fuel, alcohol, etc.) in a fermentation process. However, a feedstock may contain nutrients other than a carbon source.

The term "volumetric productivity" or "production rate" is defined as the amount of product formed per volume of medium per unit of time. Volumetric productivity can be reported in gram per liter per hour (g/L/h).

The term "specific productivity" is defined as the rate of formation of the product. Specific productivity is herein further defined as the specific productivity in gram product per gram of cell dry weight (CDW) per hour (g/g CDW/h). Using the relation of CDW to OD600 for the given microorganism specific productivity can also be expressed as gram product per liter culture medium per optical density of the culture broth at 600 nm (OD) per hour (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" is defined as the strength of a solution or the concentration of a substance in solution. For example, the titre of a product of interest (e.g. small molecule, peptide, synthetic compound, fuel, alcohol, etc.) in a fermentation broth is described as g of product of interest in solution per liter of fermentation broth (g/L).

The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process As used herein, the term "HTP genetic design library" or "library" refers to collections of genetic perturbations according to the present disclosure. In some embodiments, the libraries of the present invention may manifest as i) a collection of sequence information in a database or other computer file, ii) a collection of genetic constructs encoding for the aforementioned series of genetic elements, or iii) host cell strains comprising said genetic elements. In some embodiments, the libraries of the present disclosure may refer to collections of individual elements (e.g., collections of promoters for PRO swap libraries, or collections of terminators for STOP swap libraries). In other embodiments, the libraries of the present disclosure may also refer to combinations of genetic elements, such as combinations of promoter::genes, gene:terminator, or even promoter:gene: terminators. In some embodiments, the libraries of the present disclosure further comprise meta data associated with the effects of applying each member of the library in host organisms. For example, a library as used herein can include a collection of promoter::gene sequence combinations, together with the resulting effect of those combinations on one or more phenotypes in a particular species, thus improving the future predictive value of using said combination in future promoter swaps.

As used herein, the term "SNP" refers to Small Nuclear Polymorphism(s). In some embodiments, SNPs of the present disclosure should be construed broadly, and include single nucleotide polymorphisms, sequence insertions, deletions, inversions, and other sequence replacements. As used herein, the term "non-synonymous" or non-synonymous SNPs" refers to mutations that lead to coding changes in host cell proteins A "high-throughput (HTP)" method of genomic engineering may involve the utilization of at least one piece of automated equipment (e.g. a liquid handler or plate handler machine) to carry out at least one step of said method.

In some embodiments, a method includes dispensing a discrete volume of a liquid suspension including a predetermined concentration of a DNA source and a predetermined concentration of a protoplast source to an individual reaction area in a first substrate including a plurality of reaction areas. The method includes generating, in each reaction area from the plurality of reaction areas, a transformation output in liquid media such that the percentage of individual reaction areas that result in a transformation output that includes a successful transformant is below a predetermined threshold value. The method includes distributing equal volumes of transformation output in liquid media from each individual reaction area from the plurality of reaction areas, to a series of growth areas distributed across a plurality of second substrates. The method further includes culturing growth in each growth area of the series of growth areas distributed across the plurality of second substrates to generate clonal populations. The method further includes identifying and isolating clonal populations derived from a single transformant from the series of growth areas.

In some embodiments, an apparatus includes a memory including a set of instructions, and a processor coupled to the memory and configured to execute the set of instructions. The processor is configured to select a set of volumes of a reaction mixture in liquid media. The reaction mixture includes a DNA source and a protoplast source, and each volume of the reaction mixture from the set of volumes of the reaction mixture is selected to be used to generate a transformant output from a set of transformant outputs. The processor is configured to receive data associated with the set of transformant outputs generated using the set of dilutions of the reaction mixture in liquid media. The processor is further configured to receive data associated with a set of growth outputs generated using the set of transformation outputs, with each transformation output from the set of transformation outputs being used to generate a series of growth outputs from a plurality of series of growth outputs in a one-to-many manner. The processor is further configured to calculate a measure of rate of transformation based on at least one of the data associated with the set of transformant outputs or the data associated with a set of growth outputs.

Overview

Filamentous fungi are valuable organisms as they can be genetically engineered to harness their cellular mechanisms to produce specific biomolecules or products of interest. Genetically engineered fungal cells can be produced by introducing foreign DNA, required to express a desired biomolecule, in a selected locus of the genome of a fungal cell (e.g., a protoplast). The use of genetically engineered fungal strains to produce commercially valuable products also depends on maintenance and/or improvement of genetically pure fungal strains through clonal enrichment of high producer cells. High-throughput genetic engineering in filamentous fungi is desirable for efficiently improving strain performance in industrial applications. High-throughput genetic engineering of filamentous fungi also opens up possibilities to increase the number and types of synthetic biology applications in which an identified fungal strain can be used.

Persons having skill in the art will recognize that the methods of the present disclosure are compatible with host cells producing any desirable biomolecule product of interest. Table 1 below presents a non-limiting list of the product categories, biomolecules, and host cells, compatible with the present disclosure. These examples are provided for illustrative purposes only and are not meant to limit the applicability of the presently disclosed technology in any way.

TABLE 1

| A non-limiting list of the host cells and products of interest of the present disclosure. | | | |
|---|---|---|---|
| Product category | Products | Host category | Hosts |
| Flavor & Fragrance | Agarwood | Yeast | Saccharomyces cerevisiae |
| Flavor & Fragrance | Ambrox | Yeast | Saccharomyces cerevisiae |
| Flavor & Fragrance | Nootkatone | Yeast | Saccharomyces cerevisiae |
| Flavor & Fragrance | Patchouli oil | Yeast | Saccharomyces cerevisiae |
| Flavor & Fragrance | Saffron | Yeast | Saccharomyces cerevisiae |
| Flavor & Fragrance | Sandalwood oil | Yeast | Saccharomyces cerevisiae |
| Flavor & Fragrance | Valencene | Yeast | Saccharomyces cerevisiae |
| Flavor & Fragrance | Vanillin | Yeast | Saccharomyces cerevisiae |
| Food | CoQ10/Ubiquinol | Yeast | Schizosaccharomyces pombe |
| Food | Omega 3 fatty acids | Microalgae | Schizochytrium |
| Food | Omega 6 fatty acids | Microalgae | Schizochytrium |
| Food | Vitamin B2 | Filamentous fungi | Ashbya gossypii |
| Food | Erythritol | Yeast-like fungi | Torula coralline |
| Food | Erythritol | Yeast-like fungi | Pseudozyma tsukubaensis |

TABLE 1-continued

A non-limiting list of the host cells and products
of interest of the present disclosure.

| Product category | Products | Host category | Hosts |
| --- | --- | --- | --- |
| Food | Erythritol | Yeast-like fungi | *Moniliella pollinis* |
| Food | Steviol glycosides | Yeast | *Saccharomyces cerevisiae* |
| Organic acids | Citric acid | Filamentous fungi | *Aspergillus niger* |
| Organic acids | Citric Acid | Filamentous fungi | *Aspergillus carbonarius* |
| Organic acids | Citric Acid | Filamentous fungi | *Aspergillus aculeatus* |
| Organic acids | Citric acid | Yeast | *Pichia guilliermondii* |
| Organic acids | Gluconic acid | Filamentous fungi | *Aspergillus niger* |
| Organic acids | Itaconic acid | Filamentous fungi | *Aspergillus terreus* |
| Organic acids | Itaconic acid | Filamentous fungi | *Aspergillus niger* |
| Organic acids | LCDAs - DDDA | Yeast | *Candida* |
| Organic acids | Kojic Acid | Filamentous fungi | *Aspergillus oryzae* |
| Organic acids | Kojic Acid | Filamentous fungi | *Aspergillus flavus* |
| Organic acids | Kojic Acid | Filamentous fungi | *Aspergillus tamarii* |
| Organic acids | Malic Acid | Filamentous fungi | *Aspergillus oryzae* |
| Organic acids | Oxalic acid | Filamentous fungi | *Aspergillus niger* |
| Organic acids | Succinic acid | Filamentous fungi | *Aspergillus saccarolyticus* |
| Organic acids | Lactic acid | Filamentous fungi | *Aspergillus niger* |
| Organic acids | Lactic acid | Filamentous fungi | *Aspergillus brasiliensis* |
| Hypolipidemic agent | Lovastatin | Filamentous fungi | *Aspergillus terreus* |
| Melanogenesis inhibitor | Terrein | Filamentous fungi | *Aspergillus terreus* |
| Immunosuppresent drug | Cyclosporine A | Filamentous fungi | *Aspergillus terreus* |
| Antiproliferative agent | Asperfuranone | Filamentous fungi | *Aspergillus terreus* |
| Antiproliferative agent | Asperfuranone | Filamentous fungi | *Aspergillus nidulans* |
| Cholesterol-lowering agent | Pyripyropene | Filamentous fungi | *Aspergillus fumigatus* |
| Antibiotics | Penicillin | Filamentous fungi | *Aspergillus oryzae* |
| Antibiotics | Penicillin | Filamentous fungi | *Aspergillus nidulans* |
| Antimicrobial agent | Fumagillin | Filamentous fungi | *Aspergillus fumigatus* |
| Anticancer agent | Fumitremorgin C | Filamentous fungi | *Aspergillus fumigatus* |
| Anticancer agent | Spirotryprostatins | Filamentous fungi | *Aspergillus fumigatus* |
| Anticancer agent; Antimicrobial agent | Plinabulin | Filamentous fungi | *Aspergillus ustus* |
| Anticancer agent | Phenylahistin | Filamentous fungi | *Aspergillus ustus* |
| Anticancer agent | Stephacidin A & B | Filamentous fungi | *Aspergillus ochraceus* |
| Anticancer agent | Asperphenamate | Filamentous fungi | *Aspergillus flavus* |
| Cholecystokinin antagonist | Asperlicin | Filamentous fungi | *Aspergillus alliaceus* |
| Industrial enzyme | Alpha-amylase | Filamentous fungi | *Aspergillus niger* |
| Industrial enzyme | Alpha-amylase | Filamentous fungi | *Aspergillus oryzae* |
| Industrial enzyme | Aminopeptidase | Filamentous fungi | *Aspergillus niger* |
| Industrial enzyme | Aminopeptidase | Filamentous fungi | *Aspergillus oryzae* |

TABLE 1-continued

A non-limiting list of the host cells and products of interest of the present disclosure.

| Product category | Products | Host category | Hosts |
|---|---|---|---|
| Industrial enzyme | Aminopeptidase | Filamentous fungi | *Aspergillus sojae* |
| Industrial enzyme | AMP deaminase | Filamentous fungi | *Aspergillus melleus* |
| Industrial enzyme | Catalase | Filamentous fungi | *Aspergillus niger* |
| Industrial enzyme | Cellulase | Filamentous fungi | *Aspergillus niger* |
| Industrial enzyme | Chymosin | Filamentous fungi | *Aspergillus niger* |
| Industrial enzyme | Esterase | Filamentous fungi | *Aspergillus niger* |
| Industrial enzyme | Alpha-galactosidase | Filamentous fungi | *Aspergillus niger* |
| Industrial enzyme | Beta-glucanase | Filamentous fungi | *Aspergillus niger* |
| Industrial enzyme | Beta-glucanase | Filamentous fungi | *Aspergillus aculeatus* |
| Industrial enzyme | Glucose oxidase | Filamentous fungi | *Aspergillus niger* |
| Industrial enzyme | Glutaminase | Filamentous fungi | *Aspergillus oryzae* |
| Industrial enzyme | Glutaminase | Filamentous fungi | *Aspergillus sojae* |
| Industrial enzyme | Beta-D-Glucosidase | Filamentous fungi | *Aspergillus niger* |
| Industrial enzyme | Inulinase | Filamentous fungi | *Aspergillus niger* |
| Industrial enzyme | Lactase | Filamentous fungi | *Aspergillus niger* |
| Industrial enzyme | Lipase | Filamentous fungi | *Aspergillus niger* |
| Industrial enzyme | Lipase | Filamentous fungi | *Aspergillus oryzae* |
| Industrial enzyme | Xylanase | Filamentous fungi | *Aspergillus niger* |

Strain selection and clonal enrichment of filamentous fungi involve several challenges. Protoplasts derived from filamentous fungi can often contain more than one nucleus such that subsequent transformation with a construct (e.g., insert DNA fragment) can produce transformants that are heterokaryotic such that the construct (e.g., insert DNA fragment) is incorporated into only a subset of the multiple nuclei present in the protoplast. It is of interest to increase the relative number or percentage of homokaryotic transformants following transformation.

While methods currently exist for high-throughput manipulations in filamentous fungi (U.S. Pat. No. 10,336, 998), they rely on strains going through sporulation for selection of homokaryotic transformants expressing a desired target gene. Sporulation is also relied upon for clonal enrichment and isolation of the genetically desired transformants. Several industrially valuable fungi, however, are not capable of sporulation. Additionally, a large number of the valuable fungi that are capable of spore formation sporulate very poorly, thereby precluding or severely limiting the application of existing high-throughput methods for strain improvement. The presently disclosed systems and methods circumvent the requirement for sporulation to reach clonality allowing the application of high-throughput genetic engineering programs to non-sporulating strains of filamentous fungi.

FIG. 1 is a schematic illustration of a strain generation system 100, also referred to herein as "SGS system" or "system". The strain generation system 100 can be configured for performing automated, high throughput cellular strain generation. The strain generation system 100 is configured to control, manage and/or implement the high-throughput generation and/or selection of clonal strains of engineered cells that may be used for production of products of interest. The system 100 can be configured to control and/or implement high-throughput methods of strain generation and/or strain selection in non-sporulating, filamentous fungi by using liquid media thereby circumventing a need for sporulation.

As shown in FIG. 1, the system 100 includes a compute device 101 and a work station 102. The compute device 101 can each be any suitable hardware-based computing device and/or a multimedia device, such as, for example, a server, a desktop compute device, a smartphone, a tablet, a wearable device, a laptop and/or the like. The compute device 101 includes a processor 104 and a memory 106.

The memory 106 of the compute device 101 can be, for example, a random-access memory (RAM), a memory buffer, a hard drive, a read-only memory (ROM), an erasable programmable read-only memory (EPROM), and/or the like. The memory 106 can store, for example, one or more software modules and/or code that can include instructions to cause the processor 104 to perform one or more processes, functions, and/or the like (e.g., the transformation controller 111, the selection controller 113). The system 100 can receive data from the work station and/or from external sources (e.g., from remote data bases not shown in FIG. 1) data associated with high through generation and selection of target strains of non-sporulating, filamentous fungi and store data associated with the high throughput generation and/or selection of a strain of non-sporulating, filamentous fungi.

In some embodiments, the memory 106 can include extendable storage units that can be added and used incrementally. In some implementations, the memory 106 can be a portable memory (for example, a flash drive, a portable hard disk, and/or the like) that can be operatively coupled to the processor 104. In other instances, the memory can be remotely operatively coupled with the compute device. For example, a remote database server can serve as a memory and be operatively coupled to the compute device.

The memory 106 stores Transformation Data 115, Selection Data 117, and Liquid Media Data 119. Transformation Data 115 can be associated with high-throughput generation of genetically engineered clonal transformants with a target DNA inserted in the host genome to express desired biomolecules. Transformation Data 115 can include information related to the DNA or polynucleotide for use in transforming a filamentous fungal cell or protoplast derived therefrom. The DNA used can be an endogenous gene or a heterologous gene relative to the variant strain and/or the parental strain. The endogenous gene or heterologous gene can encode a product or protein of interest as described herein. As described previously, the protein of interest can refer to a polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be expressed intracellularly or as a secreted protein. The endogenous gene or heterologous gene can include a mutation and/or be under the control of or operably linked to one or more genetic control or regulatory elements. The mutation can be any mutation provided herein such as, for example, an insertion, deletion, substitution and/or single nucleotide polymorphism. The one or more genetic control or regulatory elements can be a promoter sequence and/or a terminator sequence. The endogenous gene or heterologous gene can be present on one expression construct or split across multiple expression constructs Transformation Data 115 can include data related reaction inputs to be used to setup and perform high-throughput transformation in reaction areas (e.g., wells) included in one or more substrates (e.g., transformation plates).

In some implementations, Transformation Data 115 can include parameters associated with the reaction inputs setup for high throughput transformation. Reaction inputs for transformation can include known concentration of desired DNA fragments to be inserted in the host cell genome (e.g., in the form of DNA fragments that are products of amplification using PCR), a known concentration of host cells (e.g., protoplasts), enrichment medium (e.g., PEG), etc. Parameters associated with the reaction inputs can include a volume of each of the reaction inputs, an altered concentration of each of the reaction inputs, an amount of foreign DNA added from a DNA source, locus or loci of interest for DNA manipulation on the host protoplast genome, a nature of protoplast (e.g., homokaryotic) and/or the like.

In some implementations, Transformation Data 115 can include information related to a workflow involved in the transformation of host cell to generate genetically engineered transformants. For example, Transformation Data 115 can include one or more phases associated with transformation. The one or more phases can include PCR based amplification of desired DNA to generate a known concentration of DNA source, stamping of DNA source onto substrates having reaction areas (also referred to herein as "wells"), stamping of enrichment inputs (e.g., PEG) onto reaction areas having DNA course and a host cell, evaluation of transformation outputs following predefined QC criteria, and the determination of a measure of success and/or failure of transformation according to specified QC requirements. In some implementations, Transformation Data 115 can include one or more criteria used during QC checks to ascertain a measure of success and/or failure of high-throughput transformation. For example, QC requirements for transformation can include a requirement that a proportion of reaction areas in a substrate for transformation (also referred to herein as "transformation plate") that include a transformant cell is above or below a specified first threshold criterion. For example, the threshold value can be l %, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%. In some instances, QC requirements can include a requirement that a proportion of reaction areas in a substrate for transformation (e.g., a percentage of wells in a transformation plate) that incudes no more than a single transformant is above or below a specific second threshold value. For example, the second threshold value can be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%. In some instances, the Transformation Data 115 (e.g., threshold criteria) can be received from an external source and/or provided by a user of the system 100.

Transformation Data 115 can include other parameters related to a workflow involved in transformation such as a duration of incubation, one or more conditions associated with the phases of process of transformation including temperature, duration, enrichment media, and/or the like. In some implementations, Transformation Data 115 can include information associated with the results of high-throughput transformation, namely the transformation outputs. Information associated with transformation outputs can include one or more indicators that can be used to evaluate a success or a failure of transformation as part of a Quality Control (QC) check. For example, Transformation Data 115 can include data related to QC methods and practices of determining the reaction areas (e.g., wells) that indicate a successful transformation (e.g., as evidenced by the occurrence of a genotype and/or phenotype). In some instances, Transformation Data 115 can include data related to QC methods and practices of determining the reaction areas (e.g., wells) that indicate a single transformant i.e. number and/or identity of reaction areas (e.g., wells in a transformation plate) with no more than a single transformant. In some instances, Transformation Data 115 can include data related to an identification of a karyotype of a single transformant (e.g., homokaryotic, heterokaryotic) in a subset of reaction areas of a transformation substrate (e.g., transformation plate) as determined through QC using a target genotype/phenotype. In some implementations, Transformation Data 115 can include data associated with one or more analyses conducted by the processor 104 (e.g., by the Transformation Controller 111). In some implementations, for example, the analyses can include a determination of a rate of transformation, or a rate of success of isolating a single transformant in individual reaction areas. In some instances, the system 100 can conduct iterative analyses of transformation using parameters with slight variations, In some instances, the analyses can include the identification of one or more parameters associated with transformation that are deemed to underlie the resultant success of transformation and/or success of isolating single transformants and/or a desired proportion of transformants that are identified to be homokaryotic/heterokaryotic for a specified gene locus.

Selection Data 117 can be associated with high-throughput selection of genetically engineered clonal transformants with a desired genotype and/or phenotype. Selection Data 117 can include parameters associated with the one-to-many distribution of transformation outputs from each reaction area (e.g., well) of a transformation substrate (e.g., transformation plate) to a series of reaction areas (e.g., wells) in a set of growth substrates (e.g., selection plates). In some implementations, Selection Data 117 can include data associated with one or more analyses conducted by the processor 104 (e.g., by the Selection Controller 113). In some implementations, for example, the analyses can include a determination of a rate of growth of clonal populations (e.g., percentage of the wells in a selection plate that indicate growth), or a rate of success of isolating a population arising from a single clonal transformant in individual reaction areas (e.g., percentage of the wells in a selection plate showing growth arising from a single transformant as determined from phenotype/genotype). In some instances, the analyses can include the identification of one or more parameters associated with transformation and/or distribution of transformant outputs that are deemed to underlie the resultant success of clonality and/or success of isolating clonal populations arising from a single transformant and/or a desired proportion of clonal populations (e.g., percentage of the wells in a selection plate) that are identified to be homokaryotic/heterokaryotic for a specified gene locus.

Liquid Media Data 119 can be any suitable information associated with high throughput methods of liquid handling used for the transformation to generate selected strains and/or the isolation and selection of clonal populations resulting from single transformants (e.g., homokaryotic transformant for a desired gene locus). In some implementations, Liquid Media Data 119 can include data related to dilutions of the reaction inputs for transformation, volume, molar ratio or DNA products to be added to reaction inputs prepared for transformation, specific amounts of DNA ends (e.g., PCR products) to be added to set up transformation plates. In some implementations, Liquid Media Data 119 can include data related to discreet volumes and/or dilutions of transformation outputs to be obtained from each selected reaction area (e.g., well) on a transformation plate and to be distributed across a series of reaction areas (e.g., wells) in a set of substrates (e.g., selection plates). In some implementations, Liquid Media Data 119 can include information related to a transfer (e.g., via stamping) of a pre-determined amount of DNA in liquid form on to a substrate including reaction areas having one or more protoplasts. In some implementations, Liquid Media Data 119 can include information related to a transfer (e.g., via stamping) of a pre-determined amount of enrichment medium (e.g., polyethylene glycol PEG) in liquid form on to a substrate including reaction areas having a discreet volume of a DNA source and one or more protoplasts. In some implementations, Liquid Media Data 119 can include instructions related to a transfer (e.g., via stamping) of a pre-determined amount of DNA in liquid form on to a substrate including reaction areas having one or more protoplasts. In some implementations, Liquid Media Data 119 can include instructions related to a distribution (e.g., via one-to-many transfers) of a pre-determined amount of transformation output in liquid form on to a substrate including reaction areas for growth of colonies arising from single clonal transformants.

The processor 104 can be, for example, a hardware based integrated circuit (IC) or any other suitable processing device configured to run and/or execute a set of instructions or code. For example, the processor 104 can be a general-purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC) and/or the like. The processor 104 can be operatively coupled to the memory 106 through a system bus (for example, address bus, data bus and/or control bus).

The processor includes a Transformation Controller 111 and a Selection Controller 113. The Transformation Controller 111 can be configured to, upon execution, control and/or implement preparation of fine-tuned reaction inputs for generating genetically engineered cells using liquid media. The Transformation Controller 111 can be configured to receive Transformation Data 115 from the memory 106 and based on the Transformation Data 115 implement a setup of reaction areas in one or more substrates (e.g., substrate 110).

In some implementations, the Transformation Controller 111 can co-ordinate transformation using carefully controlled inputs of DNA source and protoplast source. The Transformation Controller 111 can be configured to implement one or more steps in a workflow involved in transformation as described herein. In some implementations, the Transformation Controller 111 can be configured to send and receive instructions to and from the work station 102 such that one or more components of the work station 102 may be automatically or semi-automatically controlled to implement one or more of the processed involved in the transformation of a host cell with target DNA. For example, in some implementations, the Transformation Controller 111 can be configured to determine specified reaction inputs to achieve high-throughput generation of genetically engineered transformant cells via introducing DNA into protoplasts using transformation in liquid media. In some implementations, the Transformation Controller 111 can be configured to select a suitable method for transformation of a particular strain of interest. Methods of transformation can include methods like homologous recombination, using a non-homologous end joining pathway, CRISPR, or other gene editing techniques. In some implementations, the use of CRISP system for generating a genetically engineered filamentous fungal strain (e.g., Basidiomycete) may be particularly relevant given that some fungi, including Basidiomycetes, are known to be diploid and obligate heterokaryons. Thus, CRISPR used in conjunction with the systems and/or methods described herein for high-throughput strain generation can provide the possibility to make double edits in the genome of the strain which may be otherwise harder to accomplish using other methods such as homologous recombination.

In some implementations, the Transformation Controller 111 can be configured to select a set of volumes of a reaction mixture in liquid media (e.g., based on Transformation Data 115 and/or a set of instructions). For example, the reaction mixture can include a specified DNA source and a specified protoplast source, and each volume of the reaction mixture from the set of volumes of the reaction mixture can be selected to be used to generate a transformant output that can be evaluated.

In some implementations, the Transformation Controller 111 can be configured to select the relative proportions of the reaction inputs (e.g., DNA, protoplast, etc.) such that transformation outputs are obtained that when distributed in a one-to-many manner result in a desired target number of clonal transformants obtained in growth areas with a reasonable predictability and/or reproducibility. In some implementations, the reproducibility can be quantified by a measure of probability that a specified fraction of growth areas in a selection plate include a desired number of transformants and/or clonal populations. The probability can be 0.1, 0.2, 03, 0.4, 0.5, 0.6, 0.7, 0.8, 0.9, 1.0 or any number in between those specified herein. In some implementations, optionally the transformation outputs can also be evaluated for rate of success and/or failure of transformation.

In some implementations, the Transformation Controller 111 can be configured to select the relative proportions of the reaction inputs such that a target amount of desired type of transformant is obtained. For example, the Transformation Controller 111 can be configured to select and implement preparation of reaction inputs. Preparation of reaction inputs can include transferring specific volumes and/or concentrations of individual reaction inputs (DNA fragments, PCR products, etc.). In some implementations, the Transformation Controller 111 can be configured to implement stamping of plates having wells with DNA source in liquid medium with plates including a known number of protoplasts in each well also in liquid medium. The transformation Controller 111 can be configured to implement stamping of one or more enrichment solutions (e.g., PEG) onto plates with reaction areas having DNA source stamped onto protoplasts.

In some implementations, the transformation controller 111 can receive data associated with results from a transformation and can evaluate a measure of success and/or failure associated with the transformation according to one or more predefined quality control (QC) criteria as described previously. For example, the transformation controller 111 can receive information associated with a set of transformant outputs generated using a set of dilutions of the reaction mixture in liquid media and the transformation controller 111 can determine the suitability of the set of dilutions of the reaction mixture for high-throughput transformation of the desired engineered cell. The transformation controller 111 can determine the suitability using one or more QC requirements. An example requirement can be that the proportion of reaction areas (e.g., wells) in the evaluated substrate for transformation (i.e. transformation plate) that include a successful transformant cell is above or below a specified first threshold criterion (e.g., above 70% saturation). An example requirement can be that the proportion of growth areas (e.g., wells in selection plates following the one-to-many distribution of transformation outputs) in the substrate evaluated for growth (i.e. selection plate) that include a population from a single transformant cell is above or below a specified first threshold criterion (e.g., above 15% saturation). Another example requirement can be that the proportion of growth areas in a selection plate that include growth (i.e. grow vs. a no-grow area) derived from a transformant is above or below a specific second threshold value (e.g., more than 15% of the wells include clonal (homokaryotic) populations from a single transformant).

In some implementations, the set of dilutions to be used and/or a threshold criterion to be used for a target saturation can be determined based on prior knowledge of an efficacy associated with homologous recombination for the particular strain of interest. For example, for a first strain of filamentous fungi know to be capable of high rates of homologous recombination a relatively higher threshold criterion for saturation can be used compared to a second strain of filamentous fungi know to show lesser rates of homologous recombination.

In some implementations, the evaluation of transformation outputs included in a transformation plates can be conducted using any suitable method by taking advantage of a genotypic and/or phenotypic identification of specified transformants/transformant number. In some cases, transformation of the target cell (e.g., non-sporulating filamentous fungi) can be directed such that two or more loci can be targeted for manipulation such that. in addition to the expression of a desired biomolecule the genetically engineered cells are configured to express a selectable marker gene. The selectable marker gene can be an auxotrophic marker gene, a colorimetric marker gene or a directional marker gene. The resulting phenotypic markers can be used to determine a quantity and/or quality of transformant outputs. For example, the transformation controller 111 can be configured to implement a method of generating a colorimetric measurement which can be used to calculate a transformant number associated with each well, and/or determine if each well included at least one transformant/no more than a single transformant. In some implementations, transformant cells can be directed to express markers such that the transformation controller 111 can implement a method of generating a colorimetric measurement which can be used to determine if a single transformant in the well was homokaryotic or heterokaryotic.

The Selection Controller 113 can be configured to, upon execution, control and/or implement a high-throughput one-to-many distribution of discreet volumes of transformation outputs from individual reaction areas (e.g., wells) in liquid media to a series of reaction areas (e.g., wells) in a set of substrates (e.g., selection plates). In some implementations, the Selection Controller 113 can co-ordinate the distribution of the transformation outputs in liquid media across a series of selection plates by controlling properties of the discreet volumes of transformation outputs being distributed across series of selection plates.

The Selection Controller 113 can be configured to implement one or more steps in a workflow involved in the distribution and selection of clonal populations as described herein. For example, in some implementations, the Selection Controller 113 can be configured to determine specified reaction inputs to achieve high-throughput generation of genetically engineered transformant cells via introducing DNA into protoplasts using transformation in liquid media. In some implementations, the Selection Controller 113 can be configured to send and receive instructions to and from the work station 102 such that one or more components of the work station 102 may be automatically or semi-automatically controlled to implement one or more of the processes involved in the controlled one-to-many distribution of transformation outputs to a series of selection plates, the evaluation of growth in the selection plates and the isolation and collection of selected clonal populations from the selection plates.

In some implementations, the Selection Controller 113 can be configured to select a set of transformation outputs in liquid media (e.g., based on Transformation Data 115, Selection Data 117, and/or a set of instructions). For example, the transformation outputs can be selected to ascertain purity of resulting growth and for providing the ease of identifying desired transformants (e.g., homokaryotic for a desired locus) and discarding undesired transformation outputs.

In some implementations, the Selection Controller 113 can receive data associated with strain selection results from a transformation and can evaluate a measure of success and/or failure associated with the strain selection according to one or more predefined quality control (QC) criteria as described previously. For example, the Selection Controller 113 can receive information associated with a set of growth outputs from a set of selection plates generated using a set of transformation outputs in liquid media and the Selection Controller 113 can determine the suitability of the transformation process, the reaction mixtures used for the transformation, properties of the transformation outputs (e.g., dilution of transformation outputs) and/or the distribution of discreet volumes of the transformation outputs across selection plates for high-throughput isolation and selection of a desired clonal population, for example, a desired clonal population of a non-sporulating filamentous fungus.

The Selection Controller 113 can determine the suitability using one or more QC requirements. An example requirement can be that the proportion of reaction areas (e.g., wells) in the evaluated substrates for strain selection (i.e. selection plates) that include a successful transformant cell is above or below a specified first threshold criterion (e.g., above 80% saturation). Another example requirement can be that the proportion of reaction areas in a selection plate that include no more than a single transformant is above or below a specific second threshold value (e.g., more than 70% of the wells include no more than a single transformant). In some implementations, the evaluation of growth outputs included in a selection plates can be conducted using any suitable method by taking advantage of a genotypic and/or phenotypic identification of specified transformants/transformant number. In some cases, similar to methods described with reference to evaluation of transformation plates, two or more loci can be targeted for manipulation during transformation such that, in addition to the expression of a desired biomolecule the genetically engineered cells are configured to express a selectable marker gene. The selectable marker gene can be an auxotrophic marker gene, a colorimetric marker gene or a directional marker gene. The resulting phenotypic markers can be used to determine a quantity and/or quality of transformant outputs. For example, the Selection Controller 113 can be configured to implement a method of generating a colorimetric measurement which can be used to calculate a density associated with clonal populations in each well, and/or determine if each well included growth resulting from at least one transformant/no more than a single transformant. In some implementations, transformant cells can be directed to express markers such that the Selection Controller 113 can implement a method of generating a colorimetric measurement which can be used to determine if the growth resulting from a single transformant in a well was homokaryotic or heterokaryotic.

The Transformation Controller 111 and/or the Selection Controller 113 can be configured to, upon execution, evaluate a success or failure associated with a workflow to generate and/or isolate clonal variants of filamentous non-sporulating fungi. In some implementations, the system 100 can evaluate various parameters associated with the transformation and/or distribution of transformation outputs based on a pre-determined Quality Control (QC) metric. The system 100 can then predict, based on one or more QC analyses an optimal set of parameters best suited to reach target efficiency metrics.

The workstation 102 is operatively coupled to the compute device 101 and can communicate with the compute device 101 via any suitable communication network. The communication network (not shown) can be any suitable communication network for transferring data, operating over public and/or private networks. For example the network can include a private network, a Virtual Private Network (VPN), a Multiprotocol Label Switching (MPLS) circuit, the Internet, an intranet, a local area network (LAN), a wide area network (WAN), a metropolitan area network (MAN), a worldwide interoperability for microwave access network (WiMAX®), an optical fiber (or fiber optic)-based network, a Bluetooth® network, a virtual network, and/or any combination thereof. In some instances, the communication network 106 can be a wireless network such as, for example, a Wi-Fi or wireless local area network ("WLAN"), a wireless wide area network ("WWAN"), and/or a cellular network. In other instances, the communication network can be a wired network such as, for example, an Ethernet network, a digital subscription line ("DSL") network, a broadband network, and/or a fiber-optic network. In some instances, the network can use Application Programming Interfaces (APIs) and/or data interchange formats, (e.g., Representational State Transfer (REST), JavaScript Object Notation (JSON), Extensible Markup Language (XML), Simple Object Access Protocol (SOAP), and/or Java Message Service (JMS)). The communications sent via the network can be encrypted or unencrypted. In some instances, the communication network can include multiple networks or subnetworks operatively coupled to one another by, for example, network bridges, routers, switches, gateways and/or the like (not shown).

The workstation 102 includes a liquid handling system 108 and optionally includes a substrate 110 The Liquid handling system 108, according to some embodiments, includes an automated system that can include a wide variety of components, including, but not limited to: liquid handlers; one or more robotic arms; plate handlers for the positioning of microplates; plate sealers, plate piercers, automated lid handlers to remove and replace lids for wells on non-cross contamination plates; disposable tip assemblies for sample distribution with disposable tips; washable tip assemblies for sample distribution; 96 well loading blocks; integrated thermal cyclers; cooled reagent racks; microtiter plate pipette positions (optionally cooled); stacking towers for plates and tips; magnetic bead processing stations; filtrations systems; plate shakers; barcode readers and applicators.

The Liquid handling system 108, according to some embodiments, includes a pipetting unit, a motor unit, and an electronics unit (not shown in FIG. 1) The pipetting unit can include a pipettor including a shaft and a pipetting end extending from a distal end of the pipettor shaft. The electronics unit can be operatively coupled to the pipetting unit and the motor unit. The electronics unit can be configured to control the motor unit. The motor unit can be coupled to the pipetting unit. The motor unit can be configured to actuate the pipetting unit over a predefined path. In some instances, the predefined path can be set via the compute device 101. The motor unit can be configured to releasably engage the pipetting end with a tip configured to hold a discreet amount of a liquid suspension.

In some implementations, the liquid suspension can include reaction inputs for a transformation to generate a genetically engineered cell to produce a target biomolecule. For example, the liquid suspension can include a predetermined concentration of at least one of a DNA source and a protoplast. In some implementations, the liquid suspension can include transformation outputs or results of transformation to generate a genetically engineered cell to produce a target biomolecule. The liquid suspension can be directed to be distributed in a one-to-many manner to selection plates to generate clonal populations of the desired genetically engineered cell.

The motor unit of the liquid handling system 108 can be configured to transfer, when the pipetting end is engaged with the tip and when the pipetting unit is transitioned from a first configuration to a second configuration, the discreet amount of liquid suspension from a source of the liquid suspension to the tip. The motor unit is further configured to transfer, when the pipetting end is engaged with the tip and when the pipetting unit is transitioned from the second configuration to the first configuration, the discreet amount of liquid suspension from the tip to a destination of the mixture.

In some implementations, the system 100 can include an automated system can include a wide variety of components, including, but not limited to: liquid handlers; one or more robotic arms; plate handlers for the positioning of microplates; plate sealers, plate piercers, automated lid handlers to remove and replace lids for wells on non-cross contamination plates; disposable tip assemblies for sample distribution with disposable tips; washable tip assemblies for sample distribution; 96 well loading blocks; integrated thermal cyclers; cooled reagent racks; microtiter plate pipette positions (optionally cooled); stacking towers for plates and tips; magnetic bead processing stations; filtrations systems; plate shakers; barcode readers and applicators; and computer systems. Table 2 below provides a non-exclusive list of scientific equipment capable of carrying out one or more steps involved in the HTP engineering procedures disclosed herein.

TABLE 2

Non-exclusive list of Scientific Equipment Compatible with the HTP engineering methods of the present disclosure.

| Equipment Type | | Operation(s) performed | Compatible Equipment Make/Model/Configuration |
|---|---|---|---|
| Acquire and build DNA pieces | liquid handlers | Hitpicking (combining by transferring) primers/templates for PCR amplification of DNA parts | Hamilton Microlab STAR, Labcyte Echo 550, Tecan EVO 200, Beckman Coulter Biomek FX, BioFluidix GmbH BioSpot BT600 liquid handling workstation, or equivalents |
| | Thermal cyclers | PCR amplification of DNA parts | Inheco Cycler, ABI 2720, ABI Proflex 384, ABI Veriti, or equivalents |
| QC DNA parts | Fragment analyzers (capillary electrophoresis) | gel electrophoresis to confirm PCR products of appropriate size | Agilent Bioanalyzer, AATI Fragment Analyzer, or equivalents |
| | Sequencer (sanger: Beckman) | Verifying sequence of parts/templates | Beckman Ceq-8000, Beckman GenomeLab ™, or equivalents |
| | NGS (next generation sequencing) instrument | Verifying sequence of parts/templates | Illumina MiSeq series sequences, illumina Hi-Seq, Ion torrent, pac bio or other equivalents |
| | nanodrop/plate reader | assessing concentration of DNA samples | Molecular Devices SpectraMax M5, Tecan M1000, or equivalents. |
| Generate DNA assembly | liquid handlers | Hitpicking (combining by transferring) DNA parts for assembly along with cloning vector, addition of reagents for assembly reaction/process | Hamilton Microlab STAR, Labcyte Echo 550, Tecan EVO 200, Beckman Coulter Biomek FX, BioFluidix GmbH BioSpot BT600 liquid handling workstation, or equivalents |
| QC DNA assembly | Colony pickers | for inoculating colonies in liquid media | Scirobotics Pickolo, Molecular Devices QPix 420 |
| | liquid handlers | Hitpicking primers/templates, diluting samples | Hamilton Microlab STAR, Labcyte Echo 550, Tecan EVO 200, Beckman Coulter Biomek FX, BioFluidix GmbH BioSpot BT600 liquid handling workstation, or equivalents |
| | Fragment analyzers (capillary electrophoresis) | gel electrophoresis to confirm assembled products of appropriate size | Agilent Bioanalyzer, AATI Fragment Analyzer |
| | Sequencer (sanger: Beckman) | Verifying sequence of assembled plasmids | ABI3730 Thermo Fisher, Beckman Ceq-8000, Beckman GenomeLab ™, or equivalents |
| | NGS (next generation sequencing) instrument | Verifying sequence of assembled plasmids | Illumina MiSeq series sequences, illumina Hi-Seq, Ion torrent, pac bio or other equivalents |

TABLE 2-continued

Non-exclusive list of Scientific Equipment Compatible with the HTP engineering methods of the present disclosure.

| | Equipment Type | Operation(s) performed | Compatible Equipment Make/Model/Configuration |
|---|---|---|---|
| Prepare base strain and DNA assembly | centrifuge | spinning/pelleting cells | Beckman Avanti floor centrifuge, Hettich Centrifuge |
| Transform DNA into base strain | Electroporators | electroporative transformation of cells | BTX Gemini X2, BIO-RAD MicroPulser Electroporator |
| | Ballistic transformation | ballistic transformation of cells | BIO-RAD PDS1000 |
| | Incubators, thermal cyclers | for chemical transformation/heat shock | Inheco Cycler, ABI 2720, ABI Proflex 384, ABI Veriti, or equivalents |
| | Liquid handlers | for combining DNA, cells, buffer | Hamilton Microlab STAR, Labcyte Echo 550, Tecan EVO 200, Beckman Coulter Biomek FX, BioFluidix GmbH BioSpot BT600 liquid handling workstation, or equivalents |
| Integrate DNA into genome of base strain | Colony pickers | for inoculating colonies in liquid media or diluting transformant outputs | Scirobotics Pickolo, Molecular Devices QPix 420 |
| | Single cell/transformant dispensers | for dispensing single cells/transformants into wells on microtiter plate | Cellenion CellenONE, Berkeley Lights Beacon Instrument, FACS, or Cytena single cell printer |
| | Liquid handlers | For transferring cells onto Agar, transferring from culture plates to different culture plates (inoculation into other selective media) or dispensing diluted transformant preparations into microtiter plates | Hamilton Microlab STAR, Labcyte Echo 550, Tecan EVO 200, Beckman Coulter Biomek FX, BioFluidix GmbH BioSpot BT600 liquid handling workstation or equivalents |
| | Platform shaker-incubators | incubation with shaking of microtiter plate cultures | Kuhner Shaker ISF4-X, Infors-ht Multitron Pro |
| QC transformed strain | Colony pickers | for inoculating colonies in liquid media | Scirobotics Pickolo, Molecular Devices QPix 420 |
| | liquid handlers | Hitpicking primers/templates, diluting samples | Hamilton Microlab STAR, Labcyte Echo 550, Tecan EVO 200, Beckman Coulter Biomek FX, BioFluidix GmbH BioSpot BT600 liquid handling workstation or equivalents |
| | Thermal cyclers | cPCR verification of strains | Inheco Cycler, ABI 2720, ABI Proflex 384, ABI Veriti, or equivalents |
| | Fragment analyzers (capillary electrophoresis) | gel electrophoresis to confirm cPCR products of appropriate size | Infors-ht Multitron Pro, Kuhner Shaker ISF4-X |
| | Sequencer (sanger: Beckman) | Sequence verification of introduced modification | Beckman Ceq-8000, Beckman GenomeLab ™, or equivalents |
| | NGS (next generation sequencing) instrument | Sequence verification of introduced modification | Illumina MiSeq series sequences, illumina Hi-Seq, Ion torrent, pac bio or other equivalents |
| Select and consolidate QC'd strains into test plate | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |
| | Colony pickers | for inoculating colonies in liquid media | Scirobotics Pickolo, Molecular Devices QPix 420 |
| | Platform shaker-incubators | incubation with shaking of microtiter plate cultures | Kuhner Shaker ISF4-X, Infors-ht Multitron Pro |
| Culture strains in seed plates | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |

TABLE 2-continued

Non-exclusive list of Scientific Equipment Compatible with
the HTP engineering methods of the present disclosure.

| | Equipment Type | Operation(s) performed | Compatible Equipment Make/Model/Configuration |
|---|---|---|---|
| | Platform shaker-incubators liquid dispensers | incubation with shaking of microtiter plate cultures Dispense liquid culture media into microtiter plates | Kuhner Shaker ISF4-X, Infors-ht Multitron Pro Well mate (Thermo), Benchcel2R (velocity 11), plateloc (velocity 11) |
| | microplate labeler | apply barcoders to plates | Microplate labeler (a2+ cab - agilent), benchcell 6R (velocity 11) |
| Generate product from strain | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |
| | Platform shaker-incubators liquid dispensers | incubation with shaking of microtiter plate cultures Dispense liquid culture media into multiple microtiter plates and seal plates | Kuhner Shaker ISF4-X, Infors-ht Multitron Pro well mate (Thermo), Benchcel2R (velocity 11), plateloc (velocity 11) |
| | microplate labeler | Apply barcodes to plates | microplate labeler (a2+ cab - agilent), benchcell 6R (velocity 11) |
| Evaluate performance | Liquid handlers | For processing culture broth for downstream analytical | Hamilton Microlab STAR, Labcyte Echo 550, Tecan EVO 200, Beckman Coulter Biomek FX, BioFluidix GmbH BioSpot BT600 liquid handling workstation or equivalents |
| | UHPLC, HPLC | quantitative analysis of precursor and target compounds | Agilent 1290 Series UHPLC and 1200 Series HPLC with UV and RI detectors, or equivalent; also any LC/MS |
| | LC/MS | highly specific analysis of precursor and target compounds as well as side and degradation products | Agilent 6490 QQQ and 6550 QTOF coupled to 1290 Series UHPLC |
| | Spectrophotometer | Quantification of different compounds using spectrophotometer based assays | Tecan M1000, spectramax M5, Genesys 10S |
| Culture strains in flasks | Fermenters: | incubation with shaking | Sartorius, DASGIPs (Eppendorf), BIO-FLOs (Sartorius-stedim). Applikon innova 4900, or any equivalent |
| | Platform shakers | | |
| Generate product from strain | Fermenters: DASGIPs (Eppendorf), BIO-FLOs (Sartorius-stedim) | | |
| Evaluate performance | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |
| | UHPLC, HPLC | quantitative analysis of precursor and target compounds | Agilent 1290 Series UHPLC and 1200 Series HPLC with UV and RI detectors, or equivalent; also any LC/MS |
| | LC/MS | highly specific analysis of precursor and target compounds as well as side and degradation products | Agilent 6490 QQQ and 6550 QTOF coupled to 1290 Series UHPLC |
| | Flow cytometer | Characterize strain performance (measure viability) | BD Accuri, Millipore Guava |
| | Spectrophotometer | Characterize strain performance (measure biomass) | Tecan M1000, Spectramax M5, or other equivalents |

While the system 100 is shown to include one compute device 101, the system 100 according to other embodiments can include any number of compute devices similar in structure and/or function to the compute device 101. In some embodiments, the number of compute devices can be configured to communicate with each other via any suitable communication network as described previously.

HTP Microbial Strain Engineering Based Upon Genetic Design Predictions: An Example Workflow In some embodiments, the systems and methods disclosed herein teach the directed engineering of new host organisms based on the recommendations of the computational analysis systems of the present disclosure. Genetically engineering and generating new and/or improves strains of organisms can include a phase of building the DNA to be introduced into a host cell, a phase of building the strain of the transformed engineered cell by introducing the DNA and a phase of growing colonies of the transformed cell to evaluate performance of the strain. In some implementations, the phase of introducing the DNA to generate a genetically manipulated strain can include introduction of DNA and an evaluation of outputs of transformation. In some implementations, the phase of growing colonies of the transformed cell can include high-throughput expansion and growth of the transformed cells in conducive conditions. These phases are briefly described in the flow chart in FIG. 2A and in the example workflows depicted in FIGS. 2B, 2C, and 2D. Some of the steps involved in each phase are further described below. For non-sporulating filamentous fungi, as described previously, the systems and methods disclosed herein can be used to build a desired strain of non-sporulating filamentous fungi and to grow colonies for evaluation and/or further downstream processing, circumventing the need for sporulation of the obstacle of lack of sporulation.

Figure 2A:
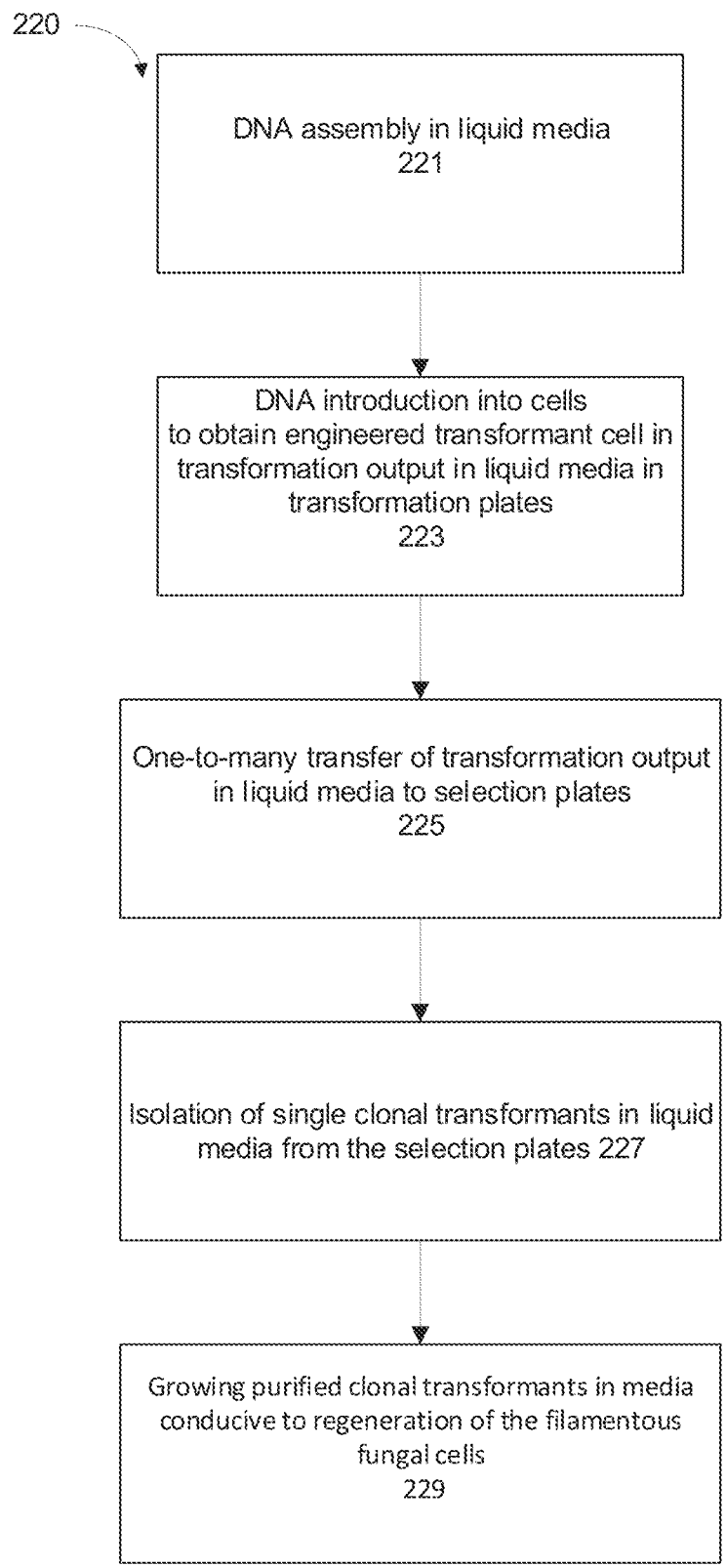
FIG. 2A is a flow chart showing a method for automated, high throughput strain generation using liquid media, according to some embodiments.
Figure 2:
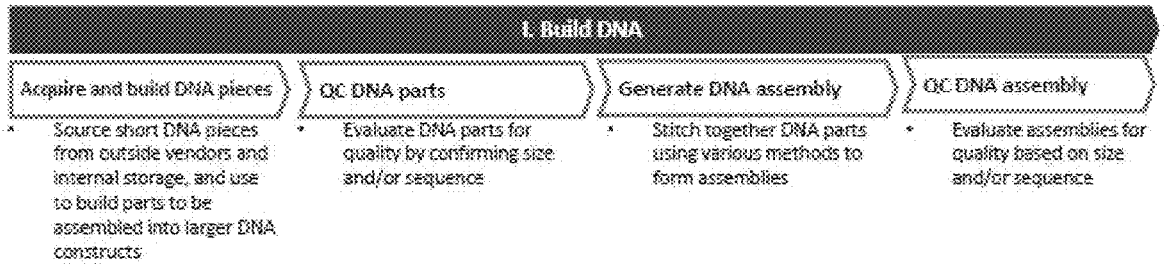
FIG. 2B depicts an example workflow directed to strain generation involving the DNA assembly, according to some embodiments.
FIG. 2C depicts an example workflow directed to transformation steps of strain generation, according to some embodiments.
FIG. 2D depicts the steps for high-throughput culturing, screening, and evaluation of selected host filamentous fungal strains.
Figure 2:
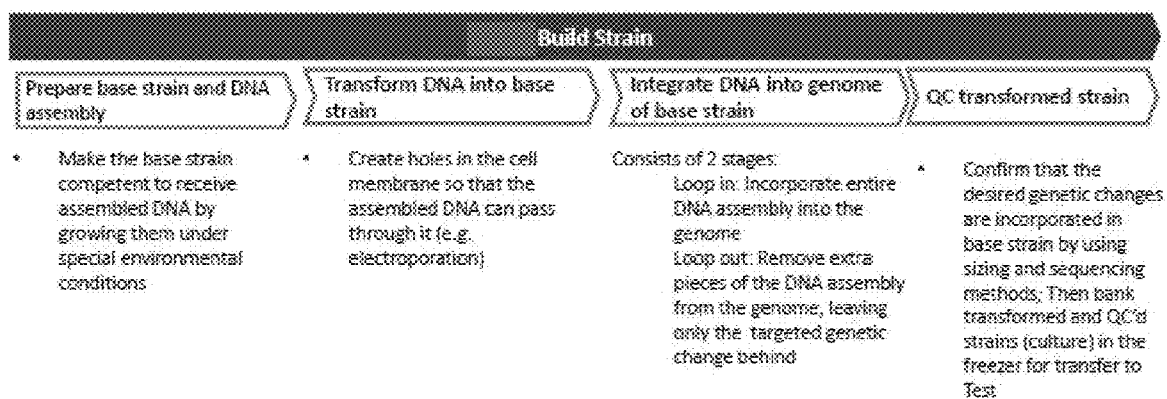
Figure 2:
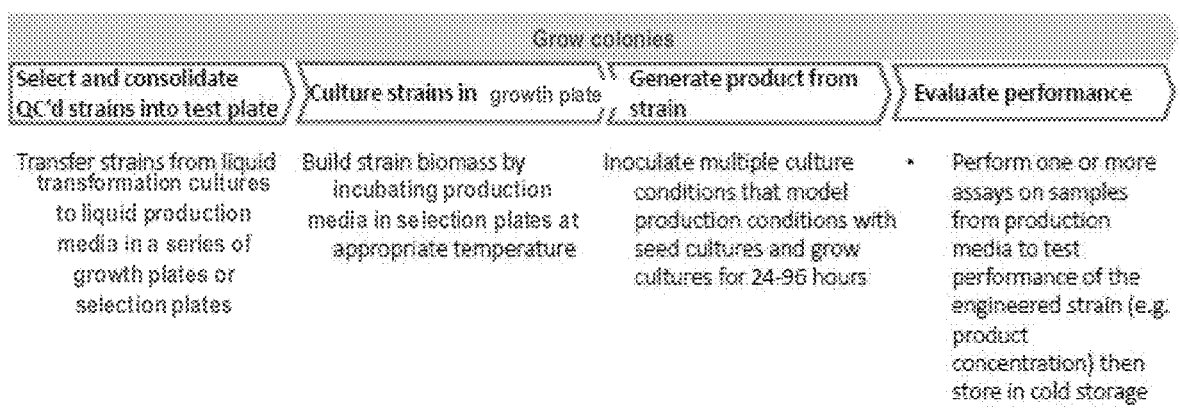

FIG. 2A is a flowchart illustrating an example method 220 associated with the generation and isolation of a genetically engineered clonal transformant cell directed to produce desired biomolecules, according to some embodiments. The method 220 can be partially or fully implemented using a strain generation system (e.g., system 100) described herein.

The method 220 includes at 221, assembly of desired DNA in liquid media. Target DNA fragments (e.g., DNA fragments coding for the production of biomolecules) can be assembled and/or prepared in any suitable manner to be introduced into a host cell.

The method 220 includes at 223, introduction of the assemble or prepared foreign DNA into a genome of a host cell, using liquid media. In some instances, known amounts and/or concentrations of the DNA fragments can be introduced into host cells of non-sporulating filamentous fungi (e.g., protoplasts) that are selected to be receptive to genetic manipulations. In some instances, the introduction of foreign DNA can be into a plurality of protoplasts, wherein the protoplasts were prepared from a culture of filamentous fungal cells.

The introduction of DNA into the host cell can be performed through any suitable method. In some implementations, the introduction of assemble DNA can be via transformation of the host cell to obtain engineered transformant cell in a transformation output in liquid media. The host cells undergo transformation to incorporate the foreign DNA into the genome of the host cells at specified loci. In some implementations, the host cells can be the plurality of protoplasts and the transforming of the plurality of protoplasts can include a first construct and a second construct. The first construct can include a first polynucleotide flanked on both sides by nucleotides homologous to a first locus in the genome of the protoplast and the second construct can include a second polynucleotide flanked on both sides by nucleotides homologous to a second locus in the genome of the protoplast, wherein the transformation results in integration of the first construct into the first locus and the second construct into the second locus by homologous recombination, wherein at least the second locus is a first selectable marker gene in the protoplast genome, and wherein the first polynucleotide comprises mutation and/or a genetic control element.

At 225, the method 220 includes high-throughput one-to-many transfer of transformation outputs in liquid media to a series of selection plates. The high-throughput one-to-many transfer can be done automatically using liquid handlers, such as the liquid handling system 108 of the system 100 described herein. In some instances, the transformation outputs can be diluted such that the one-to-many transfer can be conducted to accomplish separation and isolation of transformants in the wells in the selection plates. This can maximize the likelihood of obtaining growth outputs in the selection plates wherein clonal populations are obtained from single transformants. The identity of the single transformant may be used to select strains. For example, strains arising from homokaryotic transformants having all alleles are altered or manipulated at specified loci to include foreign DNA may be preferred over heterokaryotic strains to maximize industrial production of a desired biomolecule.

At 227, the method 220 includes isolation of single clonal transformants in liquid media from the selection plates. In some instances, the isolation of single clonal transformants can be directed to purifying homokaryotic transformants by performing selection and counter-selection. The transformation plates can be evaluated and transformation outputs resulting in growth derived from a single transformant can be identified.

At 229, the method 220 includes growing purified transformants in media conducive to regeneration of the filamentous fungal cells. The selection plates can be evaluated and clonal populations arising from a single transformant can be identified. The clonal populations that are most desirable (e.g., clonal populations of non-sporulating filamentous fungi that arise from a single transformant and in some instances from homokaryotic transformants) can be selected.

In some implementations, the plurality of protoplasts described above are distributed in wells of a microtiter plate. In some implementations, the plurality of transformation outputs described above are distributed in wells of a microtiter plate. In some implementations, the plurality of growth outputs described above are distributed in wells of a microtiter plate. In some implementations, one or more of the steps of the method 220 are performed in wells of a microtiter plate. In some cases, the microtiter plate is a 96 well, 384 well or 1536 well microtiter plate.

In some cases, the filamentous fungal cells are selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some instances, the filamentous fungal cells are from a strain found to be non-sporulating, partially sporulating, poorly sporulating, and/or unpredictably sporulating. In some cases, the filamentous fungal cells are from a strain found to be sporulating, but the methods and system described herein are used to circumvent the need for sporulation (e.g., to contain air-borne spores).

In some cases, the filamentous fungal cells are *Aspergillus niger*. In some cases, the filamentous fungal cells possess a non-mycelium forming phenotype. In some cases, wherein the fungal cell possesses a non-functional non-homologous end joining (NHEJ) pathway. In some cases, the NHEJ pathway is made non-functional by exposing the cell to an antibody, a chemical inhibitor, a protein inhibitor, a physical inhibitor, a peptide inhibitor, or an anti-sense or RNAi molecule directed against a component of the NHEJ pathway. In some cases, the chemical inhibitor is W-7.

In some cases, the first locus is for the target filamentous fungal gene. In some cases, the first locus is for a second selectable marker gene in the protoplast genome. In some cases, the second selectable marker gene is selected from an auxotrophic marker gene, a colorimetric marker gene or a directional marker gene. In some cases, the first selectable marker gene is selected from an auxotrophic marker gene, a colorimetric marker gene or a directional marker gene. In some cases, the second polynucleotide is selected from an auxotrophic marker gene, a directional marker gene or an antibiotic resistance gene. In some cases, the colorimetric marker gene is an aygA gene. In some cases, the auxotrophic marker gene is selected from an argB gene, a trpC gene, a pyrG gene, or a met3 gene. In some cases, the directional marker gene is selected from an acetamidase (amdS) gene, a nitrate reductase gene (niaD), or a sulphate permease (Sut B) gene. In some cases, the antibiotic resistance gene is a ble gene, wherein the ble gene confers resistance to pheomycin. In some cases, the first selectable marker gene is an aygA gene and the second polynucleotide is a pyrG gene. In some cases, the first selectable marker gene is a met3 gene, the second selectable marker gene is an aygA gene and the second polynucleotide is a pyrG gene.

In some cases, the plurality of protoplasts is prepared by removing cell walls from the filamentous fungal cells in the culture of filamentous fungal cells; isolating the plurality of protoplasts; and resuspending the isolated plurality of protoplasts in a mixture comprising dimethyl sulfoxide (DMSO), wherein the final concentration of DMSO is 7% v/v or less. In some cases, the mixture is stored at least −20° C. or −80° C. prior to performing the steps of the method 220. In some cases, the culture is grown for at least 12 hours prior to preparation of the protoplasts. In some cases, the fungal culture is grown under conditions whereby at least 70% of the protoplasts are smaller and contain fewer nuclei. In some cases, removing the cell walls is performed by enzymatic digestion. In some cases, the enzymatic digestion is performed with mixture of enzymes comprising a beta-glucanase and a polygalacturonase. In some cases, the method further comprises adding 40% v/v polyethylene glycol (PEG) to the mixture comprising DMSO prior to storing the protoplasts. In some cases, the PEG is added to a final concentration of 8% v/v or less. In some cases, one or more steps of the method 220 are partially or fully automated.

FIGS. 2B, 2C, and 2D describe various steps involved in FIG. 2B depicts an example workflow directed to a DNA building phase, that is the DNA assembly involved in generating an engineered cell, according to some embodiments. The example workflow in FIG. 2B describes the steps for building DNA fragments and cloning the DNA fragments. FIG. 2C depicts an example workflow directed to a strain building phase including transformation steps of strain generation, according to some embodiments. The example workflow in FIG. 2C described preparing and transforming the assembled DNA fragments into host filamentous fungal strains, and looping out selection sequences through counter selection. FIG. 2D depicts an example workflow directed to a colony growing phase, according to some embodiments. The example workflow in FIG. 2D describes colony growing steps including high-throughput culturing, screening, and evaluation of selected host filamentous fungal strains.

In some embodiments, the present disclosure is compatible with all genetic design and cloning methods. That is, in some embodiments, the present disclosure teaches the use of traditional cloning techniques such as polymerase chain reaction, restriction enzyme digestions, ligation, homologous recombination, RT PCR, and others generally known in the art and are disclosed in for example: Sambrook et al. (2001) Molecular Cloning: A Laboratory Manual ($3^{rd}$ ed., Cold Spring Harbor Laboratory Press, Plainview, N.Y.), incorporated herein by reference.

In some embodiments, the cloned sequences can include possibilities from any of the HTP genetic design libraries taught herein, for example: promoters from a promoter swap library, SNPs from a SNP swap library, start or stop codons from a start/stop codon exchange library, terminators from a STOP swap library, or sequence optimizations from a sequence optimization library. Further, the exact sequence combinations that should be included in a particular construct can be informed by the epistatic mapping function. In some embodiments, the cloned sequences can also include sequences based on rational design (hypothesis-driven) and/or sequences based on other sources, such as scientific publications.

In some embodiments, the present disclosure teaches methods of directed engineering, including the steps of i) generating custom-made SNP-specific DNA, ii) assembling SNP-specific constructs, iii) transforming target host cells with SNP-specific DNA, and iv) looping out any selection markers.

An example general workflow the strain engineering methods of the present disclosure, can include acquiring and assembling DNA, assembling any necessary vectors, transforming host cells and removing selection markers.

Build Specific DNA Oligonucleotides

In some embodiments, the systems and methods disclosed herein can be used with gene manipulation techniques such as inserting and/or replacing and/or altering and/or deleting a DNA segment of the host cell organism. In some aspects, the methods taught herein involve building an oligonucleotide of interest (i.e. a target DNA segment), that will be incorporated into the genome of a host organism. In some embodiments, the target DNA segments of the present disclosure can be obtained via any method known in the art, including: copying or cutting from a known template, mutation, or DNA synthesis. In some embodiments, the present disclosure is compatible with commercially available gene synthesis products for producing target DNA sequences (e.g., GeneArt™, GeneMaker™, GenScript™, Anagen™, Blue Heron™, Entelechon™, GeNOsys, Inc., or Qiagen™).

In some embodiments, the target DNA segment is designed to incorporate a SNP into a selected DNA region of the host organism (e.g., adding a beneficial SNP). In other embodiments, the DNA segment is designed to remove a SNP from the DNA of the host organisms (e.g., removing a detrimental or neutral SNP).

In some embodiments, the oligonucleotides used in the inventive methods can be synthesized using any of the methods of enzymatic or chemical synthesis known in the art. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648).

A great number of advances have been achieved in the traditional four-step phosphoramidite chemistry since it was first described in the 1980s (see for example, Sierzchala, et al. *J. Am. Chem. Soc.,* 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., *Nucleosides, Nucleotides, and Nucleic Acids,* 24 (5-7), 1037-1041 (2005) for improved synthesis of longer oligonucleotides through the use of large-pore CPG; and Damha et al., *NAR,* 18, 3813-3821 (1990) for improved derivatization).

Regardless of the type of synthesis, the resulting oligonucleotides may then form the smaller building blocks for longer oligonucleotides. In some embodiments, smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA, oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligonucleotides that are homologous to the forward strand at the 5' end of the gene and against the reverse strand at the 3' end of the gene.

Another method of synthesizing a larger double stranded DNA fragment is to combine smaller oligonucleotides through top-strand PCR (TSP). In this method, a plurality of oligonucleotides spans the entire length of a desired product and contain overlapping regions to the adjacent oligonucleotide(s). Amplification can be performed with universal forward and reverse primers, and through multiple cycles of amplification a full-length double stranded DNA product is formed. This product can then undergo optional error correction and further amplification that results in the desired double stranded DNA fragment end product.

In one method of TSP, the set of smaller oligonucleotides that will be combined to form the full-length desired product are between 40-200 bases long and overlap each other by at least about 15-20 bases. For practical purposes, the overlap region should be at a minimum long enough to ensure specific annealing of oligonucleotides and have a high enough melting temperature ($T_m$) to anneal at the reaction temperature employed. The overlap can extend to the point where a given oligonucleotide is completely overlapped by adjacent oligonucleotides. The amount of overlap does not seem to have any effect on the quality of the final product. The first and last oligonucleotide building block in the assembly should contain binding sites for forward and reverse amplification primers. In one embodiment, the terminal end sequence of the first and last oligonucleotide contain the same sequence of complementarity to allow for the use of universal primers.

Assembling DNA Fragments/Cloning Custom Plasmids

In some embodiments, the present disclosure teaches methods for constructing DNA fragments capable of inserting desired target DNA sections (e.g. containing a particular SNP) into the genome of host organisms DNA recombination methods can be used for increasing variation in diversity pools. DNA sections, such as genome regions from related species, can be cut via physical or enzymatic/chemical means. The cut DNA regions are melted and allowed to reanneal, such that overlapping genetic regions prime polymerase extension reactions. Subsequent melting/extension reactions are carried out until products are reassembled into chimeric DNA, comprising elements from one or more starting sequences and a promoter. A general scheme can include design, generate, assemble, QC, transform, loop-out and QC process for a SNPswap. It should be noted that this scheme can be applied to other HTP tools as provided herein (e.g., PROswp, STOPswp). In some embodiments, the systems and methods in present disclosure are compatible with methods of generating linear DNA fragments comprising the target DNA, homology arms, and at least one selection marker.

In some embodiments, the systems and methods in the present disclosure are compatible with any method suited for transformation of DNA fragments into the host organism (e.g., filamentous fungus such as *A. niger*). In some embodiments, the present disclosure teaches use of plasmids or assembly vectors for which a desired target DNA section can be cloned into and amplified therefrom. When used, the assembly vectors can further comprise any origins of replication that may be needed for propagation in a host cell yeast and/or *E. coli*). In certain instances, the target DNA can be inserted into vectors, constructs or plasmids obtainable from any repository or catalogue product, such as a commercial vector (see e.g., DNA2.0 custom or GATEWAY® vectors). In certain instances, the target DNA can be inserted into vectors, constructs or plasmids obtainable from any repository or catalogue product, such as a commercial vector (see e.g., DNA2.0 custom or GATEWAY® vectors). The use of plasmids for generating linear DNA fragments for ultimately transforming a host cell such as a filamentous fungus host cell can entail synthesizing parts of a target DNA construct comprising a desired gene to be integrated into a host genome, transforming a yeast cell with the parts of the target DNA construct along with an assembly vector, isolating the assembled plasmids containing the target DNA construct from said transformed yeast cell, propagating the isolated plasmids in *E. coli*, and PCR amplifying the target DNA construct from *E. coli* to generate a linear DNA fragment comprising a desired gene to be integrated into a host genome prior to transformation of the filamentous fungal host cell.

In some embodiments, assembly or generation of a linear DNA fragment(s) comprising a desired gene to be integrated into a host genome (e.g., filamentous fungal cell) can entail using fusion PCR. Fusion PCR can be performed using any fusion PCR method known in the art including, for example, the method described in Yu et al, Fungal Genetics and Biology, vol 41, pages 973-981 (2004), which is herein incorporated by reference in its entirety. For example, some embodiments of the disclosed methods can use fusion PCR to generate two linear DNA fragments that comprise a marker gene (i.e., pyrG split between them. Conceptually, fusion PCR can be used to generate any of the constructs comprising target gene mutations and/or selectable markers genes provided herein.

The linear DNA fragments for use in the methods provided herein can comprise markers for selection and/or counter-selection as described herein. The markers can be any markers known in the art and/or provided herein. The linear DNA fragments can further comprise any regulatory sequence(s) provided herein. The regulatory sequence can be any regulatory sequence known in the art or provided herein such as, for example, a promoter, start, stop, signal, secretion and/or termination sequence used by the genetic machinery of the host cell (e.g., non-sporulating filamentous fungal cell).

In some embodiments, the assembly/cloning methods of the present disclosure may employ at least one of the following assembly strategies: i) type II conventional cloning, ii) type II S-mediated or "Golden Gate" cloning (see, e.g., Engler, C., R. Kandzia, and S. Marillonnet. 2008 "A one pot, one step, precision cloning method with high-throughput capability". PLos One 3: e3647; Kotera, I., and T. Nagai. 2008 "A high-throughput and single-tube recombination of crude PCR products using a DNA polymerase inhibitor and type IIS restriction enzyme." J Biotechnol 137: 1-7; Weber, E., R. Gruetzner, S. Werner, C. Engler, and S. Marillonnet. 2011 Assembly of Designer TAL Effectors by Golden Gate Cloning. PloS One 6: e19722), iii) GATE-WAY® recombination, iv) TOPO® cloning, exonuclease-mediated assembly (Aslanidis and de Jong 1990. "Ligation-independent cloning of PCR products (LIC—PCR)." Nucleic Acids Research, Vol. 18, No. 20 6069), v) homologous recombination, vi) non-homologous end joining, vii) Gibson assembly (Gibson et al., 2009 "Enzymatic assembly of DNA molecules up to several hundred kilobases" Nature Methods 6, 343-345) or a combination thereof. Modular type IIS based assembly strategies are disclosed in PCT Publication WO 2011/154,147, the disclosure of which is incorporated herein by reference.

In some embodiments, the present disclosure can involve methods using cloning vectors with at least one selection marker. Various selection marker genes are known in the art often encoding antibiotic resistance function for selection in prokaryotic (e.g., against ampicillin, kanamycin, tetracycline, chloramphenicol, zeocin, spectinomycin/streptomycin) or eukaryotic cells (e.g. geneticin, neomycin, hygromycin, puromycin, blasticidin, zeocin) under selective pressure. Other marker systems allow for screening and identification of wanted or unwanted cells such as the well-known blue/white screening system used in bacteria to select positive clones in the presence of X-gal or fluorescent reporters such as green or red fluorescent proteins expressed in successfully transduced host cells. Another class of selection markers most of which are only functional in prokaryotic systems relates to counter selectable marker genes often also referred to as "death genes" which express toxic gene products that kill producer cells. Examples of such genes include sacB, rpsL (strA), tetAR, pheS, thyA, gata-1, or ccdB, the function of which is described in (Reyrat et al. 1998 "Counterselectable Markers: Untapped Tools for Bacterial Genetics and Pathogenesis." Infect Immun. 66(9): 4011-4017).

An example workflow associated with DNA assembly can include 4 stages: parts generation, plasmid/construct assembly, plasmid/construct QC, and plasmid/construct preparation for transformation. During parts generation, oligos designed by Laboratory Information Management System (LIMS) are ordered from an oligo sequencing vendor and used to amplify the target sequences from the host organism via PCR. These PCR parts are cleaned to remove contaminants and assessed for success by fragment analysis, in silico quality control comparison of observed to theoretical fragment sizes, and DNA quantification. In some embodiments, the parts are transformed into yeast along with an assembly vector and assembled into plasmids via homologous recombination. Assembled plasmids are isolated from yeast and transformed into a separate yeast host cell for subsequent assembly quality control and amplification. During plasmid assembly quality control, several replicates of each plasmid are isolated, amplified using Rolling Circle Amplification (RCA), and assessed for correct assembly by enzymatic digest and fragment analysis. Correctly assembled plasmids identified during the QC process are hit picked to generate permanent stocks and the specific gene construct including any flanking sequences necessary to facilitate genome integration are then PCR amplified from the plasmid to generate linear DNA fragments that are quantified and QC'd via fragment analysis prior to transformation into the target host organism (e.g., non-sporulating filamentous fungal host cell). In some embodiments, the parts are subjected to fusion PCR to generate linear DNA fragments, which are QC'd via fragment and sequence analysis prior to transformation into the target host organism (e.g., filamentous fungal host cell).

Protoplasting Methods

In some embodiments, the methods and systems provided herein involve the generation of protoplasts from coenocytic organisms (e.g., filamentous fungal cells). Suitable procedures for preparation of protoplasts can be any known in the art including, for example, those described in EP 238,023 and Yelton et al. (1984, Proc. Natl. Acad. Sci. USA 81: 1470-1474). In one embodiment, protoplasts are generated by treating a pre-cultivated culture of filamentous fungal cells with one or more lytic enzymes or a mixture thereof. The lytic enzymes can be a beta-glucanase and/or a poly-galacturonase. In one embodiment, the enzyme mixture for generating protoplasts is VinoTaste concentrate. Many of the parameters utilized to pre-cultivate cultures of coenocytic organisms (e.g., filamentous fungal cells) and subsequently generate and utilize protoplasts therefrom for use in the methods and compositions provided herein can be varied. For example, there can be variations of inoculum size, inoculum method, pre-cultivation media, pre-cultivation times, pre-cultivation temperatures, mixing conditions, washing buffer composition, dilution ratios, buffer composition during lytic enzyme treatment, the type and/or concentration of lytic enzyme used, the time of incubation with lytic enzyme, the protoplast washing procedures and/or buffers, the concentration of protoplasts and/or polynucleotide and/or transformation reagents during the actual transformation, the physical parameters during the transformation, the procedures following the transformation up to the obtained transformants. In some cases, these variations can be utilized to optimize the number of protoplasts and the transformation efficiency. In one embodiment, the coenocytic organism is a filamentous fungal cell as provided herein (e.g., A. niger). Further to this embodiment, the pre-cultivation media can be YPD or complete media. The volume of pre-cultivation media can be at least, at most or about 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml or 1000 ml. The volume of pre-cultivation media can be from about 50 ml to about 100 ml, about 100 ml to about 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to about 500 ml, about 500 ml to about 550 ml, about 550 ml to about 600 ml, about 600 ml to about 650 ml, about 650 ml to about 700 ml, about 700 ml to about 750 ml, about 750 ml to about 800 ml, about 800 ml to about 850 ml, about 850 ml to about 900 ml, about 900 ml to about 950 ml or about 950 ml to about 1000 ml. In some cases, a plurality of cultures are cultivated and subsequently subjected to protoplasting. The plurality of cultures can be 2, 3, 4, 5, 6, 7, 8, 9, 10, 12, 14, 16, 18, 20, 25, 50, 75, 100, 150, 200, 300, 400, 500 or more. In one embodiment, a pre-cultivation preparation is prepared by inoculating 100 ml of rich media (e.g., YPD or complete media) with $10^6$ transformants/ml and incubating the pre-cultivation preparation between 14-18 hours at 30° C. In another embodiment, a pre-cultivation preparation is prepared by inoculating 500 ml of rich media (e.g., Yeast Mold Broth, YPD or complete media) with at least $10^6$ transformants/ml and incubating the pre-cultivation preparation between 14-18 hours at 30° C. Prior to protoplasting, the coenocytic organism can be isolated by any method known in the art such as, for example centrifugation. In one embodiment, the coenocytic organism is filamentous fungus (e.g., A. niger). Further to this embodiment, Yeast Mold Broth (YMB) is inoculated with $10^6$ transformants/ml of the filamentous fungal cells and grown for 16 hours at 30° C. Further still to this embodiment, the filamentous fungal cells grown in the precultivation preparation can be isolated by centrifugation. The pre-cultivation preparations provided herein for use in the methods and compositions provided herein can produce an amount of hyphae for subsequent protoplasting of about, at least or more than 0.5 g, 1 g, 1.5 g, 2 g, 2.5 g, 3 g, 3.5 g, 4 g or 5 g of wet weight. Pre-cultivation/cultivation of the coenocytic organism (e.g., filamentous fungus) can be part of a workflow in a high-throughput system (HTP). The HTP system can be automated or semi-automated. Pre-cultivation of the organism can entail inoculating a small scale volume (e.g., 100 ml) of sporulation media (PDAmedia) with $10^6$ transformants/ml of the organism (e.g., A. niger) and growing for 14-16 hours at 30° C. During pre-cultivation, the workflow can contain a step whereby an enzyme solution for generating protoplasts from the pre-cultivated organism (e.g., A. niger) is generated. The enzyme solution can consist of Vinotaste pro (Novozymes) enzyme mix in phosphate buffer comprising 1.2 M $MgSO_4$. Following pre-cultivation, hyphae can be collected following filtration through a Miracloth and a large-scale culture can be cultivated by inoculating about 500 ml of complete media in a 2.8 L flask with 10 ul to 20 ml of the collected hyphae. Inoculum size can be variable based on the OD of the culture obtained from the pre-cultivation step. The large scale culture can be grown for 6-18 hours at either 30° C. or 18° C. at 80% humidity with shaking at 200 rpms. Following cultivation, the culture(s) can be isolated by centrifugation following by one or more washes and resuspended. In one embodiment, the cultures are resuspended in a protoplasting buffer as described herein and subjected to protoplasting as described herein. Centrifugation can be performed in 500 ml centrifuge tubes at 4° C. for 10-15 minutes at 5500-6100× g. Each of the one or more washes can be performed in 10-50 ml of wash buffer (e.g., water with 10% glycerol) followed by centrifugation at 4° C. for 10-15 minutes at 5500-6100× g.

Following isolation as described above, the coenocytic organism (e.g., filamentous fungal cells such as A. niger) can be resuspended in protoplasting buffer such that the protoplasting buffer comprises one or enzymes as provided herein (e.g., VinoTaste pro concentrate (Novozymes)) for generating protoplasts. In one embodiment, the protoplasting buffer has a high concentration of osmolite (e.g., greater than or equal to 1 M of an osmolite such as $MgSO_4$). In embodiments utilizing a protoplasting buffer with a high osmolite concentration (e.g., 1.2 M $MgSO_4$), the incubation time for the enzymatic treatment (e.g., VinoTaste pro concentrate (Novozymes)) can be from about 14-16 hours at about 30° C. The volume of protoplasting buffer used for resuspension can be 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml or 1000 ml. The volume of protoplasting buffer used for resuspension can be can be from about 50 ml to about 100 ml, about 100 ml to about 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to about 500 ml, about 500 ml to about 550 ml, about 550 ml to about 600 ml, about 600 ml to about 650 ml, about 650 ml to about 700 ml, about 700 ml to about 750 ml, about 750 ml to about 800 ml, about 800 ml to about 850 ml, about 850 ml to about 900 ml, about 900 ml to about 950 ml or about 950 ml to about 1000 ml. In one embodiment, filamentous fungal cells are grown in 500 ml of rich media (e.g., YPD or complete media) and hyphae (can be about 1 g wet mass) are isolated by filtration through a Miracloth, rinsing with 100 ml of wash buffer (e.g., 100 mM sodium phosphate buffer with 1.2 M $MgSO_4$, pH 5.5) and resuspended in about 500 ml of protoplasting buffer (e.g., 100 mM sodium phosphate buffer with 1.2 M $MgSO_4$ pH 5.5) comprising a protoplasting enzyme mixture (e.g., VinoTaste pro concentrate (Novozymes)) in a 1 L bottle. The hyphae in the enzyme solution can be incubated for 14-16 hours at 30° C. with shaking at 140 rpm with continued monitoring of protoplast formation via microscopic examination.

In one embodiment, one or more chemical inhibitors of the NHEJ pathway are added to a protoplasting buffer as provided. The one or more chemical inhibitors can be selected from W7, chlorpromazine, vanillin, Nu7026, Nu7441, mirin, SCR7, AG14361 or any combination thereof. Addition of the one or more chemical inhibitors to the protoplasting buffer can occur at any point during the protoplasting procedure. In one embodiment, treatment with the one or more chemical inhibitors is for the entire protoplasting procedure. In a separate embodiment, treatment with the one or more chemical inhibitors is for less than the entire protoplasting procedure. Treatment with the one or more chemical inhibitors can be for about 1, 5, 10, 15, 20, 30, 45, 60, 90, 120, 150, 180, 210, 240, 270 or 300 minutes. In one embodiment, the co-enocytic cells (e.g., filamentous fungal cells) are treated with W-7. In another embodiment, the co-enocytic cells (e.g., filamentous fungal cells) are treated with SCR-7.

Following enzymatic treatment, the protoplasts can be isolated using methods known in the art. Prior to isolation of protoplasts, undigested hyphal fragments can be removed by filtering the mixture through a porous barrier (such as Miracloth) in which the pores range in size from 20-100 microns in order to produce a filtrate of filtered protoplasts. In some embodiments, the filtered protoplasts are then centrifuged at moderate levels of centripetal force to cause the protoplasts to pellet to the bottom of the centrifuge tube.

The centripetal force can be from about 500-1500× g. In some embodiments, the centripetal force used is generally below 1000× g (e.g., 800× g for 5 minutes). In some embodiments, a buffer of substantially lower osmotic strength is gently applied to the surface of the protoplasts (e.g., filtered protoplasts) following generation of protoplasts in a protoplasting buffer comprising a high concentration of osmolite. Examples of buffers of substantially lower osmotic strength include buffers (e.g., Tris buffer) comprising 1 M Sorbitol, 1 M NaCl, 0.6 M Ammonium Sulfate or 1 M KCl. In some embodiments, the lower osmotic strength buffer for use in the methods provided herein is a Sorbitol-Tris (ST) buffer that comprises 0.4 M sorbitol and has a pH of 8. This layered preparation can then be centrifuged, which can cause the protoplasts to accumulate at a layer in the tube in which they are neutrally buoyant. Protoplasts can then be isolated from this layer for further processing (e.g., storage and/or transformation). In yet another embodiment, the protoplasts (e.g., filtered protoplasts) generated in a protoplasting buffer comprising a high concentration of osmolite (e.g., 100 mM phosphate buffer comprising 1.2 M $MgSO_4$, pH 5.5) are transferred to an elongated collection vessel (e.g., graduated cylinder) and a buffer of lower osmolarity as provided herein (e.g., 0.4 M ST buffer, pH 8) is overlaid on the surface of the protoplasts (e.g., filtered protoplasts) to generate a layer at which the protoplasts are neutrally buoyant. The combination of the buffers of differing osmolarity in the elongated collection vessel (e.g., graduated cylinder) can facilitate the protoplasts 'floating' to the surface of the elongated collection vessel (e.g., graduated cylinder). Once at the top of the collection vessel, the protoplasts can be isolated. In one embodiment, a 500 ml pre-cultivation preparation of coenocytic organisms (e.g., filamentous fungal cells such as *A. niger*) grown and subjected to protoplasting as provided herein yields about 25 ml of protoplasts.

Following protoplast isolation, the remaining enzyme containing buffer can be removed by resuspending the protoplasts in an osmotic buffer (e.g., 1 M sorbitol buffered using 10 mM TRIS, pH 8) and recollected by centrifugation. This step can be repeated. After sufficient removal of the enzyme containing buffer, the protoplasts can be further washed in osmotically stabilized buffer also containing Calcium chloride (e.g., 1 M sorbitol buffered using 10 mM TRIS, pH 8, 50 mM $CaCl_2$)) one or more times.

Following isolation and washing, the protoplasts can be resuspended in an osmotic stabilizing buffer. The composition of such buffers can vary depending on the species, application and needs. However, typically these buffers contain either an organic component like sucrose, citrate, mannitol or sorbitol between 0.5 and 2 M. More preferably between 0.75 and 1.5 M; most preferred is 1 M. Otherwise these buffers contain an inorganic osmotic stabilizing component like KCl, $(NH_4)_2SO_4$, $MgSO_4$, NaCl or $MgCl_2$ in concentrations between 0.1 and 1.5 M. Preferably between 0.2 and 0.8 M; more preferably between 0.3 and 0.6 M, most preferably 0.4 M. The most preferred stabilizing buffers are STC (sorbitol, 0.8 M; $CaCl_2$, 25 mM; Tris, 25 mM; pH 8.0) or KCl-citrate (KCl, 0.3-0.6 M; citrate, 0.2% (w/v)). The protoplasts can be used in a concentration between $1\times10^5$ and $1\times10^{10}$ cells/ml or between $1-3\times10^7$ protoplasts per ml. Preferably, the concentration is between $1\times10^6$ and $1\times10^9$; more preferably the concentration is between $1\times10^7$ and $5\times10^8$; most preferably the concentration is $1\times10^8$ cells/ml. To increase the efficiency of transfection, carrier DNA (as salmon sperm DNA or non-coding vector DNA) may be added to the transformation mixture. DNA is used in a concentration between 0.01 and 10 ug; preferably between 0.1 and 5 ug, even more preferably between 0.25 and 2 ug; most preferably between 0.5 and 1 ug.

In one embodiment, following generation and subsequent isolation and washing, the protoplasts are mixed with one or more cryoprotectants. The cryoprotectants can be glycols, dimethyl sulfoxide (DMSO), polyols, sugars, 2-Methyl-2,4-pentanediol (MPD), polyvinylpyrrolidone (PVP), methylcellulose, C-linked antifreeze glycoproteins (C-AFGP) or combinations thereof. Glycols for use as cryoprotectants in the methods and systems provided herein can be selected from ethylene glycol, propylene glycol, polypropylene glycol (PEG), glycerol, or combinations thereof. Polyols for use as cryoprotectants in the methods and systems provided herein can be selected from propane-1,2-diol, propane-1,3-diol, 1,1,1-tris-(hydroxymethyl)ethane (THME), and 2-ethyl-2-(hydroxymethyl)-propane-1,3-diol (EHMP), or combinations thereof. Sugars for use as cryoprotectants in the methods and systems provided herein can be selected from trehalose, sucrose, glucose, raffinose, dextrose or combinations thereof. In one embodiment, the protoplasts are mixed with DMSO. DMSO can be mixed with the protoplasts at a final concentration of at least, at most, less than, greater than, equal to, or about 1%, 2%, 3%, 4%, 5%, 6%, 7%, 8%, 9%, 10%, 12.5%, 15%, 20%, 25%, 30%, 35%, 40%, 45%, 50%, 55%, 60%, 65%, 70%, or 75% w/v or v/v. The protoplasts/cryoprotectant (e.g., DMSO) mixture can be distributed to microtiter plates prior to storage. The protoplast/cryoprotectant (e.g., DMSO) mixture can be stored at any temperature provided herein for long-term storage (e.g., several hours, day(s), week(s), month(s), year(s)) as provided herein such as, for example −20° C. or −80° C. In one embodiment, an additional cryoprotectant (e.g., PEG) is added to the protoplasts/DMSO mixture. In yet another embodiment, the additional cryoprotectant (e.g., PEG) is added to the protoplast/DMSO mixture prior to storage. The PEG can be any PEG provided herein and can be added at any concentration (e.g., w/v or v/v) as provided herein. In one embodiment, the PEG solution is prepared as 40% w/v in STC buffer. 20% v/v of this 40% PEG-STC can then be added to the protoplasts. For example, 800 microliters of $1.25\times10^7$ protoplasts would have 200 microliters of 40% PEG-STC giving a final volume of 1 ml. Seventy microliters of DMSO can then be added to this 1 ml to bring this prep to 7% v/v DMSO.

Any pre-cultivation, cultivation and/or protoplasting protocol provided herein can be performed in a high-throughput manner. For example, pre-cultivation, cultivation and protoplasting can be performed as part of a workflow such that said workflow represents a portion of a high-throughput (HTP) protocol or workflow. The high-throughput protocol can utilize automated liquid handling for any and/or all steps.

Transformation of Host Cells

In some embodiments, the vectors or constructs of the present disclosure may be introduced into the host cells (e.g., filamentous fungal cells or protoplasts derived therefrom) using any of a variety of techniques, including transformation, transfection, transduction, viral infection, gene guns, or Ti-mediated gene transfer (see Christie, P. J., and Gordon, J. E., 2014 "The *Agrobacterium* Ti Plasmids" Microbiol SPectr. 2014; 2(6); 10.1128). Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include, for example, lithium acetate transformation and electroporation see, e.g., Gietz et al., Nucleic Acids Res. 27: 69-74 (1992); Ito et al., J. Bacterol. 153: 163-168 (1983); and Becker and Guarente, Methods in Enzymology 194: 182-187 (1991). In some embodiments, transformed host cells are referred to as recombinant host strains.

In some embodiments, the present disclosure teaches high-throughput transformation of cells using the 96-well plate robotics platform and liquid handling machines of the present disclosure.

In one embodiment, the methods and systems provided herein are compatible with the transfer of nucleic acids to protoplasts derived from filamentous fungal cells as described herein. In another embodiment, the transformation utilized by the methods and systems provided herein is high-throughput in nature and/or is partially or fully automated as described herein. The partially or fully automated method can entail the use of automated liquid handling one or more liquid handling steps as provided herein. Further to this embodiment, the transformation is performed by adding constructs or expression constructs as described herein to the wells of a microtiter plate followed by aliquoting protoplasts generated by the methods provided herein to each well of the microtiter plate. Suitable procedures for transformation/transfection of protoplasts can be any known in the art including, for example, those described in international patent applications PCT/NL99/00618, PCT/EP99/202516, Finkelstein and Ball (eds.), Biotechnology of filamentous fungi, technology and products, Butterworth-Heinemann (1992), Bennett and Lasure (eds.) More Gene Manipulations in fungi, Academic Press (1991), Turner, in: Puhler (ed), Biotechnology, second completely revised edition, VHC (1992) protoplast fusion, and the Ca-PEG mediated protoplast transformation as described in EP635574B. Alternatively, transformation of the filamentous fungal host cells or protoplasts derived therefrom can also be performed by electroporation such as, for example, the electroporation described by Chakraborty and Kapoor, Nucleic Acids Res. 18: 6737 (1990), *Agrobacterium tumefaciens*-mediated transformation, biolistic introduction of DNA such as, for example, as described in Christiansen et al., Curr. Genet. 29: 100 102 (1995); Durand et al., Curr. Genet. 31: 158 161 (1997); and Barcellos et al., Can. J. Microbiol. 44: 1137 1141 (1998) or "magneto-biolistic" transfection of cells such as, for example, described in U.S. Pat. Nos. 5,516,670 and 5,753,477. In one embodiment, the transformation procedure used in the methods and systems provided herein is one amendable to being high-throughput and/or automated as provided herein such as, for example, PEG mediated transformation.

Transformation of the protoplasts generated using the methods described herein can be facilitated through the use of any transformation reagent known in the art. Suitable transformation reagents can be selected from Polyethylene Glycol (PEG), FUGENE® HD (from Roche), Lipofectamine® or OLIGOFECTAMINE® (from Invitrogen), TRANSPASS® D1 (from New England Biolabs), LYPOVEC® or LIPOGEN® (from Invivogen). In one embodiment, PEG is the most preferred transformation/transfection reagent. PEG is available at different molecular weights and can be used at different concentrations. Preferably, PEG 4000 is used between 10% and 60%, more preferably between 20% and 50%, most preferably at 40%. In one embodiment, the PEG is added to the protoplasts prior to storage as described herein.

Looping Out of Selected Sequences

In some embodiments, the methods and systems provided herein are compatible with methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. In some embodiments, the present disclosure teaches looping out selection markers from positive transformants. Looping out deletion techniques are known in the art, and are described in (Tear et al. 2014 "Excision of Unstable Artificial Gene-Specific inverted Repeats Mediates Scar-Free Gene Deletions in *Escherichia coli*." Appl. Biochem. Biotech. 175: 1858-1867). The looping out methods used in the methods provided herein can be performed using single-crossover homologous recombination or double-crossover homologous recombination. In one embodiment, looping out of selected regions as described herein can entail using single-crossover homologous recombination as described herein.

First, loop out constructs are inserted into selected target regions within the genome of the host organism (e.g., via homologous recombination, CRISPR, or other gene editing technique). In one embodiment, double-crossover homologous recombination is used between a construct or constructs and the host cell genome in order to integrate the construct or constructs. The inserted construct or constructs can be designed with a sequence which is a direct repeat of an existing or introduced nearby host sequence, such that the direct repeats flank the region of DNA slated for looping-out and deletion. Once inserted, cells containing the loop out construct or constructs can be counter selected for deletion of the selection region (e.g., lack of resistance to the selection gene).

Persons having skill in the art will recognize that the description of the loopout procedure represents but one illustrative method for deleting unwanted regions from a genome. Indeed the methods of the present disclosure are compatible with any method for genome deletions, including but not limited to gene editing via CRISPR, TALENS, FOK, or other endonucleases. Persons skilled in the art will also recognize the ability to replace unwanted regions of the genome via homologous recombination techniques Constructs for Transformation In some embodiments, the methods and systems provided herein entail the transformation or transfection of filamentous fungal cells or protoplasts derived therefrom with at least one nucleic acid. The transformation or transfection can be using of the methods and reagents described herein. The generation of the protoplasts can be performed using any of the methods provided herein. The protoplast generation and/or transformation can be high-throughput and/or automated as described previously. The nucleic acid can be DNA, RNA or cDNA. The nucleic acid can be a polynucleotide. The nucleic acid or polynucleotide for use in transforming a filamentous fungal cell or protoplast derived therefrom using the methods and systems provided herein can be an endogenous gene or a heterologous gene relative to the variant strain and/or the parental strain. The endogenous gene or heterologous gene can encode a product or protein of interest as described herein. As described herein, the protein of interest can refer to a polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be expressed intracellularly or as a secreted protein. The endogenous gene or heterologous gene can comprise a mutation and/or be under the control of or operably linked to one or more genetic control or regulatory elements. The mutation can be any mutation provided herein such as, for example, an insertion, deletion, substitution and/or single nucleotide polymorphism. The one or more genetic control or regulatory elements can be a promoter sequence and/or a terminator sequence. The endogenous gene or heterologous gene can be present on one expression construct or split across multiple expression constructs. When split across multiple expression constructs, each portion of the endogenous gene or heterologous gene can comprise a mutation and/or be under the control of or operably linked to one or more genetic control or regulatory elements. In one embodiment, an endogenous gene or heterologous gene is bipartite, wherein said endogenous gene or heterologous gene is split into two portions such that each of said two portions is present on a separate construct. In one embodiment, the gene is FungiSNP_9 (SEQ ID NO: 11), FungiSNP_12 (SEQ ID NO: 12), FungiSNP_18 (SEQ ID NO: 13) or FungiSNP_40 (SEQ ID NO: 14). In another embodiment, the gene is FungiSNP_9 (SEQ ID NO: 11), FungiSNP_12 (SEQ ID NO: 12), FungiSNP_18 (SEQ ID NO: 13) or FungiSNP_40 (SEQ ID NO: 14) fused to or operably linked to any of the promoters from Table 1. In one embodiment, the gene is FungiSNP_18 (SEQ ID NO: 13). In another embodiment, the gene is FungiSNP_18 (SEQ ID NO: 13) fused to or operably linked to the man8p or amy8p promoter from Table 1.

The promoter sequence and/or terminator sequence can be endogenous or heterologous relative to the variant strain and/or the parental strain. Promoter sequences can be operably linked to the 5' termini of the sequences to be expressed. A variety of known fungal promoters are likely to be functional in the host strains of the disclosure such as, for example, the promoter sequences of C1 endoglucanases, the 55 kDa cellobiohydrolase (CBH1), glyceraldehyde-3-phosphate dehydrogenase A, C. lucknowense GARG 27K and the 30 kDa xylanase (Xy 1F) promoters from Chrysosporium, as well as the Aspergillus promoters described in, e.g. U.S. Pat. Nos. 4,935,349; 5,198,345; 5,252,726; 5,705,358; and 5,965,384; and PCT application WO 93/07277. In some embodiments, the promoters for use in the methods and systems provided herein are inducible promoters. The inducible promoters can be any promoter whose transcriptional activity is regulated by the presence or absence of a chemical such as for example, alcohol, tetracycline, steroids, metal or other compounds known in the art. The inducible promoters can be any promoter whose transcriptional activity is regulated by the presence or absence of light or low or high temperatures. In some embodiments, the inducible promoter is catabolite repressed by glucose such as, for example, the promoter for the *A. niger* amylase B gene. In some embodiments, the inducible promoters are selected from filamentous fungal genes such as the srpB gene, the amyB gene, the manB gene or the mbfA gene. In one embodiment, the inducible promoter is selected form the promoters listed in Table 1.

A non-exhaustive list of the promoters of the present disclosure is provided in the below Table 1. Each of the promoter sequences can be referred to as a heterologous promoter or heterologous promoter polynucleotide.

TABLE 3

Selected promoter sequences of the present disclosure.

| SEQ ID NO: | Promoter Short Name | Promoter Name |
|---|---|---|
| 1 | manBp | manB promoter from *Aspergillus niger* |
| 2 | amyBp | amyB gene from *Aspergillus oryzae* |
| 3 | srpBp | srpB promoter from *Aspergillus niger* |
| 4 | mbfAp | mbfA promoter from *Aspergillus niger* |

In some embodiments, the promoters of the present disclosure exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter from the above table 1.

Terminator sequences can be operably linked to the 3' termini of the sequences to be expressed. A variety of known fungal terminators are likely to be functional in the host strains of the disclosure. Examples are the *A. nidulans* trpC terminator, *A. niger* alpha-glucosidase terminator, *A. niger* glucoamylase terminator, *Mucor miehei* carboxyl protease terminator (see U.S. Pat. No. 5,578,463), *Chrysosporium* terminator sequences, e.g. the EG6 terminator, and the *Trichoderma reesei* cellobiohydrolase terminator. In one embodiment, the terminator sequences are direct repeats (DRs). In some embodiment, a transcriptional terminator sequence of the present disclosure can be selected from a terminator sequence listed in Table 4 or an orthologue of a termination sequence provided in Table 4. For example, if the host cell is an *Aspergillus*, the termination sequence can be an orthologue of a non-*Aspergillus* termination sequence selected from Table 4.

Persons having skill in the art will recognize that the methods of the present disclosure are compatible with any termination sequence. A non-exhaustive listing of transcriptional terminator sequences of the present disclosure is provided in Table 4 below. In one embodiment, a transcriptional terminator of the present disclosure can be an orthologue of a termination sequence provided in Table 4. For example, if the host cell is an *Aspergillus*, the termination sequence can be an orthologue of a non-*Aspergillus* termination sequence selected from Table 4.

TABLE 4

Non-exhaustive list of termination sequences of the present disclosure. Yeast and other Eukaryotes

| Name | Description | Direction | Length |
|---|---|---|---|
| BBa_J63002 | ADH1 terminator from *S. cerevisiae* | Forward | 225 |
| BBa_K110012 | STE2 terminator | Forward | 123 |
| BBa_K1462070 | cyc1 | | 250 |
| BBa_K1486025 | ADH1 Terminator | Forward | 188 |
| BBa_K392003 | yeast ADH1 terminator | | 129 |
| BBa_K801011 | TEF1 yeast terminator | | 507 |
| BBa_K801012 | ADH1 yeast terminator | | 349 |
| BBa_Y1015 | CycE1 | | 252 |
| BBa_J52016 | eukaryotic -- derived from SV40 early poly A signal sequence | Forward | 238 |
| BBa_J63002 | ADH1 terminator from *S. cerevisiae* | Forward | 225 |
| BBa_K110012 | STE2 terminator | Forward | 123 |
| BBa_K1159307 | 35S Terminator of Cauliflower Mosaic Virus (CaMV) | | 217 |

TABLE 4-continued

Non-exhaustive list of termination sequences of the present disclosure.
Yeast and other Eukaryotes

| Name | Description | Direction | Length |
|---|---|---|---|
| BBa_K1462070 | cyc1 | | 250 |
| BBa_K1484215 | nopaline synthase terminator | | 293 |
| BBa_K1486025 | ADH1 Terminator | Forward | 188 |
| BBa_K392003 | yeast ADH1 terminator | | 129 |
| BBa_K404108 | hGH terminator | | 481 |
| BBa_K404116 | hGH_[AAV2]-right-ITR | | 632 |
| BBa_K678012 | SV40 poly A, terminator for mammalian cells | | 139 |
| BBa_K678018 | hGH poly A, terminator for mammalian cells | | 635 |
| BBa_K678019 | BGH poly A, mammalian terminator | | 233 |
| BBa_K678036 | trpC terminator for *Aspergillus nidulans* | | 759 |
| BBa_K678037 | T1-motni, terminator for *Aspergillus niger* | | 1006 |
| BBa_K678038 | T2-motni, terminator for *Aspergillus niger* | | 990 |
| BBa_K678039 | T3-motni, terminator for *Aspergillus niger* | | 889 |
| BBa_K801011 | TEF1 yeast terminator | | 507 |
| BBa_K801012 | ADH1 yeast terminator | | 349 |
| BBa_Y1015 | CycE1 | | 252 |

In one embodiment, a protoplast generated from a filamentous fungal cell is co-transformed with two or more nucleic acids or polynucleotides. Further to this embodiment, at least one of the two or more polynucleotides is an endogenous gene or a heterologous gene relative to the filamentous fungal strain from which the protoplast was generated and at least one of the two or more polynucleotides is a gene for a selectable marker. The selectable marker gene can be any selectable marker as provided herein. As described herein, each of the two or more nucleic acids or polynucleotides can be split into separate portions such that each separate portion is present on a separate construct.

In one embodiment, each nucleic acid or polynucleotide for use in transforming or transfecting a non-sporulating filamentous fungal cell or protoplast derived therefrom comprises sequence homologous to DNA sequence present in a pre-determined target locus of the genome of the filamentous fungal cell or protoplast derived therefrom that is to be transformed on either a 5', a 3' or both a 5' and a 3' end of the nucleic acid or polynucleotide. The nucleic acid or polynucleotide can be an endogenous gene or heterologous gene relative to the filamentous fungal cell used for transformation or a selectable marker gene such that sequence homologous to a pre-determined locus in the filamentous fungal host cell genome flanks the endogenous, heterologous, or selectable marker gene. In one embodiment, each nucleic acid or polynucleotide is cloned into a cloning vector using any method known in the art such as, for example, pBLUESCRIPT® (Stratagene). Suitable cloning vectors can be the ones that are able to integrate at the pre-determined target locus in the chromosomes of the filamentous fungal host cell used. Preferred integrative cloning vectors can comprise a DNA fragment, which is homologous to the DNA sequence to be deleted or replaced for targeting the integration of the cloning vector to this pre-determined locus. In order to promote targeted integration, the cloning vector can be linearized prior to transformation of the host cell or protoplasts derived therefrom. Preferably, linearization is performed such that at least one but preferably either end of the cloning vector is flanked by sequences homologous to the DNA sequence to be deleted or replaced. In some cases, short homologous stretches of DNA may be added for example via PCR on both sides of the nucleic acid or polynucleotide to be integrated. The length of the homologous sequences flanking the nucleic acid or polynucleotide sequence to be integrated is preferably less than 2 kb, even preferably less, than 1 kb, even more preferably less than 0.5 kb, even more preferably less than 0.2 kb, even more preferably less than 0.1 kb, even more preferably less than 50 bp and most preferably less than 30 bp. The length of the homologous sequences flanking the nucleic acid or polynucleotide sequence to be integrated can vary from about 30 bp to about 1000 bp, from about 30 bp to about 700 bp, from about 30 bp to about 500 bp, from about 30 bp to about 300 bp, from about 30 bp to about 200 bp, and from about 30 bp to about 100 bp. The nucleic acids or polynucleotides for use in transforming filamentous fungal cells or protoplasts derived therefrom can be present as expression cassettes. In one embodiment, the cloning vector is pUC19. Further to this embodiment, a cloning vector containing a marker sequence as provided herein can be associated with targeting sequence by building the construct through using a Gibson assembly as known in the art. Alternatively, the targeting sequence can be added by fusion PCR. Targeting sequence for co-transformation that is not linked to a marker may be amplified from genomic DNA.

In theory, all loci in the filamentous fungal genome could be chosen for targeted integration of the expression cassettes comprising nucleic acids or polynucleotides provided herein. Preferably, the locus wherein targeting will take place is such that when the wild type gene present at this locus has been replaced by the gene comprised in the expression cassette, the obtained mutant will display a change detectable by a given assay such as, for example a selection/counterselection scheme as described herein. In one embodiment, the protoplasts generated from filamentous fungal cells as described herein are co-transformed with a first construct or expression cassette and a second construct or expression cassette such that the first construct or expression cassette is designed to integrate into a first locus of the protoplast genome, while the second construct or expression cassette is designed to integrate into a second locus of the protoplast genome. To facilitate integration into the first locus and second locus, the first construct or expression cassette is flanked by sequence homologous to the first locus, while the second construct or expression cassette is flanked by sequence homologous to the second locus. In one embodiment, the first construct or expression cassette comprises sequence for an endogenous gene, while the second construct comprises sequence for a selectable marker gene. Further to this embodiment, the second locus contains sequence for an additional selectable marker gene present in the protoplast genome used in the methods and systems provided herein, while the first locus contains sequence for the endogenous target gene present in the protoplast genome used in the methods and systems provided herein. In a separate embodiment, the first construct or expression cassette comprises sequence for an endogenous gene or a heterologous gene, while the second construct comprises sequence for a first selectable marker gene. Further to this separate embodiment, the second locus contains sequence for a second selectable marker gene that is present in the protoplast genome used in the methods and systems provided herein, while the first locus contains sequence for a third selectable marker gene that is present in the protoplast genome used in the methods and systems provided herein. In each of the above embodiments, the endogenous gene and/or heterologous gene can comprise a mutation (e.g., SNP) and/or a genetic control or regulatory element as provided herein.

Purification of Homokaryotic Protoplasts

Protoplasts derived from filamentous fungi can often contain more than one nucleus such that subsequent transformation with a construct (e.g., insert DNA fragment) as provided herein can produce protoplasts that are heterokaryotic such that the construct (e.g., insert DNA fragment) is incorporated into only a subset of the multiple nuclei present in the protoplast. In order to reduce the number or percentage of heterokaryotic protoplasts following transformation, strategies can be employed to increase the percentage of mononuclear protoplasts in a population of protoplasts derived from filamentous fungal host cells prior to transformation such as, for example, using the method described in Roncero et al., 1984, Mutat. Res. 125: 195, the contents of which are herein incorporated by reference in its entirety.

In some embodiments, the systems and methods disclosed herein can be used for evaluating and isolating clonal populations derived from individual transformants by circumventing the need for spore formation. In some cases, the individual transformants can be incapable of sporulation. The individual transformants are suspended in liquid media. The methods for isolating the clonal populations derived from the individual transformants can facilitate or aid in the isolation of homokaryotic fungal strains following genetic perturbation using any of the methods provided herein. Further to this embodiment, a plurality of transformation outputs (e.g., transformation outputs derived from filamentous fungal cells or strains) can be diluted to generate a liquid suspension of individual transformants and discrete volumes of the liquid suspension can be placed or distributed into the wells or reaction areas of a substrate such as, for example, a microtiter plate. The microtiter plate can be a 96 well, 384 well or 1536 well plate.

In order to achieve a high statistical probability that each reaction area or well in the microtiter plate contains either a single individual fungal transformant or no fungal transformant, the resuspended plurality of transformants can be diluted to a specified degree (e.g., 1×/2, 1×/5, 1×/10, 1×/20, 1×/25, 1×/100, etc., and all possible dilutions therebetween). In one embodiment, the dilution is such that the suspension of transformant is at a concentration whereby the probability that a dispensed or discrete volume of the suspension contains either one or no transformant follows a Poisson Distribution. Further to this embodiment, approximately 50% of the wells will contain no transformants and thus be empty. Of the remaining wells, greater than 90%, 91%, 92%, 93%, 94%, 95%, 96%, 97%, 98%, 99% or 99.5% will have a single cell, and less than 2%, 1%, 0.5% or 0% will have 2 or more cells. Dispensing of the suspension of transformants can be accomplished using any of the liquid handling devices provided herein (see Table 2) and/or known in the art.

In some embodiments, following resuspension and dilution of the plurality of transformants, discrete volumes of the suspension can be screened for the presence or absence of single individual fungal transformants in the discrete volume. Further to this embodiment, if a discrete volume of the suspension contains only a single individual fungal transformant, that discrete volume is distributed, placed or dispensed into a well or reaction areas also referred to herein as growth area. The screening can be performed using any of the single cell/transformant dispensing devices provided herein (see Table 2) and/or known in the art. In one embodiment, the device optically identifies single cells or transformants. The device can be a FACS device, a CellenONE device, a Cytena Single Cell Printer or a Berkeley Lights Beacon device. Prior to resuspension and/or dilution, the plurality of individual fungal transformants can be picked or isolated using any of the devices provided herein (see Table 2) and/or known in the art. The resuspension and dilution of the transformants can be accomplished using any of the devices provided herein (see Table 2) and/or known in the art.

Following the screening for the presence or absence of single individual fungal transformants in the discrete volume, the methods described herein for distributing or dispensing individual transformants to the wells or growth areas of a substrate comprising wells or reaction/growth areas can result in at least 70%, 75%, 80%, 85%, 90%, 95%, 99 or 99.5% of the wells or growth areas in the substrate containing a single individual viable transformant from a plurality of transformants. Using the methods described herein for distributing individual transformants to the wells or reaction/growth areas of a substrate comprising wells or reaction areas can result in greater than 70%, 75%, 80%, 85%, 90%, 95%, 99 or 99.5% of the wells or growth/reaction areas in the substrate containing a single individual viable transformant from a plurality of transformant. Using the methods described herein for distributing individual transformants to the wells or growth/reaction areas of a substrate comprising wells or growth/reaction areas can result in substantially all of the wells or growth/reaction areas in the substrate containing a single individual viable transformant from a plurality of transformants. Using the methods described herein for distributing individual transformants to the wells or growth/reaction areas of a substrate comprising wells or growth/reaction areas can result in all or 100% of the wells or growth/reaction areas in the substrate containing a single individual viable transformant from a plurality of transformants. Using the methods described herein for distributing individual transformant to the wells or growth/reaction areas of a substrate comprising wells or reaction areas can result in a statistical probability that greater than or at least 70%, 75%, 80%, 85%, 90%, 95%, 99 or 99.5% of the wells in the microtiter plate contain a single individual viable transformant. Using the methods described herein for distributing individual transformant to the wells or growth/reaction areas of a substrate comprising wells or growth/reaction areas can result in a statistical probability that all or substantially all of the wells in the microtiter plate contain a single individual viable transformant. The substrate can be a microtiter plate. The microtiter plate can be a 96 well, 384 well or 1536 well plate.

The plurality of individual fungal transformants can be derived from a filamentous fungal strain. The filamentous fungal strain can be selected from but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some embodiments, the filamentous fungal strain is included in the phylum Ascomycota. In some embodiments, the filamentous fungal strain is included in the phylum Basidiomycota. In some embodiments, the filamentous fungal strain is a Basidiomycete that may be capable of sporulation but requires a stage of mushroom formation in order to make spores. Such a requirement can be incompatible with high-throughput methods in genetic engineering. Genetic engineering of such Basidiomycetes using methods and systems described herein, by circumventing sporulation, can permit high-throughput manipulation of the strain. In some embodiments, the filamentous fungal strain is *Aspergillus niger*. In some embodiments, the filamentous fungal strain possesses a non-mycelium forming phenotype. In some embodiments, the filamentous fungal strain possesses a non-functional non-homologous end joining (NHEJ) pathway. The NHEJ pathway can be made non-functional by exposing the cell to an antibody, a chemical inhibitor, a protein inhibitor, a physical inhibitor, a peptide inhibitor, or an anti-sense or RNAi molecule directed against a component of the NHEJ pathway.

The liquid used for resuspending the plurality of individual transformants can be culture media or a buffer. Further, the wells or growth/reaction areas can comprise selective media that can serve to select transformants having a specific genetic perturbation such that culturing the distributed individual fungal transformants in the growth/reaction areas or wells comprising media selective for the genetic variation facilitates identification and selection of colonies derived from an individual transformants that contained the desired genetic perturbation.

Aside from or in addition to employing strategies to increase the number or percentage of mononuclear protoplasts prior to transformation, strategies can be employed to drive protoplasts (and the colonies derived therefrom following regeneration of said protoplasts) to being homokaryotic post-transformation regardless of whether they are mono- or multinucleate. As provided herein, increasing the number or percentage of protoplasts (and the colonies derived therefrom) that are homokaryotic for a desired or target gene of interest can entail subjecting the colonies derived from the transformed protoplast or population of transformed protoplasts to selection and/or counter-selection based on the presence and/or absence of one or more selectable markers. The one or more selectable markers can be any selectable marker or combination of selectable markers as provided herein and the selection and/or counter-selection scheme can any such scheme as provided herein.

Identification of Homokaryotic Transformants

Homokaryotic transformants produced by the methods provided herein can be identified through the use of phenotypic screening, sequence-based screening or a combination thereof. In other words, phenotypic screening, sequence-based screening or a combination thereof can be used to detect the presence or absence of a parental genotype in a colony derived from a protoplast following transformation of said protoplast with a construct (e.g., insert DNA fragment). Identification or detection of homokaryotic transformants can occur before and/or following subjecting said transformants to a selection and/or counter-selection scheme as provided herein in keeping with the introduction and/or loss of one or more selectable marker genes. Phenotypic screening can be used to identify a transformant with a discernable phenotype (change in growth and/or colorimetric change), while sequence-based screening can be used to identify transformants with or without a discernable phenotype following transformation and integration of a construct or constructs as provided herein.

Sequence-Based Screening

As described herein, sequence-based screening can be used to determine the presence or absence of a desired or target construct in a transformant. In this manner, sequence-based sequencing can be used to assess whether or not integration of a desired gene or construct has occurred in a specific transformant. Sequence-based screening can be used to determine the percentage of nuclei in a multinucleate cell or population of multinucleate cells that contain a desired gene, mutation or construct. Further, sequence-based screening can be used to determine the percentage of a population of transformants that has experienced a desired target integration. The construct can be any construct, or a plurality of constructs as described herein. In some cases, the results of sequence-based screening can be used to select purification schemes (e.g., homokaryotic purification) if the percentage or ratio of nuclei comprising a desired gene, mutation or construct vs. nuclei lacking said desired gene, mutation or construct is below a certain threshold.

In general, sequence-based screening can entail isolating transformants that may contain a desired mutation or construct. Each transformant may contain one or a plurality of nuclei such that the one or each of the plurality of the nuclei contain fragments of nucleic acid (e.g., one or more constructs or genes comprising a mutation) introduced during transformation. The transformation can be targeted transformations of protoplasts with specific fragments of DNA (e.g., one or more constructs or genes comprising a mutation) as provided herein.

In some cases, following isolation, sequence-based screening entails propagating the transformants that contain a mixture of nuclei with both the target gene (introduced construct) and the wild-type or parental gene on media that impacts the purity of the target gene (i.e., selective media) or may be completely non-selective for any particular phenotype or trait, thereby generating colonies derived from the transformants. In one embodiment, each isolated transformant or a portion of a colony derived therefrom is transferred to or placed in a well of a microtiter plate such as, for example, an Omnitray comprising agar wherein the transformant or a portion of a colony derived therefrom sporulate. The microtiter plate can be a 96 well, 384 well or 1536 well microtiter plate.

Following isolation alone or in combination with propagation, nucleic acid (e.g., DNA) can be extracted from the transformant or colonies derived therefrom. Nucleic acid isolation can be from transformants derived from transformation outputs and can be performed in a microtiter plate format and can utilize automated liquid handling. Extraction of the nucleic acid can be performed using any known nucleic acid extraction method known in the art and/or commercially available kit such as for example Prepman™ (ThermoFischer Scientific). In one embodiment, nucleic acid extracted from transformants derived from transformation outputs is performed using a boil prep method that allows for amplification of DNA. The boil prep method can include the inoculation of transformants into a small amount of growth media. In one embodiment, the transformants are separated into 96 wells in a plate suitable for PCR wherein each well comprises the small amount of growth media. The transformants can be allowed to grow for between 10 and 16 hours, which can help the transformants discard potential components (e.g., pigments) that may inhibit PCR. Additionally, the growth can also facilitate several rounds of nuclear division which can serve to increase the genomic DNA content of each well. Subsequently, the overnight "mini cultures" can then be supplemented with a buffer that assists in cell lysis as well as stabilizes the DNA that will be released during lysis. One example of a suitable buffer can be PrepMan Ultra (Thermo Fisher). Other examples of suitable buffers can include Tris buffered solutions that contain a small amount of ionic detergent. The min-culture-buffer mixtures can then be heated in a thermocycler to 99 degrees C. for any of a range of incubation times of between 15 minutes and 1 hour.

Following nucleic acid extraction, sequence-based screening can be performed to assess the percentage or ratio of target or mutant nuclei comprising an introduced target gene or construct to parent nuclei (i.e., non-transformed nuclei). The sequence-based screening can be any method known in the art that can be used to determine or detect the sequence of a nucleic acid. The method used to perform sequence-based screening can be selected from nucleic acid sequencing methods or hybridization-based assays or methods. The nucleic acid sequencing assay or technique utilized by the methods provided herein can be a next generation sequencing (NGS) system or assay. The hybridization based assay for detecting a particular nucleic acid sequence can entail the use of microarrays or the nCounter system (Nanostring). Prior to conducting sequence-based screening, the extracted nucleic acid can be amplified using PCR with primer pair(s) directed to the target gene.

In embodiments utilizing nucleic acid sequencing methodologies, the primer pairs utilized in the PCR can comprise adapter sequences that can be subsequently used in a secondary amplification using coded indexing primers. Amplicons generated by the secondary amplification reaction can then be sequenced using multiplex sequencing with sequencing primers directed to the coded indexed primers. The sequencing can be performed using any type of sequencing known in the art. In one embodiment, the sequencing is next generation sequencing (NGS). The NGS can be any known NGS method known in the art such as, for example, Illumina NGS. Data from the multiplex sequencing reactions can then be used to determine the presence or absence of the target nuclei. In some cases, the data from the multiplex sequencing reactions can also be used to determine the ratio of parental nuclei to mutant nuclei for a transformant within the target well. Further to this embodiment, a standard curve can be generated in order to quantify the percentage or ratio of parent to mutant nuclei. The standard curve can be generated by amplifying and sequencing nucleic acid isolated from strains containing known ratios of a parent to mutant nuclei such and subsequently using the ratio of parent to mutant amplicons that appear in the known ratio to determine an approximation of the purity of a test sample. The strains used to generate the standard curve can be processed (e.g., isolated, propagated and extracted) in the same set of plates as the test sample.

In one embodiment, sequence-based sequencing is used following selection and/or counter-selection in order to assess or determine the homokaryotic status of each transformant. Sequence-based sequencing post selection and/or counter-selection can use multiplex sequencing as described herein and can be automated or semi-automated. Sequence-based sequencing post selection and/or counter-selection can also utilize generation of a standard curve as described herein as means of determining the presence and/or amount (e.g., ratio) a transformant is heterokaryotic.

Use of Sequence-Based Screening to Determine Purity of Transformants

As discussed herein, protoplasts generated from coenocytic host cells (e.g., filamentous fungal host cells) in the methods, systems and workflows provided herein can be multinucleate. Subsequently, protoplasts transformed with one or more constructs such as those provided herein can contain only a portion or percentage of their multiple nuclei with a particular construct or constructs integrated into their genome. Depending on the nature of the transformed constructs, colonies derived from the transformed protoplast may not produce a discernable phenotype due to the presence of the mixed population of nuclei present in the colony. Accordingly, the use of sequence-based screening can be essential for determining the percentage of the nuclei in a mixed population of nuclei that contain a desired construct or constructs vs. those that do not contain a desired construct or constructs. In one embodiment, NGS based screening is used to identify transformants or strains derived therefrom that contain a desired percentage of nuclei with an introduced construct or constructs. The desired percentage can be a threshold percentage, whereby transformants or strains derived therefrom at or above said threshold percentage produce a desired product of interest or level thereof. The product of interest can be selected from a product listed in Table 1. The desired percentage can be 50%, 55%, 60%, 65%, 70%, 75%, 80%, 85%, 90%, 95%, 99% or 100%. The percentage can be determined by utilizing a standard curve as described herein.

Phenotypic Screening

As described herein, phenotypic screening can be used in combination with sequence-based screening or transformants. In some cases, the results of sequence-based screening can be used to determine purification schemes in order to ensure the isolation of homokaryotic transformants. Further, sequence-based screening can be utilized following phenotypic screening/purification in order to assess if the isolates obtained by phenotypic screening/purification are homokaryotic.

Phenotypic screening of transformants generated using the methods, compositions or systems provided herein can employ the use of one or more selectable markers. A selectable marker can often encode a gene product providing a specific type of resistance foreign to the non-transformed strain. This can be resistance to heavy metals, antibiotics or biocides in general. Prototrophy can also be a useful selectable marker of the non-antibiotic variety. Auxotrophic markers can generate nutritional deficiencies in the host cells, and genes correcting those deficiencies can be used for selection.

There is a wide range of selection markers in use in the art and any or all of these can be applied to the methods and systems provided herein. The selectable marker genes for use herein can be auxotrophic markers, prototrophic markers, dominant markers, recessive markers, antibiotic resistance markers, catabolic markers, enzymatic markers, fluorescent markers, luminescent markers or combinations thereof. Examples of these include, but are not limited to: amdS (acetamide/fluoroacetamide), ble (belomycin-phleomycin resistance), hyg (hygromycinR), nat (nourseotricin R), pyrG (uracil/5FOA), niaD (nitrate/chlorate), sutB (sulphate/selenate), eGFP (Green Fluorescent Protein) and all the different color variants, aygA (colorimetric marker), met3 (methionine/selenate), pyrE (orotate P-ribosyl transferase), trpC (anthranilate synthase), argB (ornithine carbamoyltransferase), bar (phosphinothricin acetyltransferase), mutant acetolactate synthase (sulfonylurea resistance), and neomycin phosphotransferase (aminoglycoside resistance).

In one embodiment, a single selection marker is used for examining the phenotypic effects of a specific mutation of a target gene in the genome of a coenocytic organism. The coenocytic organism can be a filamentous fungi such as *A. niger*. The target gene can be a gene involved in a biosynthetic pathway such as, for example, a gene involved in citric acid production. An example of this type of embodiment can include a deletion construct comprising a pyrG gene flanked by sequence homologous to a gene involved in citric acid production in *A. niger*. This gene is introduced into a host protoplast comprising a version of the citric acid production gene comprising a mutation (e.g., SNP) and lacking a native pyrG gene. Homologous recombination of the pyrG construct generates transformants that can be selected for based on the presence of pyrG gene. Further, transformants can have a deletion phenotype that can be used to inform about the role said mutation plays in the pathway. Alternatively, in some embodiments, a construct comprising a gene involved in citric acid production with a specific mutation (e.g., SNP) flanked by sequence homologous to the native pyrG locus in the host protoplast is introduced into the host protoplast. Homologous recombination between the construct and the native pyrG locus can generate transformants that can be selected for by growing said transformants on media comprising FOA. The phenotypic effects of the introduced SNP can then be assessed as described herein.

Another embodiment of the present disclosure entails the use of two or more selection markers active in filamentous fungi. There is a wide range of combinations of selection markers that can be used and all of these can be applied in the selection/counterselection scheme provided herein. For example, the selection/counterselection scheme can utilize a combination of auxotrophic markers, prototrophic markers, dominant markers, recessive markers, antibiotic resistance markers, catabolic markers, enzymatic markers, fluorescent markers, and luminescent markers. A first marker can be used to select in the forward mode (i.e., if active integration has occurred), while additional markers can be used to select in the reverse mode (i.e., if active integration at the right locus has occurred). Selection/counterselection can be carried out by co-transformation such that a selection marker can be on a separate vector or can be in the same nucleic acid fragment or vector as the endogenous or heterologous gene as described herein.

In one embodiment, the homokaryotic protoplast purification scheme of the present disclosure entails co-transforming protoplasts generated form filamentous fungal host cells with a first construct comprising sequence for an endogenous gene or heterologous gene and a second construct comprising sequence for a first selectable marker gene such that the first construct is directed to a first locus of the protoplast genome that comprises sequence for a target gene to be removed or inactivated, while the second construct is directed to a second locus of the protoplast genome that comprises sequence for a second selectable marker gene. In one embodiment, the first construct comprises sequence for an endogenous gene or heterologous gene and the target gene to be removed or inactivated is for a third selectable marker gene. In a separate embodiment, the first construct comprises a sequence for an endogenous gene and the target gene to be removed or inactivated is the copy of the endogenous gene present in the genome of the protoplast prior to transformation. As described herein, the endogenous gene or heterologous gene of the first construct can comprise a mutation (e.g., SNP) and/or a genetic regulatory or control element (e.g., promoter and/or terminator). The first, second and/or third selectable marker can be any auxotrophic markers, prototrophic markers, dominant markers, recessive markers, antibiotic resistance markers, catabolic markers, enzymatic markers, fluorescent markers, luminescent markers known in the art and/or described herein. To be directed to a specific locus each of the constructs is flanked by nucleotides homologous to the desired locus in the protoplast genome as described herein.

An example embodiment where a first construct comprising sequence for an endogenous gene or heterologous gene and the target gene to be removed or inactivated is for a third selectable marker gene is contemplated. In this example, the first construct comprises sequence for an endogenous gene involved in citric acid production in filamentous fungus that comprises a SNP that is integrated into the locus for the colorimetric selectable marker gene aygA, while the second construct comprises sequence for the auxotrophic marker gene pyrG that is integrated into the locus for the auxotrophic marker gene met3. In this example, the filamentous fungal host cell is pyrG negative or uracil auxotrophic. Accordingly, purification of homokaryotic protoplast transformants entails growing said transformants on minimal media lacking uracil. Homokaryotic transformants will not only be uracil prototrophs, but will also be pure yellow in color, indicting incorporation of the pyrG gene and removal of the aygA gene. Counterselection and removal of any residual heterokaryotic colonies can be accomplished by subsequently plating the transformants on minimal media (with or without uracil) that contains selenate, whereby transformants with met3+ nucleic will die in the presence of selenate. Another marker that operates similarly to the met3 gene can be, for example, the niaA gene encoding nitrate reductase, which can be used in the selection/counterselection scheme described in this embodiment. For the niaA gene, the filamentous fungal host cells can be niaA+, whereby correct integration of the second construct generates niaA-progeny which are resistant to chlorate used during counterselection. In one embodiment, confirmation of correct integration of the first and/or second construct into the protoplast genome is confirmed by sequencing the genome of the protoplast using such as, for example next generation sequencing (NGS).

An example of the embodiment where the first construct comprises a sequence for an endogenous gene and the target gene to be removed or inactivated is the copy of the endogenous gene present in the genome of the protoplast prior to transformation is contemplated. In this example, the first construct comprises sequence for an endogenous gene involved in citric acid production in filamentous fungus that comprises a SNP that is integrated into the locus for said endogenous gene lacking said SNP, while the second construct comprises sequence for the auxotrophic marker gene pyrG that is integrated into the locus for the colorimetric marker gene aygA. In this example, the filamentous fungal host cell is pyrG negative or uracil auxotrophic. Accordingly, purification of homokaryotic protoplast transformants entails growing said transformants on minimal media lacking uracil. Homokaryotic transformants will not only be uracil prototrophs, but will also be pure yellow in color, indicting incorporation of the pyrG gene and removal of the aygA gene. In one embodiment, confirmation of correct integration of the first and/or second construct into the protoplast genome is confirmed by sequencing the genome of the protoplast using such as, for example next generation sequencing (NGS). The NGS system or method used can be any NGS system or method known in the art such as for example Illumina NGS.

In one embodiment, the second construct comprises an expression cassette that encodes a recyclable or reversible marker. The recyclable or reversible marker can be a disruption neo-pyrG-neo expression cassette. The neo-pyrG-neo construct can be co-transformed with the first construct as described in the above embodiments in a ura-strain of filamentous fungal host cell (e.g., *A. niger*) and homokaryotic transformants can be selected by plating on uracil deficient medium and selecting pure yellow uracil prototrophs as described above. Subsequently, use of pyrG selection can be regenerated by plating said homokaryotic transformants on 5-FOA containing medium and selecting transformants that grow on said 5-FOA medium, which indicates that said transformants have undergone an intrachromosomal recombination between the neo repeats that results in excision of the pyrG gene.

In a further embodiment, instead of using co-transformation as provided herein, the homokaryotic protoplast purification scheme of the present disclosure entails transforming protoplasts generated form filamentous fungal host cells with a deletion construct comprising sequence for a specific gene such that the construct is directed to a desired locus of the protoplast genome that comprises sequence for a target gene to be removed or inactivated. To be directed to a specific locus the constructs is flanked by nucleotides homologous to the desired locus in the protoplast genome as described herein. Use of this type of construct/transformation can be used to provide information on the role a particular gene plays in a particular biochemical pathway. In one embodiment, confirmation of correct integration of the deletion construct into the protoplast genome is confirmed by sequencing the genome of the protoplast using such as, for example next generation sequencing (NGS). The NGS system or method used can be any NGS system or method known in the art such as for example Illumina NGS. In one case, the filamentous fungal host cell is pyrG negative and the deletion construct comprises a selectable marker gene (e.g., pyrG gene), while the target gene is a SNP. Accordingly, purification of homokaryotic protoplast transformants entails growing said transformants on minimal media lacking uracil. In another case, the filamentous fungal host cell is pyrG positive and the deletion construct comprises a SNP, while the target gene is a selectable marker gene (e.g., pyrG gene). Accordingly, purification of homokaryotic protoplast transformants entails growing said transformants on minimal media comprising FOA.

In yet another embodiment, a mutated gene (e.g., a SNP) is integrated into a target locus in the genome of a coenocytic organism (e.g., filamentous fungi such as *A. niger*) via transformation and integration of multiple portions of the mutated gene such that each of the multiple portions of the mutated gene are present on a separate construct. Each of the multiple constructs can comprise a unique portion of the mutated gene plus an overlapping portion of the mutated gene that is also present on one of the other multiple constructs in order to facilitate recombination of the multiple constructs to produce a functional copy of the mutated gene in the organism's genome. To facilitate integration of each portion of the mutated gene into the desired locus of the organism, each of the multiple constructs can further comprise nucleotides homologous to the desired locus in the organism's genome that flank the portion of the mutated gene in the construct. In some cases, the mutated gene is split across two constructs and is introduced into the organism via bipartite transformation of the two constructs. One example of this concept includes the pyrG marker gene being split into two constructs such that each of the constructs comprises a unique portion of the pyrG and a portion that overlaps with the other construct. Further, each construct further comprises sequence homologous to the aygA marker gene in the host organism genome such that each of the portion of homologous sequence in the two construct also contains a SNP. Recombination of the two constructs following transformation using any of the methods provided herein results in insertion of a the whole pyrG marker gene comprising the two SNPs. Transformants containing the wholly integrated pyrG marker gene and transformants who have lost the pyrG marker gene via loop-out can be detected via selection/counterselection as described herein. In particular, loop-outs can be selected by growing the transformants on media with FOA.

A further example of bipartite transformation includes an example of a combinatorial SNPSWP in fungi (e.g., *A. niger*) whereby multiple mutations of a target gene (i.e., aygA gene) are introduced into a protoplast genome by the integration into the parental aygA gene of two separate constructs each comprising a mutation and a portion of a split marker gene (divergent pyrG genes) in a single transformation. Upon successful recombination between the overlapping portions of the respective pyrG gene containing constructs and between the homologous portions of the aygA gene in the constructs and host genome, expression of each of the whole pyrG genes can be controlled via catabolite repression by glucose. Accordingly, transformants can be selected by growing the transformants on glucose such that the growth of transformants in which the desired recombination and integration events have occurred will be favored. Further, loop-outs can be facilitated by growing the transformants on media with FOA. As can be understood by one skilled in the art, the concepts described herein can be used to introduce combinations of mutations (e.g., SNPs) into a target gene and subsequently test the phenotypic effects of said combination. The phenotypic effect can be generation of a desired property or activity of an exogenous protein. The property or activity of interest can mean any physical, physicochemical, chemical, biological, or catalytic property, or any improvement, increase, or decrease in such a property, associated with the exogenous protein. The phenotypic effect can also be the production or lack of production of one or more metabolites. The phenotypic effect can also be increased or decreased quantities of a protein or metabolite. Further, it is contemplated that further mutations can be introduced using a similar technique in order to build strains containing specific combinations of mutations.

Additional approaches that can be used in the methods and systems provided herein for generating transformants with targeted integration of mutations in a target gene are contemplated. In one embodiment, co-transformation of a coenocytic organism (e.g., filamentous fungi) is performed using a first construct comprising sequence homologous to a desired locus in the host organism genome, a target gene with a mutation (e.g., SNP) and a portion of marker gene (e.g., pyrG) flanked by a terminator repeat (e.g., direct repeat (DR)) and a second construct comprising an overlapping portion of the marker gene on the first construct as well as the remainder of the marker gene flanked by a second terminator repeat (DR) and sequence homologous to the desired locus in the host organism genome. Transformants comprising successful recombination of the constructs and integration into the desired locus can be isolated using any of the selection/counterselection schemes provided herein (e.g., aygA based selection and loss of pyrG counterselection). An example of integration of a mutation (e.g., SNP) in a target gene (e.g., aygA) using a loop-in single crossover event with a construct comprising a copy of the target gene with a mutation and one or more selectable markers (e.g., antibiotic resistance gene ($amp^R$) and auxotrophic marker gene (pyrG)) can be used.

Library Generation

A further aspect of the disclosure can include the construction and screening of fungal mutant libraries, and fungal mutant libraries prepared by the methods disclosed herein. The fungal libraries can be incorporated into platform for building fungal strains. The libraries may be obtained by transformation of the fungal hosts according to this disclosure with any means of integrative transformation, using methods known to those skilled in the art. A library of fungi based on the preferred host strains generated using the methods and systems provided herein may be handled and screened for desired properties or activities of exogenous proteins in miniaturized and/or high-throughput format screening methods. Property or activity of interest can mean any physical, physicochemical, chemical, biological, or catalytic property, or any improvement, increase, or decrease in such a property, associated with an exogenous protein of a library member. The library may also be screened for metabolites, or for a property or activity associated with a metabolite, produced as a result of the presence of exogenous and/or endogenous proteins. The library may also be screened for fungi producing increased or decreased quantities of such protein or metabolites.

In one embodiment, the methods and systems provided herein generate a plurality of protoplasts such that each protoplast from the plurality of protoplasts is transformed with a single first construct from a plurality of first constructs and a single second construct from a plurality of second constructs. Further to this embodiment, a first polynucleotide in each first construct from the plurality of first constructs comprises a different mutation and/or genetic control or regulatory element while a second polynucleotide in each second construct from the plurality of second constructs is identical. The method further comprises transforming and purifying homokaryotic transformants using selection/counterselection as described herein two or more times in order to generate a library of filamentous fungal cells such that each filamentous fungal cell in the library comprises a first polynucleotide with a different mutation and/or genetic control or regulatory element. In one embodiment, the first polynucleotide comprises sequence for a target filamentous fungal gene or a heterologous gene comprising a mutation such that the iterative process generates a library of filamentous fungal cells upon regeneration of the protoplasts such that each member of the library comprises a target filamentous fungal gene or a heterologous gene with a distinct mutation. As described herein, the first polynucleotide can be split between more than one construct such that each construct can comprise an overlapping portion of the first polynucleotide in order to facilitate homologous recombination between the constructs when introduced into a host organism. Further, each construct comprising an overlapping portion of the first polynucleotide can further comprise sequence homologous to a desired locus in the host genome in order to facilitate integration of the recombined first polynucleotide into the desired locus. In one embodiment, the mutation is a SNP and the methods thereby produces a SNPSwap library. In one embodiment, the target filamentous fungal gene is a gene involved in citric acid production and the plurality of first constructs is the library of SNPs provided in Table 4. In another embodiment, the first polynucleotide comprises sequence for a target filamentous fungal gene or a heterologous gene operably linked to a genetic control or regulatory element such that the iterative process described herein generates a library of filamentous fungal cells upon regeneration of the protoplasts such that each member of the library comprises a target filamentous fungal gene or a heterologous gene operably linked to a distinct genetic control or regulatory element. In one embodiment, the genetic control or regulatory element is a promoter and the methods thereby produce a Promoter or PRO library. In one embodiment, the genetic control or regulatory element is a terminator and the methods thereby produce a Terminator or STOP library. The promoter and/or terminator sequence can be a promoter or terminator sequence provided herein and/or known in the art for expression in a filamentous fungal host cells used in the methods and systems provided herein. In one embodiment, the promoter is an inducible promoter.

TABLE 4

SNPs potentially involved in citric acid production in *A. niger*.

| Mutation name | Location | Sequence change | Orientation | Contig | Description | SNP in Coding Domain | Morphological Phenotype |
|---|---|---|---|---|---|---|---|
| FungiSNP_01 | 50669-680224 | ~>~ | 680224 | chr_1_1 | | | |
| FungiSNP_02 | 1172974 | G > A | + | chr_1_1 | Aromatic amino acid aminotransferase and related protein | X | |
| FungiSNP_03 | 367948 | C > T | + | chr_1_2 | | | |
| FungiSNP_04 | 549014 | C > G | − | chr_1_2 | | | |
| FungiSNP_05 | 1330718 | G > A | + | chr_1_2 | | | |
| FungiSNP_06 | 662258 | G> | + | chr_2_1 | Taurine catabolism dioxygenase TauD/TfdA | X | |
| FungiSNP_07 | 673547 | G > A | − | chr_2_1 | alpha/beta hydrolase | X | |
| FungiSNP_08 | 946654 | T> | + | ch_2_1 | | | |
| FungiSNP_09 | 641661 | T > A | − | chr_2_2 | pseudouridylate synthase activity | X | X |
| FungiSNP_10 | 2316591 | G > A | + | chr_2_2 | | | |
| FungiSNP_11 | 935908 | A > G | − | chr_3_1 | Serine/threonine protein kinase | X | |
| FungiSNP_12 | 205638 | T > A | + | chr_3_2 | Transcription factor | X | X |
| FungiSNP_13 | 268107 | T > C | + | chr_3_3 | | | |
| FungiSNP_14 | 186943 | A > T | + | chr_3_4 | | | |

TABLE 4-continued

SNPs potentially involved in citric acid production in *A. niger*.

| Mutation name | Location | Sequence change | Orientation | Contig | Description | SNP in Coding Domain | Morphological Phenotype |
|---|---|---|---|---|---|---|---|
| FungiSNP_15 | 276232 | C > T | + | chr_3_4 | | | |
| FungiSNP_16 | 1287891 | T > C | − | chr_4_1 | Serine/threonine protein kinase | X | |
| FungiSNP_17 | 1639965 | A > T | + | chr_4_1 | | | |
| FungiSNP_18 | 1826343 | G > A | − | chr_4_1 | Sensory transduction histidine kinase | X | X |
| FungiSNP_19 | 1358794 | C > A | + | chr_4_2 | | | |
| FungiSNP_20 | 1466380 | CTA> | + | chr_4_2 | mannitol-1-phosphate 5-dehydrogenase | X | |
| FungiSNP_21 | 1700330 | C > A | − | chr_4_2 | Tomosyn and related SNARE-interacting protein | X | |
| FungiSNP_22 | 2873296 | A > G | + | chr_4_2 | | | |
| FungiSNP_23 | 815022 | G > A | + | chr_5_2 | unknown function | X | |
| FungiSNP_24 | 831672 | G > A | − | chr_5_2 | Cytochrome c heme-binding site | X | |
| FungiSNP_25 | 1507652 | >A | + | chr_5_2 | | | |
| FungiSNP_26 | 442488 | T > C | + | chr_6_1 | | | |
| FungiSNP_27 | 93202-103239 | ~>~ | + | chr_6_2 | | | |
| FungiSNP_28 | 972833 | A > T | + | chr_6_2 | | | |
| FungiSNP_29 | 972932 | A> | + | chr_6_2 | | | |
| FungiSNP_30 | 1183094 | G> | + | chr_6_2 | Monooxygenase involved in coenzyme Q (ubiquinone) biosynthesis | X | |
| FungiSNP_31 | 1701762 | T > G | + | chr_6_2 | | | |
| FungiSNP_32 | 236406 | G > A | − | chr_7_1 | extracellular unknown protein | X | |
| FungiSNP_33 | 2350056 | A> | + | chr_7_1 | | | |
| FungiSNP_34 | 375013 | C > T | + | chr_8_1 | | | |
| FungiSNP_35 | 1272037 | C > T | + | chr_8_1 | | | |
| FungiSNP_36 | 281612 | T > C | + | chr_8_2 | unknown function | X | |
| FungiSNP_37 | 565087 | A > G | + | chr_8_2 | | | |
| FungiSNP_38 | 865958 | A> | + | chr_8_2 | | | |
| FungiSNP_39 | 947633 | A> | + | chr_8_2 | | | |
| FungiSNP_40 | 2482267 | G > A | + | chr_8_2 | Uncharacterized conserved coiled-coil protein | X | X |
| FungiSNP_41 | 2486601 | G> | + | chr_8_2 | Magnesium-dependent phosphatase | X | |
| FungiSNP_42 | 2709491 | T > C | + | chr_8_2 | | | |
| FungiSNP_43 | 2708043 | >A | ~ | chr_8_2 | GTPase-activating protein | X | |

Figure 3:
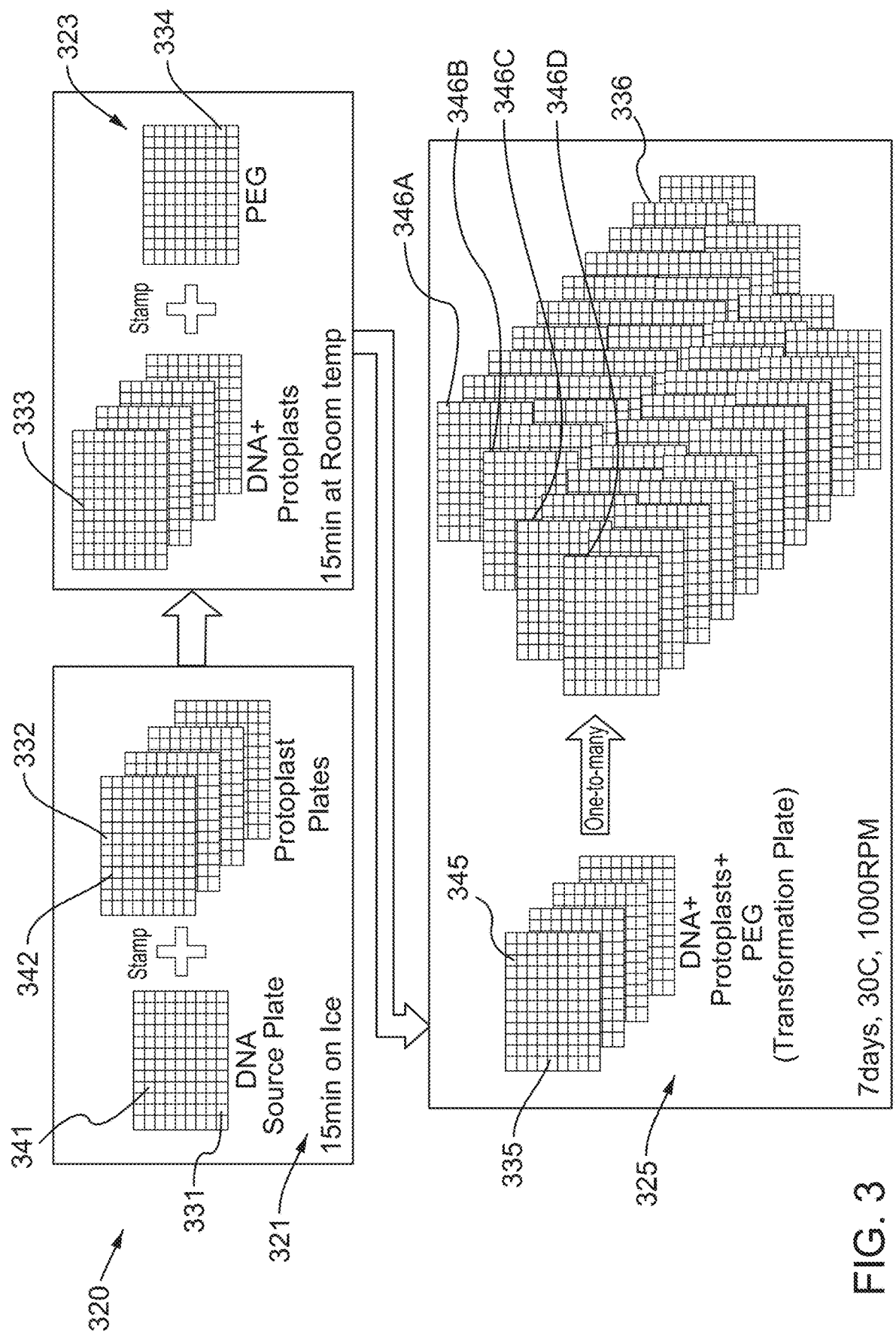
FIG. 3 is a schematic representation of a method for automated, high throughput strain generation using liquid media, according to some embodiments.

FIG. 3 is a schematic illustration of an example method 320 to generate and isolate strains of non-sporulating filamentous fungi using liquid media, according to some embodiments. In some implementations, the method 320 can be substantially similar to the method 220 described above. As described with reference to the method 220 the method 320 can be partially or fully implemented using a strain generation system (e.g., system 100) described herein. In some implementations, the method 320 can be implemented using partially or fully automatic high-throughput systems for transformation of cells using 96-well and/or 384-well plate robotics platform and liquid handling machines such as the liquid handling system 108 of the system 100 described herein.

The method 320, at 321, illustrates a step of introduction of foreign DNA into host cells to generate genetically engineered strains of non-sporulating filamentous fungi. At 321, the method 320 includes combining DNA source held in reaction areas 341 of a DNA source plate 331, to be combined with host cells in the form of protoplasts held in reaction areas 342 in the protoplast plates. The DNA used can be in any suitable concentration for example between 0.01 and 10 ug/ml. In some instances, the DNA concentration can be between 0.1 and 5 ug/ml, or between 0.25 and 2 ug/ml; or between 0.5 and 1 ug/ml.

The protoplasts can be prepared from filamentous fungal cells using any suitable method. For example, the protoplasts can be prepared by removing cell walls from the filamentous fungal cells in a fungal culture using enzymatic digestion, isolating the protoplasts, and resuspending the isolated protoplasts in a mixture comprising at least dimethyl sulfoxide (DMSO) and storing the isolated protoplasts. The suspension of protoplasts used to generate the protoplast plates 332 can be using a predefined concentration such that a specified number of protoplasts is included in each reaction area 333 (e.g., at most one protoplast per well). The protoplast plates 332 are stamped with DNA from the DNA source plate 331 to initiate transformation.

At 323, the method includes incubating the combination of DNA and protoplasts for a period of time under specified conditions following which polyethylene glycol (PEG) is added to the mixture via stamping and the combination with PEG is setup for transformation for a predefined period of time under predefined conditions. For example, as shown in FIG. 3, the combination of DNA, protoplasts and PEG in the transformation plate 335 with reaction areas 345 can be incubated for 15 minutes at room temperature and the resultant mixture can be distributed in a one-to-many fashion to any number of selection plates and incubated for 7 days at 30° C.

At 325, the method includes subjecting transformation plates 335 to high-throughput one-to-many transfer to a series of growth areas 346A-346D in selection plates 336. Following which the selection plates 336 are grown for 7 days at 30° C. and 1000 RPM. The selection plates 336 can then be subjected to further downstream processing to evaluate clonal populations found in each growth area (e.g., 346A-346D) and select specific strains of cells based on the evaluation. For example, the downstream processing can include evaluating each growth area suitably to facilitate selection of clonal populations derived from fungal strains including the desired genetic perturbation, purifying single transformants and/or clonal populations arising from a single homokaryotic transformant by performing selection and counter-selection, further growing the purified transformants and/or clonal population from single transformants in media conducive to regeneration of the filamentous fungal cells, etc.

Figure 4:
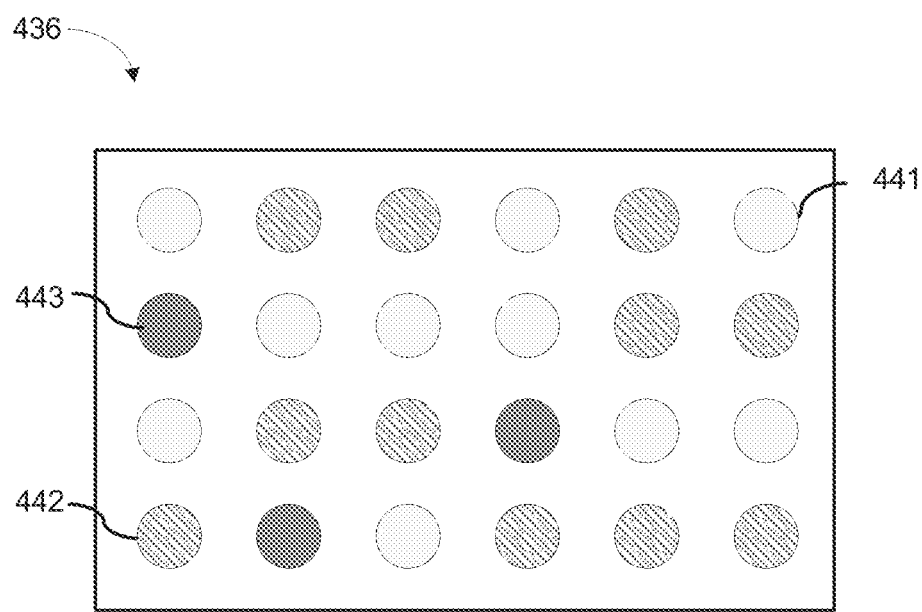
FIG. 4 is a schematic representation of an example substrate with growth areas having potential growth of clonal transformant strains resulting from transformation outputs, according to some embodiments.

FIG. 4 illustrates an example substrate 436. The substrate 436 can be any suitable microtiter plate. In some cases, the microtiter plate contains 96 wells, 384 wells or 1536 wells. In some instances, the substrate 436 can be a transformation plate including reaction areas configured to hold reaction mixtures to support transformation. In some instances, the substrate 436 can be a selection plate having growth areas configured to support growth of clonal populations from transformants. The substrate 436 can be evaluated in each instance to measure a success and/or failure of transformation and/or clonal population growth from transformation. For example, the substrate 436 can be a transformation plate and be evaluated during QC using any suitable method (e.g., colorimetry, measurement of optical density (OD), etc.). The transformation plate can be identified to include wells 441 having no transformants, wells 442 having a single transformant (i.e. no more than a single transformant), and wells 443 having more than a single transformant. In some instances, a measure of saturation may be calculated to quantify the relative number or percentage of wells 441 having no transformants compared to total number of wells (441, 442, and 443). During QC evaluation the wells 442 with a single transformant can be deemed a success and the properties such as the genotype of the single transformant can be determined. Homokaryotic transformants can be a desired result and categorized as a success. In some instances, the number of each type of well can be quantified and based on the quantification the transformation plate 436 can be deemed a successful result when one or more measured indicia meet specified criteria (e.g., the number of wells with no transformants is less than 20%, the number of wells with single transformants is above 20%, and/or the like).

As another example, the substrate 436 can be a selection plate and be evaluated during QC using any suitable method (e.g., colorimetry, measurement of optical density (OD), etc.). The selection plate can be identified to include wells 441 having no growth of clonal populations, wells 442 having clonal populations arising from a single transformant (i.e. no more than a single transformant), and wells 443 having populations grown from more than a single transformant. During QC evaluation the wells 442 with clonal populations from a single transformant can be deemed a success and the properties such as the genotype of the single transformant can be determined. Clonal populations from homokaryotic transformants can be a desired result and categorized as a success. In some instances, the number of each type of well can be quantified and based on the quantification the selection plate 436 can be deemed a successful result when one or more measured indicia meet specified criteria (e.g., the number of wells with no clonal growth is less than 20%, the number of wells with clonal populations from single transformants is above 20%, and/or the like).

Figure 5:
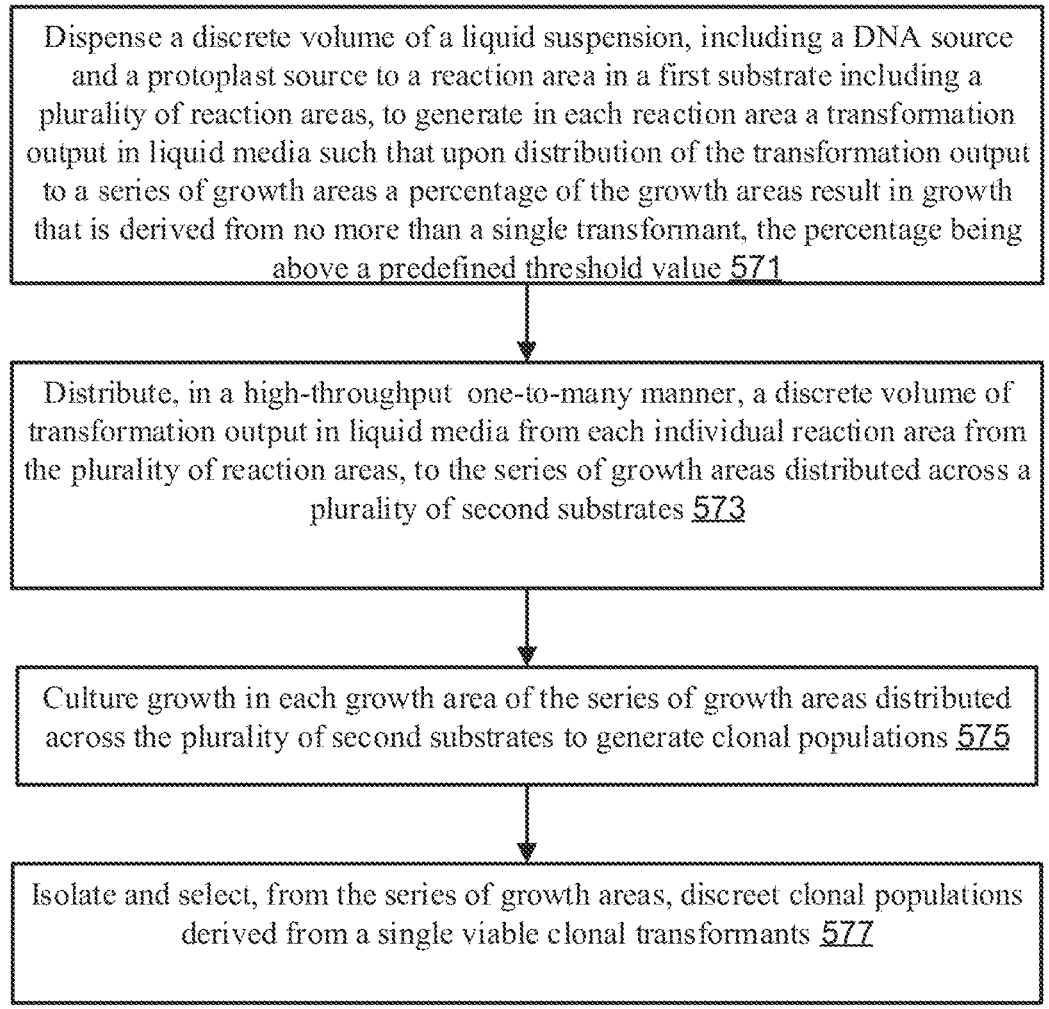
FIG. 5 is a flow chart showing a method for automated, high throughput strain generation using liquid media, according to some embodiments

FIG. 5 is a flowchart illustrating an example method 520 of generating a desired strain of a genetically engineered cell using liquid media, according to some embodiments. In some implementations, the method 520 can be partially or fully substantially similar to the method 220 and/or the method 320 described above. As described with reference to the methods 220 and 320, the method 520 can be partially or fully implemented using a strain generation system (e.g., system 100) described herein. In some implementations, the method 520 can be implemented using partially or fully automatic high-throughput methods for transformation of cells and growth of clonal populations arising from transformants using 96-well plate robotics platform and liquid handling machines.

The method 520 includes, at 571, dispensing a discrete volume of a liquid suspension including a DNA source and a protoplast source to an individual reaction area in a first substrate that includes a plurality of reaction areas. The dispensing is configured to generate, in each reaction area, a transformation output in liquid media. The dispensing is configured such that the transformation outputs from each reaction area can be distributed across a series of growth areas as described herein. In some instances, the dispensing can be such that the transformation outputs are optionally diluted and distributed in a one-to-many distribution into selection plates (see FIG. 3 336). The dispensing is further configured such that upon the distribution of the transformation output of each reaction area to a series of growth areas a percentage of growth areas that result in a growth that is derived from no more than a single transformant is above a predefined threshold value In some instances, the dispensing can be configured such that a percentage of individual wells in the selection plates that result in a growth output that includes no more than a single transformant is above a predefined threshold value. In some implementations, parameters of the liquid suspension may be adapted to meet the threshold criterion of obtaining a specific minimum percentage of individual reaction areas that result in a transformation output with no more than a single transformant. For example, as described previously, the adaptation may be directed to parameters of reaction inputs such as the concentration of the DNA source and/or the concentration of the protoplast source, volume of the DNA source and/or the volume of the protoplast source included in each discreet volume of the liquid suspension, etc.

At 573, the method 520 includes distributing, in a high-throughput one-to-many manner, a discrete volume of transformation output in liquid media from each individual reaction area from the plurality of reaction areas, to a series of growth areas distributed across a plurality of second substrates. In some implementations, the distributing in a one-to-many manner is directed to spatially space the discreet volumes of transformation output in order to maximize the likelihood of obtaining clonal populations from single viable clonal transformants. In some implementations, the high-throughput distribution of the transformation output can be implemented using partially or fully automatic high-throughput systems and methods for one-to-many transfer of cell suspensions in liquid media using 96-well plate robotics platform and liquid handling machines such as the liquid handling system 108 of the system 100 described herein.

At 575, the method 520 includes culturing growth in each growth area of the series of growth areas distributed across the plurality of second substrates to generate clonal populations of genetically engineered cells. At 577, the method 520 includes isolating and selecting, from the series of growth areas, discreet clonal populations derived from a single viable clonal transformant. In some implementations, the selection of the clonal populations may be based on an evaluation of the growth outputs of each growth area from the series of growth areas. For example, clonal populations determined to have risen from a single transformant can be selected. In some instances, the genotype of the clonal populations determined to have risen from a single transformant can be determined and the clonal populations rising from a single clonal homokaryotic transformant can be preferentially selected for further downstream processing.

In some implementations, the selected clonal populations can be consolidated into sub-culture plates as described herein. In some implementations, the consolidated clonal populations in sub-culture plates can be subjected to additional selection pressure to further enrich growth of the clonal populations.

The various methods or steps involved in the generation of genetically pure strains of engineered cells can be evaluated and adapted to maximize the efficacy of generating cells that are best suited to commercial production of desired biomolecules. In some implementations, the adaptation of the methods for strain generation can be based on iterative testing and evaluation of variations in parameters involved in the high-throughput transformation to generate transformants expressing the gene of interest as described herein.

FIG. 6 is a flowchart illustrating an example method 620 of testing and evaluating a set of transformation outputs generated from transformation of a host cell in liquid media to incorporate a specified foreign DNA to express a desired biomolecule. The method 620 can be implemented by a strain generation system (e.g., system 100) as described herein. In some implementations, the method 620 can be implemented using high-throughput systems and methods as described herein. In some implementations, portions of the method 620 can be implemented using partially or fully automatic systems having liquid handlers, such as the liquid handling system 108 of the system 100 described herein. In some implementations, portions of the method 620 can be implemented by one or more processing components (e.g., the transformation controller 111) using processors included in compute devices (e.g., processor 104 of compute device 101 described in FIG. 1). In some instances, the processing components can be routines or programs in the form of instructions stored in a memory and executed by processor(s) as described herein.

At 671, the method 620 includes Select a set of volumes of liquid suspension including a DNA source sample and a protoplast source associated with a cell, each volume of the liquid suspension being different, by at least one predetermined property, from the remaining volumes of the set of volumes of the liquid suspension. The predetermined property can be any suitable property including a volume of the DNA source, a concentration of the DNA source, a molar ratio of specified DNA ends included in the DNA source sample, or a ratio of concentration of DNA source and concentration of protoplast source.

At 673, the method 620 includes dispensing the set of volumes of the liquid suspension across a plurality of reaction areas (e.g., wells in a microtiter plate), each reaction area from the plurality of reaction areas including a discrete quantity of the liquid suspension.

At 675, the method includes transforming the quantity of liquid suspension included in each reaction area from the plurality of reaction areas to generate a transformation output. Each transformation output in each reaction area may or may not include one or more transformants based on the properties of the volume of the liquid suspension used.

At 677 the method 620 optionally includes evaluating the set of transformation outputs to calculate a measure of success and/or failure of a desired efficacy of transformation. The evaluating can be through a process of screening the transformation output in each reaction area from the plurality of reaction areas for the presence or absence of a single transformant. In some implementations, only the transformation outputs including a single transformant can be selected for distributing to growth areas for further processing (e.g., for growing clonal colonies for use).

The measure of success and/or failure can be based on at least one of (i) a number of transformation outputs that included a successful transformant, and (ii) a number of transformation outputs that include a desired number of transformants. The reaction areas can be evaluated during QC using any suitable method (e.g., colorimetry, measurement of optical density (OD), etc.) as described herein. For example, in some instances, the number of transformation outputs with at least one transformant may be used to calculate a lower bound criteria to determine a suitable range of parameters designed to produce optimal generation of desired clonal strains. In some instances, the number of transformation outputs with no more than one transformant may be used to determine a suitable range of parameters that result in the generation of clonal strains that maximize efficiency of industrial production of biomolecules. In some instances, iterative repetitions of the method 620 can be conducted to evaluate variations of parameters involved in transformation. The transformation outputs resulting from the iterative repetitions can be evaluated to determine the number of transformation outputs with no more than one transformant which may be used to determine a suitable range of parameters that result in reproducibly high fraction of clonal strains with a desired homokaryotic genotype (e.g., with a greater than 70% reproducibility that greater than 20% of clonal strains are homokaryotic). In some implementations, the reproducibility can be quantified by a measure of probability that a specified fraction of reaction areas in a transformation plate include a desired single homokaryotic transformant. The probability can be 0.1, 0.2, 03, 0.4, 0.5, 0.6, 0.7, 0.8, 0.9, 1.0 or any number there between.

Figure 14:
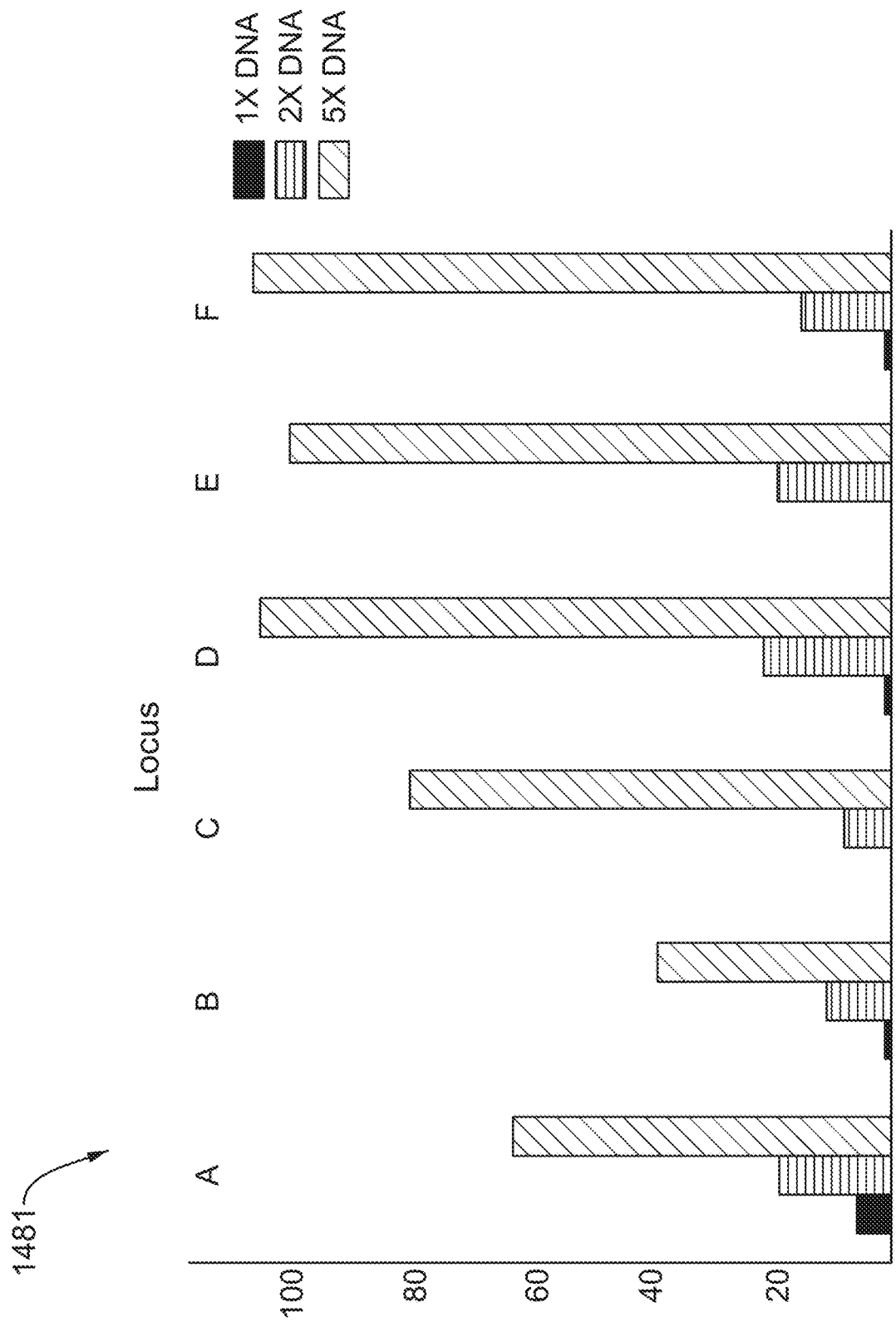
FIG. 14 is an exemplary plot of total transformant output obtained from transformation using varying amounts of DNA source, according to some implementations.

FIG. 14 shows an example plot of total transformant output, for six different gene loci, resulting from the iterative repetitions using varying amounts of DNA (e.g., 1×, 2×, and 5×). The transformation outputs obtained from each iterative process were evaluated to determine the relationship between the DNA concentration used and the total transformant output obtained as a result while maintaining a constant protoplast concentration. In the example analysis shown in FIG. 14, the transformation outputs that resulted from reaction inputs having 5×DNA content had higher total transformant output across all the loci A-F analyzed, compared to transformation outputs obtained from reaction inputs having 1× or 2×DNA content.

In some implementations, the adaptation of the methods for strain generation can be based on iterative testing and evaluation of variations in parameters involved in the high-throughput one to many transfers of transformation outputs to generate clonal populations expressing the gene of interest as described herein.

FIG. 7 is a flowchart illustrating an example method 720 of testing and evaluating a set of transformation outputs generated from transformation of a host cell in liquid media to incorporate a specified foreign DNA to express a desired biomolecule. The method 720 can be implemented by a strain generation system (e.g., system 100) as described herein. In some implementations, the method 720 can be implemented using high-throughput systems and methods as described herein. In some implementations, portions of the method 720 can be implemented using partially or fully automatic systems having liquid handlers, such as the liquid handling system 108 of the system 100 described herein. In some implementations, portions of the method 720 can be implemented by one or more processing components (e.g., the selection controller 113) using processors included in compute devices (e.g., processor 104 of compute device 101 described in FIG. 1). In some instances, the processing components can be routines or programs in the form of instructions stored in a memory and executed by processor(s) as described herein. In some implementations the method 720 can be conducted in addition to other methods such as the method 620 described above.

At 771, the method 720 includes dispensing discrete volumes of a liquid suspension, obtained from a reaction area from a plurality of reaction areas in a first substrate, to a series of growth areas from a plurality of series of growth areas distributed across a plurality of second substrates. The discrete volumes of a liquid suspension can include transformation outputs obtained as a result of a transformation set up in a plurality of reaction areas following automated, high-throughput methods. In some instances, the discrete volumes of a liquid suspension can include transformation outputs obtained from multiple transformations set up to evaluate reaction inputs, each volume of the liquid suspension used to set up each transformation being different, by at least one predetermined property, from the remaining volumes used to set up the remaining transformations.

The plurality of reaction areas includes a set of transformants, and the dispensing is configured to generate a set of growth outputs including colonies derived from the set of transformants. The set of transformants can be a result of a transformation process set up following portions of the method 620 descried above. For example, the transformation process may be iteratively setup and repeated with variations to one or more parameters or predetermined properties associated with transformation of the desired cell. In some instances, the transformation output obtained from transformation plates may be diluted by a known amount (e.g., 1×/10, 1×/20, etc.) and the diluted transformation outputs may then be transferred in discreet volumes to the series of growth areas across selection plates, as described herein.

At 772 the method 720 includes evaluating the set of transformation outputs to calculate at least one of (i) a number of growth outputs that included colonies derived from a successful transformant, and (ii) a number of growth outputs that included colonies derived from a single clonal transformant. The growth areas on selection plates can be evaluated during QC using any suitable method (e.g., colorimetry, measurement of optical density (OD), etc.) as described herein.

In some instances, the number of growth outputs arising from a transformant may be used to calculate a lower-bound criteria to determine a suitable range of parameters designed to produce optimal generation of desired clonal strains. In some instances, the number of growth outputs with clonal populations arising from no more than a single transformant may be used to determine a suitable range of parameters that result in the generation of clonal strains that maximize efficiency of industrial production of biomolecules. In some instances, iterative repetitions of the method 820 can be conducted to evaluate variations of parameters involved in the high-throughput one-to-many transfers of transformation outputs. For example, iterative repetitions of the method 820 can be conducted for different dilutions of transformation outputs before the on-to-many transfer to selection plates. The transformation outputs and/or growth outputs resulting from the iterative repetitions can be evaluated to determine a measure of number or fraction of genetically pure clonal populations obtained that are found to grow from no more than a single transformant. This measure may then be used to determine a suitable range of parameters, for example a suitable range of dilutions of transformation outputs, that result in reproducible minimum desired fraction of clonal strains with a desired homokaryotic genotype (e.g., with a greater than 70% reproducibility that greater than 20% of clonal strains are homokaryotic). The desired fraction can be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%. In some implementations, the reproducibility can be quantified by a measure of probability that a specified fraction of reaction areas in a transformation plate include a desired single homokaryotic transformant. The probability can be 0.1, 0.2, 03, 0.4, 0.5, 0.6, 0.7, 0.8, 0.9, 1.0 or any number there between.

Figure 9:
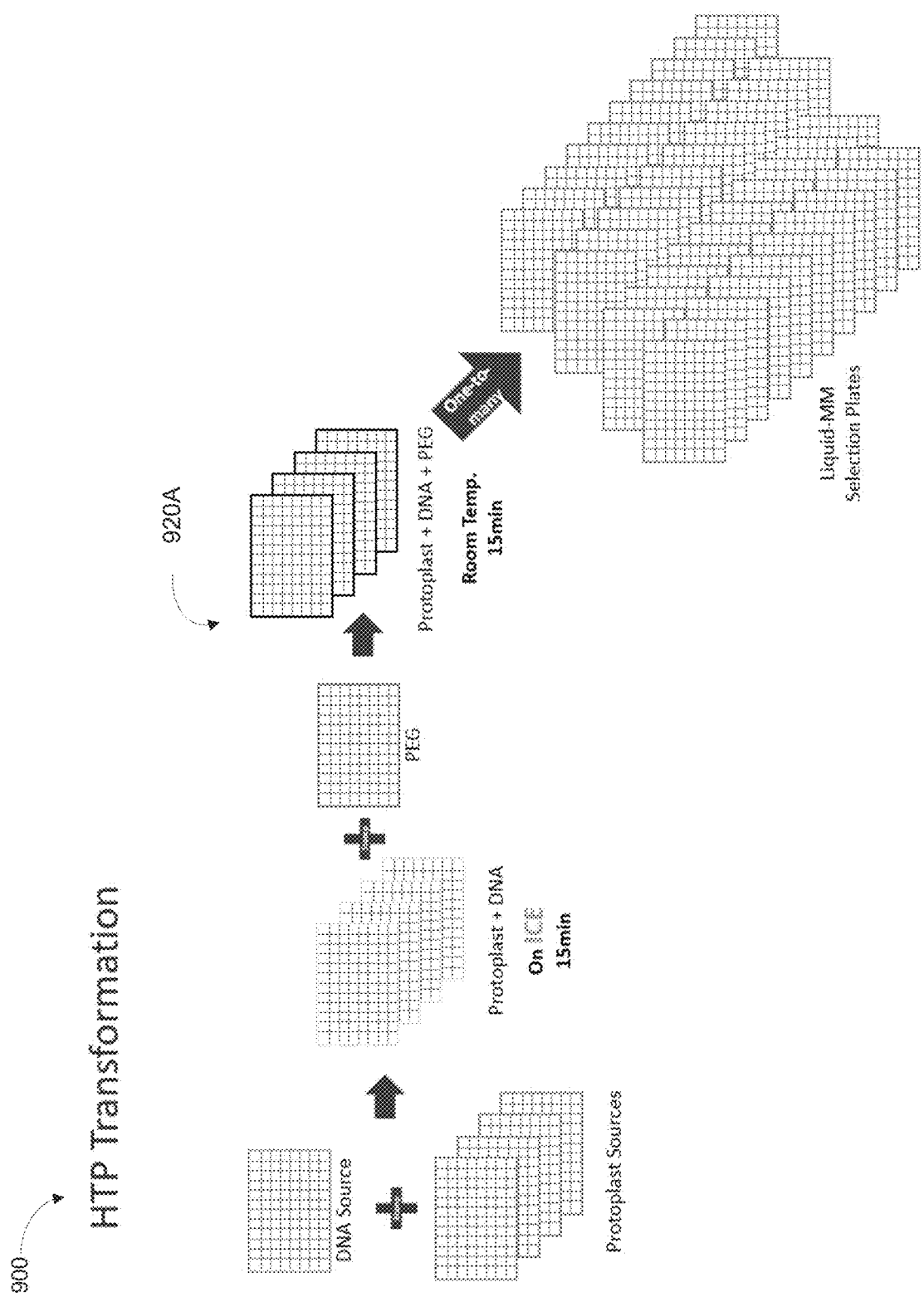
FIG. 9 is a schematic representation of an example method for automated, high throughput strain generation including a first part of generation of transformation plates and selection plates in liquid media, according to some embodiments.
Figure 10:
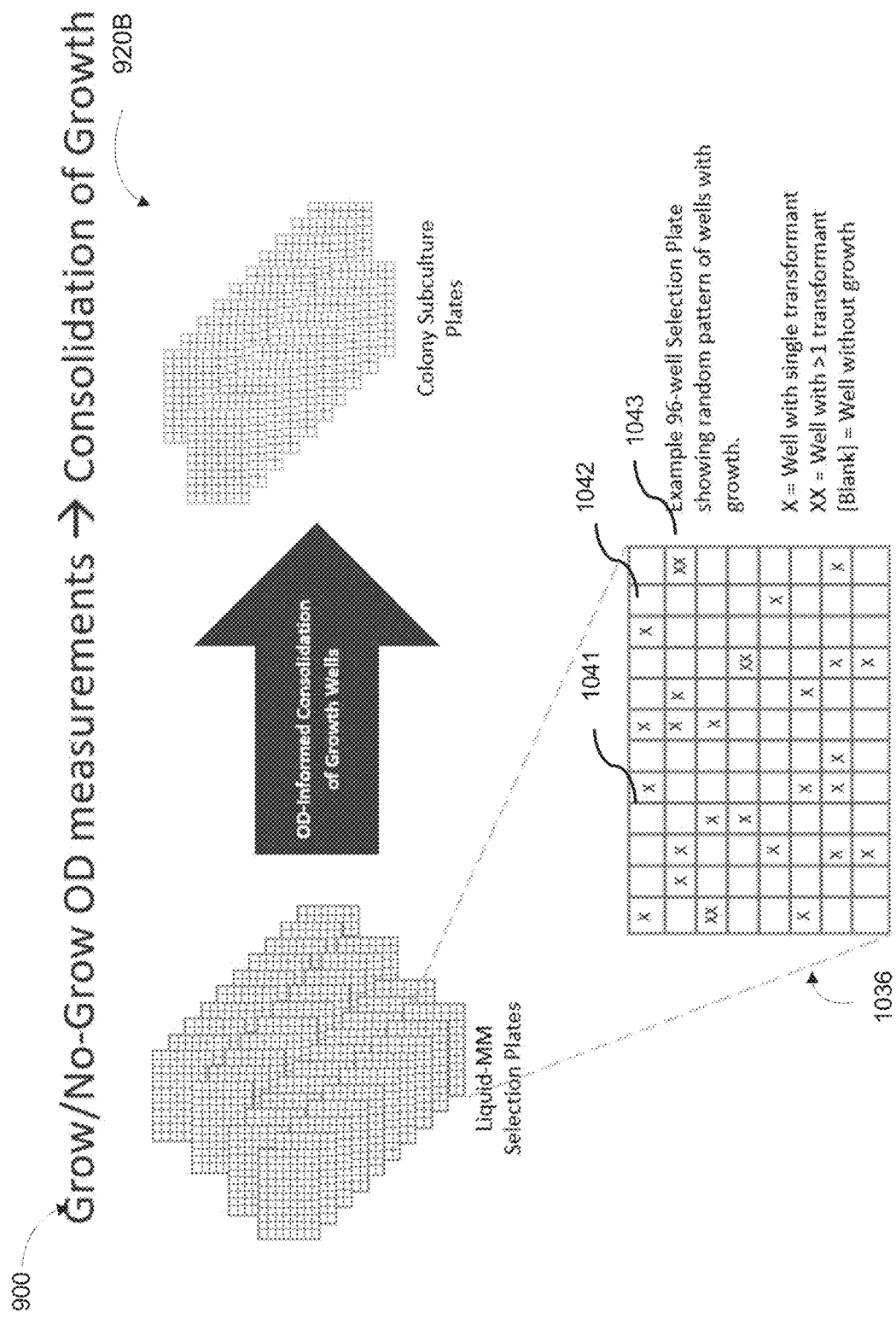
FIG. 10 is a schematic representation of an example method for automated, high throughput strain generation including a second part of evaluation and consolidation of growth outputs of selection plates in liquid media, according to some embodiments.

FIGS. 9 and 10 illustrate portions of an example process 900 for automated, high throughput strain generation according to some embodiments. FIG. 9 is an illustration of a first part 920A of the strain generation process 900 including generation of transformation plates and selection plates in liquid media. As shown, and described herein, transformation plates are generated by stamping plates including a predetermined amount of DNA source per well and Protoplast plates including predetermined amounts of protoplasts per well and incubating on ice for approximately 15 minutes followed by addition of PEG to each well via stamping. The transformation plates are then used to obtain transformation outputs (that may or may not include transformants) and the transformation outputs are distributed in a one-to-many manner to a series of wells in selection plates, in liquid media. The selection plates are then incubated for a predetermined period selected from a range of periods (e.g., 5-10 days) at a pre-determined temperature selected from a range of temperatures (e.g., 25° C.-35° C.).

FIG. 10 is a schematic representation of a second part 920B of the strain generation process 900 including evaluation and consolidation of growth outputs of selection plates in liquid media, according to some embodiments. As shown, in this example method 920B, the selection plates are stamped with clear assay plates to assess which of the growth outputs include viable transformants. The assessment is done by measuring a grow-no-grow indication, with "grow" indicating that there was growth in a particular well and the growth was derived from a transformant and/or derived from a single viable clonal transformant, and no-grow indicating that there was no growth in a particular well. In some implementations, a subset of the grow wells is selected on the basis of growth being derived from a single desired clonal transformant and the growth outputs of the selected wells are consolidated in sub-culture plates for a suitable period of time under suitable conditions.

In some implementations, the strain generation process 900 can include quality control (QC) measurements (not shown in FIGS. 9 and 10). For example, Next-Generation Sequencing (NGS) can be used for Quality Control (QC) measurements to evaluate the efficacy of the high-throughput strain generation process 900. The colonies obtained from the selection plates and consolidated in the sub-culture plates can be processed via NGS-QC to analyze the results.

FIG. 10 also shows, in a magnified view, a schematic representation of an example substrate 1036 (a 96-well selection plates), according to some implementations. The example substrate 1036 is shown to include growth areas in the form of wells, implemented according to some embodiments. As described previously, with reference to substrate 436, the series of growth areas included in the substrate 1036 can be distributed with transformation outputs (from transformation plates) in a one-to-many manner using high-throughput systems and/or methods. The growth areas can be evaluated to measure a success and/or failure of growth of clonal populations derived from transformants in transformation outputs. In some instances, representative selection plates can be examined for successful grow/no-grow patterns. For example, the substrate 1036 can be a selection plate and be evaluated during QC using any suitable method (e.g., colorimetry, measurement of optical density (OD), etc.). The selection plate 1036 can be identified to include wells 1041 having no transformants, wells 1042 having a single transformant (i.e. no more than a single transformant) denoted by "X", and wells 1043 having more than a single transformant, denoted by "XX". In some instances, a measure of saturation may be calculated to quantify the relative number or percentage of wells 1041 having no transformants compared to total number of wells (441, 442, and 443). In some instances, the selection plates can include positive controls (not shown in substrate 1036). During QC evaluation the wells 1042 with a single transformant can be deemed a success and the properties such as the genotype of the single transformant can be determined. Homokaryotic transformants can be a desired result and categorized as a success. In some instances, the number of each type of well can be quantified and based on the quantification the transformation plate 1036 can be deemed a successful result when one or more measured indicia meet specified criteria (e.g., the number of wells with no transformants is less than 20%, the number of wells with single transformants is above 20%, and/or the like).

Figures 15A, 15B:
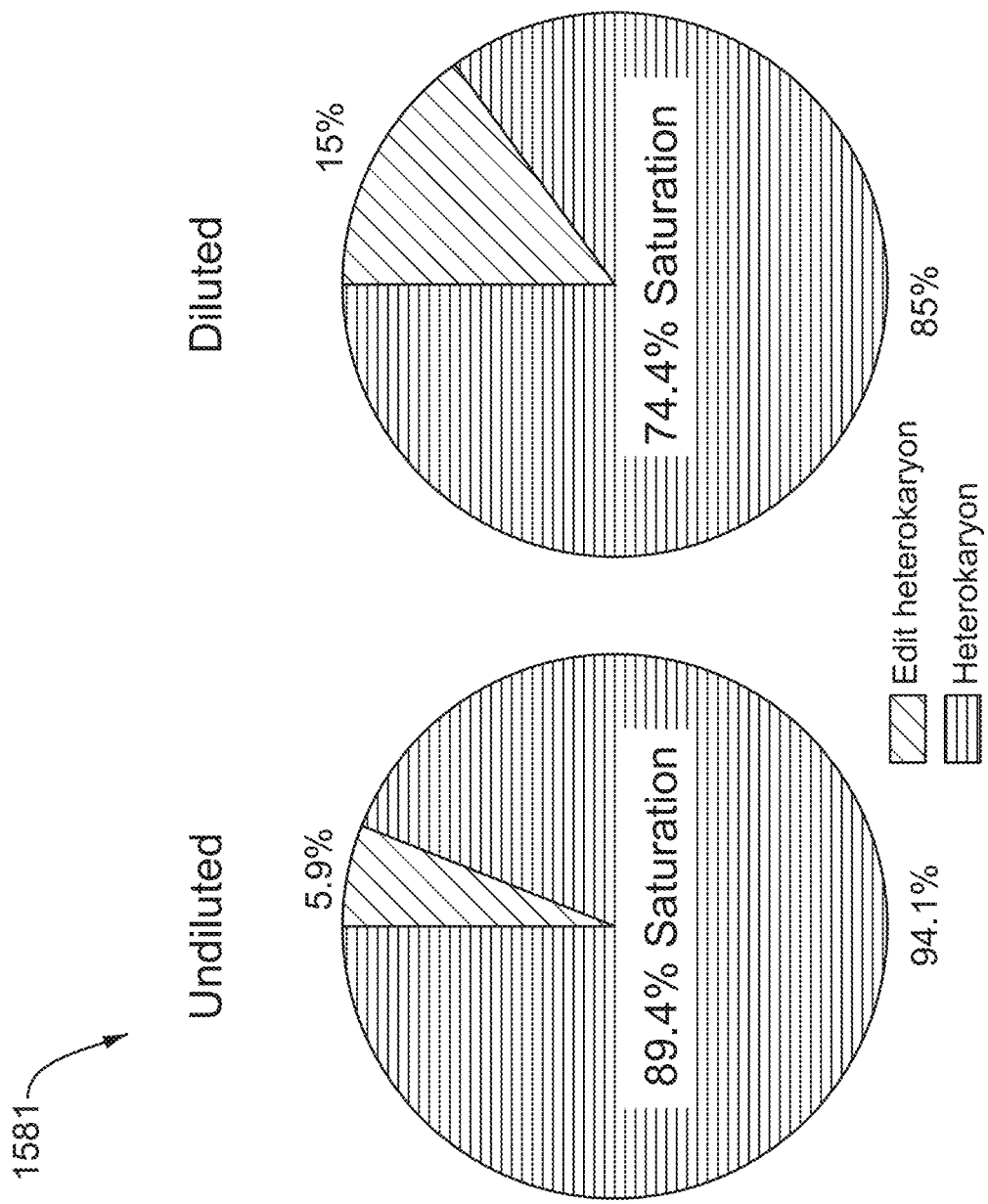
FIGS. 15A and 15B are exemplary plots of total clonal populations in growth output and relative proportions of homokaryotic (clonal) and heterokaryotic (non-clonal) strains in the growth output obtained from distributing undiluted and diluted volumes of transformations using high throughput strain generation, according to some implementations.

FIGS. 15A and 15B show example plots of growth outputs obtained from two different selection procedures used to generate strains of non-sporulating filamentous fungi. The results shown in FIG. 15A was obtained using transformation outputs that were undiluted before conducting a one-to-many transfer to a series of growth areas on selection plates. The results shown in FIG. 15B was obtained using transformation outputs similar to those used for FIG. 15A, but with a known dilution before conducting the one-to-many transfer to a series of growth areas on selection plates.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

A brief table of contents (i.e., Table 5) is provided below solely for the purpose of assisting the reader. Nothing in this table of contents is meant to limit the scope of the examples or disclosure of the application.

TABLE 5

Table of Contents for Example Section

| Example # | Title | Brief Description |
|---|---|---|
| 1 | HTP Genomic Engineering of filamentous fungi: Generation & Storage of Filamentous Fungal Protoplasts | Describes methods for generating and storing protoplasts for use in HTP genomic engineering methods |
| 2 | HTP Genomic Engineering of filamentous fungi: Alternative Method for Generating Protoplasts | Describes an alternative method for generating protoplasts for use in HTP genomic engineering methods |
| 3 | HTP Genomic Engineering of filamentous fungi: Demonstration of Co-transformation of Filamentous Fungal Protoplasts-Proof of Principle | Describes proof-of-principle for HTP co-transformation of filamentous fungi |
| 4 | HTP Genomic Engineering of filamentous fungi: Demonstration of Co-transformation of Filamentous Fungal Protoplasts- Proof of Principle using colorimetric selection/counterselection | Describes HTP method for proof-of-principle for using selection/counter-selection in filamentous fungal protoplasts |
| 5 | Purification of Transformed Fungal Strains into Clonal Populations at Scale: Evaluation of Transformation outputs | Describes HTP method for evaluation of transformation outputs |

TABLE 5-continued

Table of Contents for Example Section

| Example # | Title | Brief Description |
|---|---|---|
| 6 | Purification of Transformed Fungal Strains into Clonal Populations at Scale: Evaluation of Transformation outputs for varied parameters of transformation | Describes HTP method for evaluation of transformation outputs and effects of varied parameters of transformation |
| 7 | Purification of Transformed Fungal Strains into Clonal Populations at Scale: Evaluation of growth outputs for varied parameters of transformation outputs | Describes HTP method for evaluation of growth outputs for effects of varied parameters of process |

Figure 8:
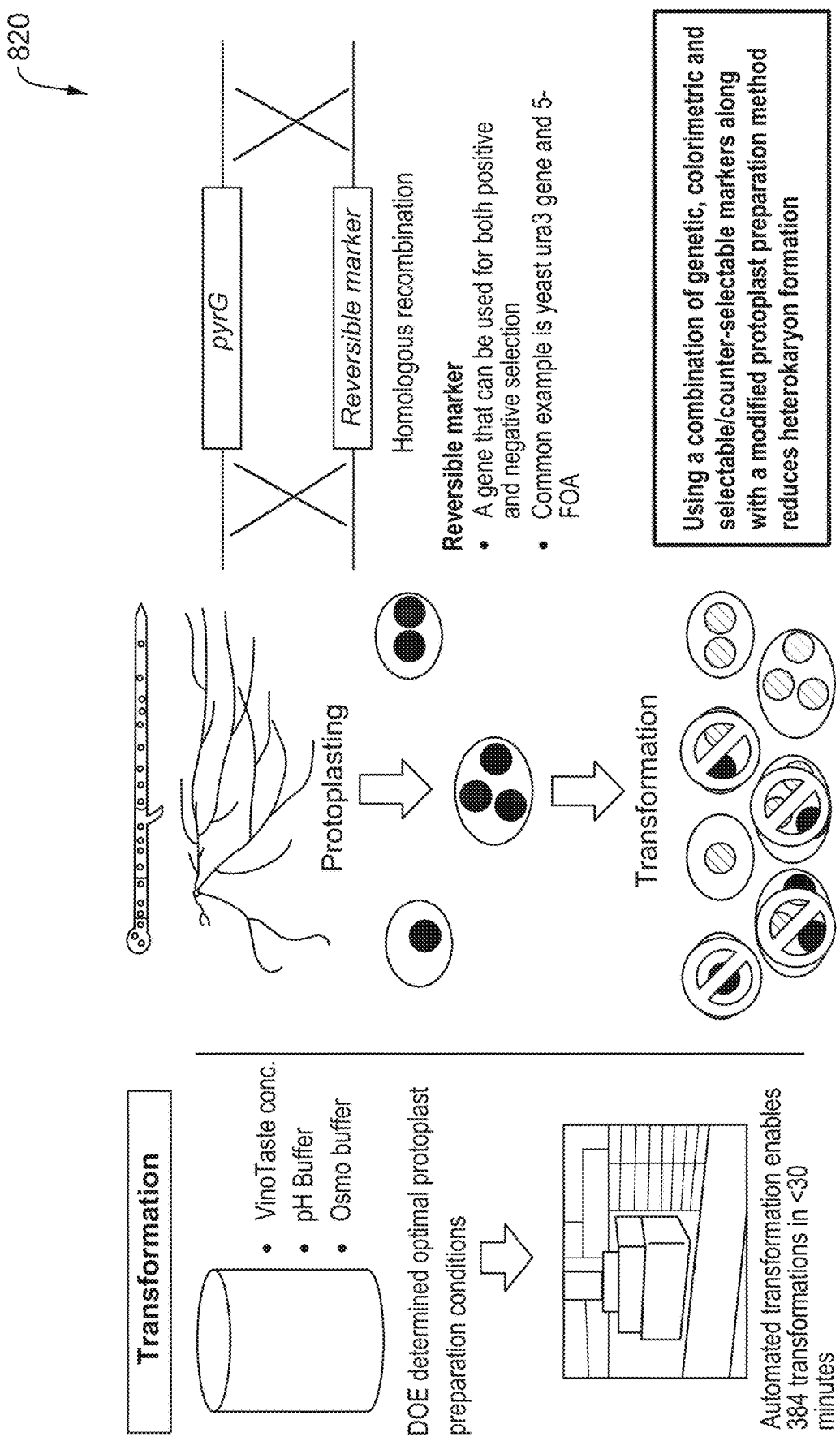
FIG. 8 is a schematic illustration of a general outline for the automated transformation, screening and purification of homokaryotic protoplasts provided herein and described in Example 1.

Example 1: HTP Genomic Engineering of Filamentous Fungi: Generation & Storage of Filamentous Fungal Protoplasts Generation of Protoplasts As shown in FIG. 8, 100 milliliters of complete media was inoculated with $10^6$ conidia/ml of *Aspergillus niger* and grown overnight at 150 rpm at 30° C. Following the overnight growth, the mycelia were harvested by filtering the culture through Miracloth. Subsequently, the mycelia were rinsed thoroughly with sterile water. For the experiments described in the following examples, two strains of *A. niger* were used, A. *Niger* strain 1015 and *A. niger* strain 11414. Harvested and washed mycelia were then subjected to enzymatic digestion by with a VinoTaste Pro (VTP) enzymatic cocktail. Features of each strain are depicted in FIG. 9.

For *A. niger* strain 1015, enzymatic digestion was performed by first making 50 ml of 60 mg/ml of VTP in protoplasting buffer (1.2 M magnesium sulfate, 50 mM phosphate buffer, pH 5). After dissolving the VTP, the buffer was placed in clean Oakridge tubes and spun at 15,000×g for 15 minutes. The solution was then filter sterilized after centrifugation. Once made, some of the harvested mycelia was added to the VTP solution and the mycelia was digested at 30° C. at 80 rpm for 2-4 hours. At various intervals during VTP digestion, small samples were examined under 400× magnification for the presence of protoplasts (i.e., large round cells that are larger than conidia and are sensitive to osmotic lysis). When most or all of the mycelia were digested, the culture was filtered through sterile Miracloth such that 25 ml of the flow through containing the protoplasts were separated into 1 of 2 50 ml Falcon tubes. To each of the 25 ml samples, 5 ml of 0.4 M ST buffer (0.4 M Sorbitol, 100 mM Tris, pH 8) was gently overlaid. The overlaid samples were then spun at 800×g for 15 minutes at 4° C. in order to form a visible layer between the ST and digestion buffers. The protoplasts were then removed with a pipette and mixed gently with 25 ml of ST solution (1.0 M sorbitol, 50 mM Tris, Ph 8.0) and respun at 800×g for 10 minutes. The protoplasts should pellet at the bottom of the tube. The protoplasts were then resuspended in 25 ml of ST solution and collected by centrifugation at 800×g for 10 minutes.

For *A. niger* strain 11414, enzymatic digestion was performed by first making 40 ml of 30 mg/ml of VTP in protoplasting buffer (0.6 M ammonium sulfate, 50 mM Maleic Acid, pH 5.5). All of the harvested mycelia were added to the VTP solution and the mycelia were digested at 30° C. at 70 rpm for 3-4 hours. At various intervals during VTP digestion, small samples were examined under 400× magnification for the presence of protoplasts. When most or all of the mycelia were digested, the culture was filtered through sterile Miracloth. The filtrate was then spun at 800×g for 10 min at 4° C. to pellet the cells. 25 ml of ST solution (1.0 M sorbitol, 50 mM Tris, pH 8.0) was added and the cells were resuspended and respun. The cells were then washed in 10 ml of STC buffer (1.0 M sorbitol, 50 mM Tris, pH 8.0, 50 mM $CaCl_2$)) and collected by centrifugation at 800×g for 10 min. The protoplasts (~$10^8$/ml) were counted and adjusted to be at $1.2×10^7$/ml.

For protoplasts generated from either *A. niger* strain (i.e., 1015 or 11414), following enzymatic digestion, 20% v/v of a 40% PEG solution (40% PEG-4000 in STC buffer)) was added to the protoplasts and mixed gently followed by adding 7% v/v of dimethyl sulfoxide (DMSO) to make a 8% PEG/7% DMSO solution. Following resuspension, the protoplasts were distributed to 96 well (25-50 microliters) microtiter plates using an automated liquid handler as depicted in FIG. 8, followed by storage at least −80° C. prior to transformation.

Example 2: HTP Genomic Engineering of Filamentous Fungi: Alternative Method for Generating Protoplasts Approximately 500 milliliters of complete media was inoculated with $10^6$ conidia/ml of *Aspergillus niger* and grown overnight at 150 rpm at 30° C. Following the overnight growth, the mycelia were harvested by filtering the culture through Miracloth. Subsequently, the mycelia were rinsed thoroughly with sterile water. Harvested and washed mycelia were then subjected to enzymatic digestion by with a VinoTaste Pro (VTP) enzymatic cocktail.

Enzymatic digestion was performed by first making 50 ml of 60 mg/ml of VTP in protoplasting buffer (1.2 M magnesium sulfate, 50 mM phosphate buffer, pH 5). After dissolving the VTP, the buffer was placed in clean Oakridge tubes and spun at 15,000×g for 15 minutes. The solution was then filter sterilized after centrifugation. Once made, some of the harvested mycelia was added to the VTP solution and the mycelia was digested at 30° C. at 80 rpm for 2-4 hours. At various intervals during VTP digestion, small samples were examined under 400× magnification for the presence of protoplasts (i.e., large round cells that are larger than conidia and are sensitive to osmotic lysis). When most or all of the mycelia were digested, the culture was filtered through sterile Miracloth and the filtrate was collected in a graduated cylinder. The filtered protoplasts were transferred to a graduated cylinder and a buffer of lower osmolite concentration (5 ml of 0.4 M ST buffer (0.4 M Sorbitol, 100 mM Tris, pH 8) was gently overlaid. The overlaid samples were then spun at 800×g for 15 minutes at 4° C. and protoplasts were then removed with a pipette and mixed gently with 25 ml of ST solution (1.0 M sorbitol, 50 mM Tris, Ph 8.0) and respun at 800×g for 10 minutes. The protoplasts should pellet at the bottom of the tube. The protoplasts were then resuspended in 25 ml of ST solution and collected by centrifugation at 800×g for 10 minutes.

Example 3: HTP Genomic Engineering of Filamentous Fungi: Demonstration of Co-Transformation of Filamentous Fungal Protoplasts-Proof of Principle Preparation of Targeting DNA In an effort to provide proof of concept (POC) for the automated filamentous fungal transformation and screening method disclosed herein, the DNA sequence of the *Aspergillus niger* argB gene was obtained and the proper reading frame was determined. A set of SNPs were then designed such that integration of any of said SNPs into the argB locus of the *A. niger* genome would result in null mutation of the argB gene. The designs were generated as in silico constructs that predicted a set of oligomers that were used to build the constructs using Gibson assembly.

Automated Transformation of Protoplasts

Protoplasts derived from *A. niger* strain 1015 generated and stored in 96 well plates (100 microliters protoplast/well) as described in Example 1 were then subjected to traditional PEG Calcium mediated transformations using automated liquid handlers to combine the SNP DNA constructs with the protoplast-PEG/DMSO mixtures in the 96 well plates. More specifically, to 100 microliters of protoplasts, 1-10 micrograms of the SNP DNA constructs (in a volume of 10 microliters or less) were added and the mixture was incubated on ice for 15 minutes. To this mixture, 1 ml of 40% PEG was added and incubated for 15 minutes for room temperature. Subsequently, 10 ml of minimum medium plus 1 M sorbitol was added and shaken at 80 rpm for 1 hour at 30° C. Following this incubation, the protoplasts were spun down at 800× g for 5 minutes and then resuspended in 12 ml of minimal medium containing 1 M sorbitol and 0.8% agar. The following day, using an additional automated liquid handling step, the protoplasts were plated on to selective media (i.e., minimal media+arginine) and non-selective media (i.e., minimal media). Successful transformation of the protoplasts generated with the automated transformation protocol would be expected to be auxotrophic for arginine and thus not grow on minimal media lacking arginine due to targeting of the argB gene by the SNP constructs.

About 3% of the transformants displayed integration of the targeting DNA constructs at the correct (i.e., argB) locus as evidenced by lack of growth in the minimal media lacking arginine. Confirmation of integration of the SNP containing constructs at the correct locus will be confirmed via next generation sequencing.

Example 4: HTP Genomic Engineering of Filamentous Fungi: Demonstration of Co-Transformation of Filamentous Fungal Protoplasts—Proof of Principle Using Colorimetric Selection/Counterselection This example demonstrates an additional proof of principle for the automated, HTP co-transformation of filamentous fungal cells and further demonstrates the use of selection/counterselection for the isolation of desired transformants.

*Aspergillus Niger* Protoplast Formation and Transformation

A large volume (500 ml) of protoplasts of a eukaryotic fungal strain of *Aspergillus niger*, ATCC 1015, was generated using a commercially available enzyme mixture which contains beta-glucanase activity as described in Example 1. The protoplasts were isolated from the enzyme mixture by centrifugation and were ultimately re-suspended in a buffer containing calcium chloride by the method described in Example 1.

The protoplasts were aliquoted and frozen at negative 80 degrees Celsius in containers containing a suspension of dimethyl sulfoxide and polyethylene glycol (PEG) as described in Example 1. In some embodiments, the present disclosure teaches that a stock of 96-well microtiter plates containing 25-50 microliters of protoplasts in each well can be prepared and frozen in large batches for large scale genome editing campaigns using this technique.

Traditional PEG Calcium mediated transformations were carried out by automated liquid handlers, which combined the DNA with the protoplast-PEG mixtures in the 96 wells. An additional automated liquid handling step was used to plate the transformation on to selective media after transformation.

Automated Screening of Transformants

As discussed in more detail below, the *A. niger* cells used in this example lacked a functional pyrG gene (i.e., pyrG−) were transformed with a functional pyrG gene, which permitted transformed cells to grow in the absence of Uracil. The pyrG gene of this example was further designed to incorporate into the location of *A. niger*'s wild type met3 gene, thus incorporating a disruption to the naturally occurring met3 gene. Disruption of the met3 gene further results in the transformants being methionine auxotrophs, providing a secondary screening method for identifying transformants.

Transformants grown on the selective media without Uracil were isolated and placed into individual wells of a second microtiter plate. The transformants in the second microtiter plate were allowed to grow (and in some cases sporulate) and for 2-3 days, before being resuspended in a liquid consisting of water and a small amount of detergent to generate a stock (e.g., occasionally a spore stock) suitable for storage and downstream automated screening.

A small aliquot of each of the aforementioned stocks was then used to inoculate liquid media in a third 96 well PCR plate. These small cultures are allowed to grow over night in a stationary incubator so that the yellow-pigment containing spores germinate and form hyphae that are more amenable to selection, and downstream steps.

Following the culturing step, the hyphae of the third PCR plate were lysed by adding a commercially available buffer and heating the cultures to 99 degrees Celsius for 20 minutes. The plates were then centrifuged to separate the DNA suspension supernatant from the cell/organelle pellets. The DNA extractions were then used for PCR analysis to identify cell lines comprising the desired DNA modifications.

Co-Transformation for Integration of SNPs-Design of SNPs

The DNA sequence of the *Aspergillus niger* gene aygA was obtained and the proper reading frame was determined. Four distinct types of mutations were designed, which if integrated would result in a null mutation.

The mutations included a single base pair change that incorporates an in-frame stop codon, a small two base pair deletion, a three-base pair integration, and a larger 100 base pair deletion all of which if properly integrated will eliminate aygA activity. Strains lacking aygA activity have a yellow colored phenotype. The designs were generated as in silico constructs that predicted a set of oligomers that were used to build the constructs using Gibson assembly.

Integration of SNPs by Co-Transformation

Figure 11:
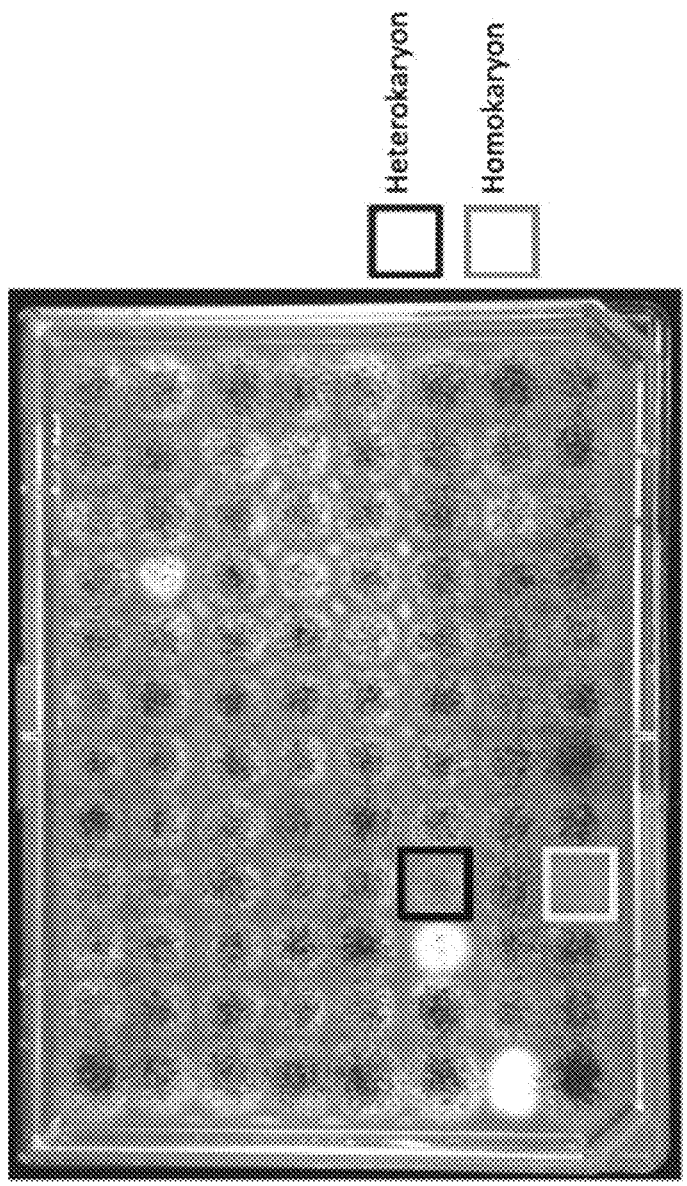
FIG. 11 is an illustration of characterization of heterokaryons/homokaryons according to the disclosure herein. In particular, this figure illustrates screening of *A. niger* mutant strains utilizing the aygA colorimetric gene marker by observing growth of *A. niger* mutant strains on minimal media following automated transformation and screening as described in Example 3. Colonies derived from homokaryotic protoplasts were pure yellow in color and lacked black coloration.
Figure 12:
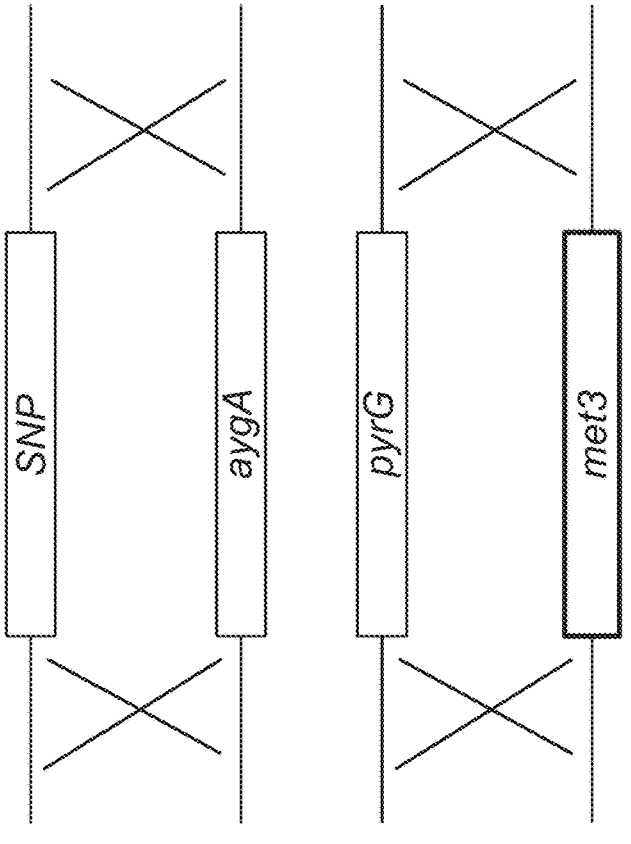
FIG. 12 depicts the results of *A. niger* transformation and validation according to the methods of the present disclosure.
Figure 13:
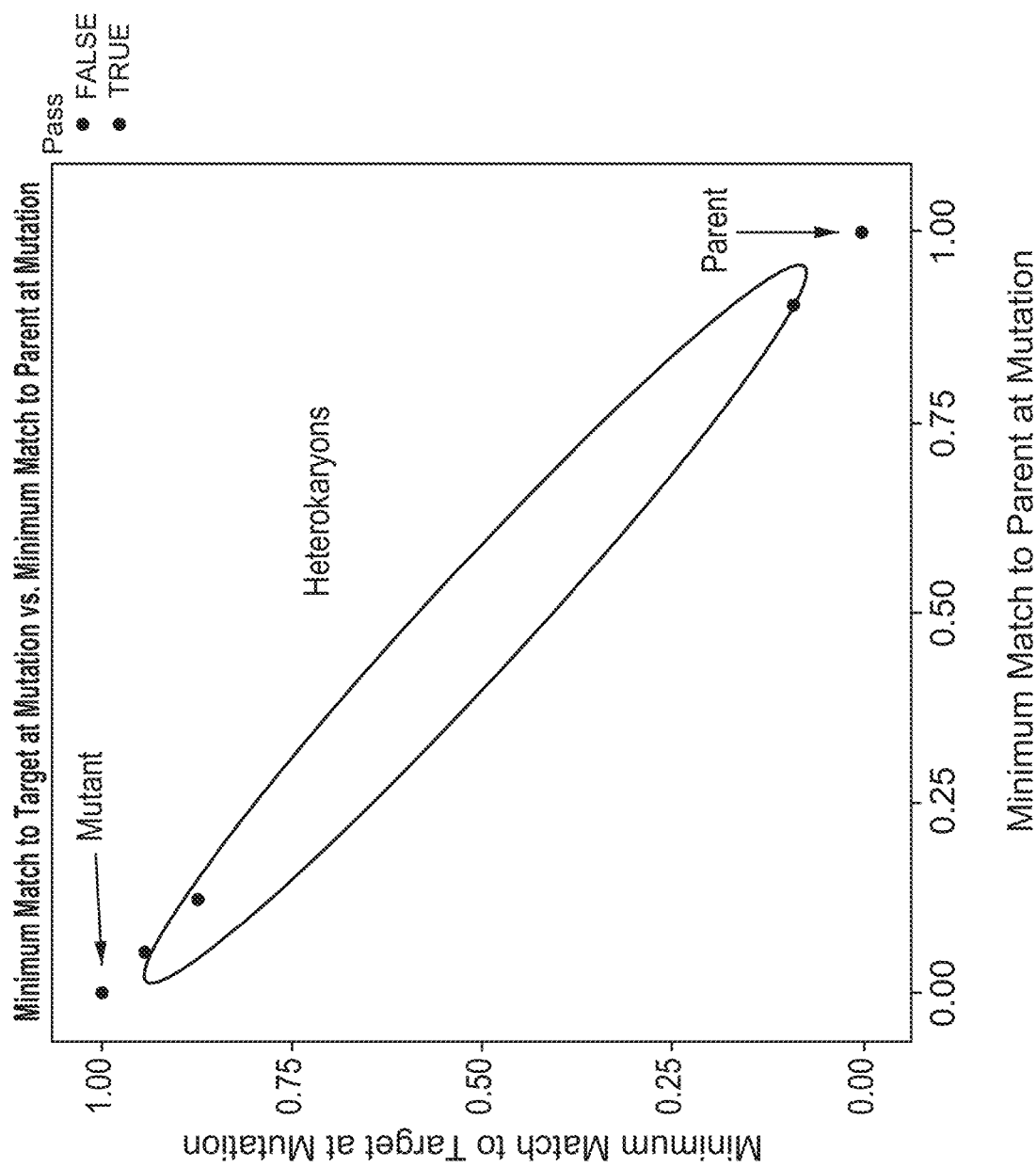
FIG. 13 depicts the results of next generation sequencing of transformed *A. niger* mutants. The X-axis represents the target DNA's sequence identity with the untransformed parent strain. The Y-axis represents the target DNA's sequence identity with the expected mutation. Data points towards the bottom right of the chart exhibit high similarity with the parent strain, and low similarity with the expected transformed sequences. Data points towards the top left of the chart exhibit high similarity to expected transformed sequences and low identity with parent strain. Data points in the middle likely represent heterokaryons with multiple nuclei.

Using the transformation approach described above, amplicons containing the small changes were incorporated into the genome of an *Aspergillus niger* strain 1015. As previously discussed, this strain of *Aspergillus niger* comprised a non-functional pyrG gene, and was therefore unable to grow in the absence of exogenous uracil. Cells that had successfully integrated the pyrG gene were now capable of growth in the absence of uracil. Of these pyrG+ transformants, isolates that also integrated the small mutations in the aygA gene exhibited the yellow colored phenotype. (see FIGS. 11 and 12). The presence of the mutation was also detected through sequencing of small amplicons that contain the region targeted for the SNP exchange (FIG. 13).

Example 5: Purification of Transformed Fungal Strains into Clonal Populations at Scale: Evaluation of Transformation Outputs Many filamentous fungi have a stage in their life cycle in which vegetative growth includes a state in which multiple nuclei are present in individual cells. This has a consequence on the ability to genetically manipulate these organisms. Any genetic changes in one nucleus must be made clonal by purification away from nuclei that do not contain the desired mutation. One method for separating these nuclei is to allow the organism to go through a stage of asexual reproduction in which the resulting spores contain few nuclei, all of the same genotype. By separating individual spores, the strains that are propagated from these spores will contain the desired production traits. Several strains of filamentous fungi that are commercially valuable for production of biomolecules, however, have lost the ability to sporulate or sporulate poorly. This renders the dependence on sporulation for purification of fungal strains problematic. This example describes a method of isolating single transformants, evaluating the transformants for their genotype/phenotype and therefore, the resultant clonal fungal strains, containing targeted mutations with high fidelity and high throughput. The method allows for the rapid generation and purification of improved fungal production strains.

In this method, a transformant suspension can be made from each transformed reaction area which might potentially contain a mixture of homokaryotic or heterokaryotic transformants. The transformant suspension can be diluted to a known degree to obtain individual transformants separated from all of the others through the isolation of this mixture into wells of selection plates to be grown as clonal individuals.

The method set forth herein eliminates the need to use sporulation for the purification of each transformation and facilitates the use of microtiter plates for building strains using liquid media. Petri dishes are large and not compatible with liquid handling automation, therefore limiting to the ability to scale to high throughput. Most importantly, the present method can yield access to clonal transformants in a high-throughput manner whereas existing high-throughput methods known in the art may never necessarily result in a clonal population, even after successive passaging (repeated application of the selection process, which can be very inefficient). In the approach detailed herein, individual clonal strains (and/or heterokaryotic (non-clonal) strains) are placed into separated wells of a microtiter plate for further screening that can facilitate simple integration to high-throughput automation. The method can also facilitate the isolation of single transformants without the need for colony growth on petri dishes such that the entirety of the strain build can occur in a microtiter format.

A fungal strain of interest can produce one or more metabolites, chemicals, or biologics of interest. Transformation protocols call for the transformation of protoplasts with donor DNA. The transformation outputs having transformants are obtained in suspension in liquid media. The suspensions of transformation outputs are diluted by a known quantity such that transformants are, through one-to-many distribution into selection plates, isolated and deposited into a microtiter plate (with several known wells being empty) via the Poisson distribution or optically based upon single cell dispensing.

Upon transformation, the transformation output in each well is examined and evaluated for the presence or absence of a viable transformant and/or for a quantification of total transformant number. The resulting transformation outputs are suspended in liquid media and diluted. The dilution is performed in one of two ways.

In the first type of dilution, the transformation outputs are diluted to a concentration where there is a statistical probability according to a Poisson distribution of only one or no transformant existing in the volume dispensed in a one-to-many manner to selection plates where individual transformants are allowed to grow. The transformants are then dispensed using an ECHO, BIOSPOT, or other liquid handling device, into microtiter plates where they can grow to colonies. Generally this approach may generate many empty wells for each well that contains a single transformant, and ideally very few wells that contain two transformants.

In the second type of dilution, the transformation outputs are diluted to a concentration where they can be optically distinguished as single cells. The concentration can be different depending on the instrument used for dispensing. After optical verification that a single cell exists in a droplet, that droplet is dispensed into a microtiter plate. If multiple transformants, or none, are in the dispensed volume, they can be put into waste collection or re-aspirated. Compared to the Poisson distribution approach (first type of dilution above), it can be expected that each well of the output data will have a single cell in it, with far fewer empty or more than one transformant wells.

Instruments for the second type of dilution can include (1) the CellenONE instrument, which uses microfluidics combined with optics to visually verify that only a single transformant is dispensed into wells of a microtiter plate, where they can grow; (2) the Berkeley Lights Beacon instrument, which operates by flushing cells or transformants into a microchannel, and then uses a laser to push individual cells or transformants into micro-holding pens where they can grown and replicate; (3) a FACS instrument, which uses a microfluidic flow channel to move individual cells past a optical sensor that can detect fluorescence, and can sort cells to output wells based on their fluorescence signal. Unfortunately, currently the only FACS machines on the market are limited to either sorting cells from a single source to multiple destinations or are designed to select from many sources and sort to a single destination. Should a machine be developed that can easily sort cells from many sources to many destinations, it would be appropriate for the high-throughput use case described in this example, with the final requirement that the cells being sorted need to be fluorescently active (either naturally, or through genetic engineering); (4) a Cytena instrument, which operates using similar optical and microfluidic technology as the CellenONE instrument, but it is not compatible with highthroughput/plate-based inputs. It uses a disposable cartridge to hold source liquid, which must be manually bolted to the machine, giving it similar throughput limitations as a FACS machine. The CellenONE can print single transformants with high fidelity.

Example 6: Purification of Transformed Fungal Strains into Clonal Populations at Scale: Evaluation of Transformation Outputs for Varied Parameters of Transformation The methods and systems described herein can be used to perform the evaluation of growth outputs of colonies similar to the description in Example 4 and quantify the number of transformants. In some implementations, the concentration of transformants can be quantified. In some embodiments a total transformant number associated with a transformation output can be quantified. In some instances, one or more parameters of the transformation step can be varied in one or more iterations of the process of strain generation described herein. The total transformant output resulting from each iteration can then be used to examine the effect of the parameter varied in that iteration. FIG. 14 shows an example plot resulting from the evaluation described in example 4 and the quantification described in this example extended to iterative repetitions using varying parameters of total DNA content. The plot in FIG. 14 quantifies the total transformant output, for six different gene loci, resulting from the iterative repetitions using varying amounts of DNA (e.g., 1×, 2×, and 5×) for targeting transformation in each of the unique loci. The transformation outputs obtained from each iterative process were evaluated to determine the relationship between the DNA concentration used and the total transformant output obtained as a result. In the example analysis shown in FIG. 14, the transformation outputs that resulted from reaction inputs having 5×DNA content had higher total transformant output across all the loci A-F analyzed, compared to transformation outputs obtained from reaction inputs having 1× or 2×DNA content.

Example 7: Purification of Transformed Fungal Strains into Clonal Populations at Scale: Evaluation of Growth Outputs for Varied Parameters of Transformation Outputs The methods and systems described herein can be used to perform the evaluation of transformants and resulting growth outputs as described in Example 4 and quantify the number of clonal populations that are of desirable genotype. In some implementations, the fraction of clonal populations that are resultant from a single transformation and the relative fraction of those clonal populations that are homokaryotic can be quantified. In some instances, one or more parameters of the transformation and/or the on-to-many transfer of transformation outputs can be varied in one or more iterations of the process of strain generation described herein. The growth outputs including colonies of populations resulting from each iteration can then be used to examine the effect of the parameter varied in that iteration. An example parameter that can be varied is the degree of dilution of transformation outputs before the one-to-many transfer of discreet volumes to microtiter wells in selection plates.

FIGS. 15A and 15B show example plots of growth outputs obtained from two different dilution procedures used to generate strains of non-sporulating filamentous fungi. The results shown in FIG. 15A was obtained using transformation outputs that were undiluted before conducting a one-to-many transfer to a series of growth areas on selection plates. The results shown in FIG. 15B was obtained using transformation outputs similar to those used for FIG. 15A, but with a known dilution before conducting the one-to-many transfer to a series of growth areas on selection plates. The growth results in FIGS. 15A and 15B can be analyzed by calculating well saturation to indicate a percentage of wells that show growth. Additionally, the results in terms of clonal populations can be analyzed by calculating a percentage of wells resulting in clonal populations.

As shown in FIGS. 15A and 15B, the transformation outputs that were undiluted resulted in 89.4% saturation of the selection plates. Said in another way, the transformation outputs that were undiluted, when transferred to selection plates, resulted in 89.4% of wells in the selection plates having growth. Out of the 89.4% of wells that did show growth 5.9% (e.g., approximately 5 wells out of a set of 86 wells in a 96 well selection plate) were found to be clonal (i.e. edit homokaryon, see FIG. 15A with all nuclei in the multinucleate transformant cell being genetically identical at a locus of interest and/or expressing the gene of interest in the locus of interest). The transformation outputs that were diluted, however, resulted in a 74.4% saturation of the selection plate. That is, the transformation outputs that were diluted by a known amount before discreet volumes were transferred in a one-to-many manner to selection plates, resulted in a 74.4% of wells in the selection plate having growth (e.g., approximately 72 wells out of 96 wells in a selection plate showed growth). Out of the 74.4% of wells that did show growth, 15% (e.g., approximately 11 wells out of the 72 wells showing growth) were found to be clonal (i.e. Edit homokaryon, see FIG. 15B with all nuclei in the multinucleate transformant cell being genetically identical at a locus of interest and/or expressing the gene of interest in the locus of interest). The results shown in the example plots in FIGS. 15A and 15B illustrate the finding that when well saturation was decreased using dilution (other methods such as reducing transforming DNA concentration are also possible) an increase in the percentage of clonal populations in the output (edit homokaryon) to 15% can be observed. Quantification of well saturation (i.e. grow vs no-grow) in a multi-well plate can be analogous to a measurement of density of colonies on a Petri dish. Based on the findings illustrated by the example plots in FIGS. 15A and 15B, if the colonies were too dense, that reduced the likelihood of picking a colony that arose from a single transformation event which, in case of high-throughput methods using multi-well plates, reduces the chance of correctly identifying a clonal (edit homokaryon) strain. If the colonies were made to be less dense (e.g., via dilution), that increased the likelihood of picking a colony that arose from a single transformation event which increased the chance of correctly identifying a clonal (edit homokaryon) strain.

The degree of dilution (or non-dilution) can be determined based on prior knowledge related to the filamentous fungal strain of interest and its properties to undergo homologous recombination. In some filamentous fungi, only a generally low percentage of clean homologous recombination can be possible. In some such instances, transformation may produce mixtures of homo- and heterokaryon strains which renders identifying clonal strain more difficult. That is, if more than one transformant exists per well, the probability of a molecular QC process detecting a clonal strain may decrease. Thus, a greater percentage of transformants that are clonal can be detected and captured (e.g., 15% vs 5.9% of total wells (growth areas) examined) when a system and/or method is implemented to achieve reduced well saturation (74.4% vs ~90%). Said in another way, when a relatively lower saturation was obtained from the high-throughput one-to-many transfer of diluted transformations outputs, the relative number of homokaryotic clonal populations was higher compared to those obtained when using an undiluted version of the same transformation outputs.

In some implementations, the adaptation of the methods for strain generation can be based on iterative testing and evaluation of variations in parameters involved in the high-throughput one-to-many transfers of transformation outputs to generate clonal populations expressing the gene of interest as described herein.

In some embodiments, the systems and methods described herein can be used for HTP strain improvement and/or selection of non-sporulating filamentous fungi utilizing any suitable genetic library (e.g., SNP swap libraries, PRO swap libraries, STOP swap libraries, Start/Stop Codon swap libraries, or combinations of libraries). For example, in some embodiments, the systems and methods described herein can be used for HTP strain improvement of non-sporulating filamentous fungi utilizing two or more types of genetic libraries. For example, in some embodiments, the HTP filamentous fungi strain improvement can be though combining multiple genetic libraries, etc. In some embodiments, the HTP non-sporulating filamentous fungi strain improvement can be carried out by combining use of genetic libraries with one or more traditional strain improvement methods.

In some embodiments, the HTP strain improvement and/or selection of non-sporulating filamentous fungi using systems and/or methods described herein result in an improved filamentous fungal host cell. That is, the present disclosure teaches methods of improving one or more filamentous fungal host cell properties. In some embodiments the improved filamentous fungal host cell property is selected from the group consisting of: volumetric productivity, specific productivity, yield or titre of a product of interest produced by the filamentous fungal host cell. In some embodiments, the improved filamentous fungal host cell property is volumetric productivity. In some embodiments, the improved filamentous fungal host cell property is specific productivity. In some embodiments, the improved filamentous fungal host cell property is yield.

In some embodiments, the HTP non-sporulating filamentous fungal strain improvement methods of the present disclosure result in an filamentous fungal host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one filamentous fungal host cell property over a control filamentous fungal host cell that is not subjected to the HTP strain improvements methods (e.g., an X % improvement in yield or productivity of a biomolecule of interest, incorporating any ranges and subranges therebetween).

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In this disclosure, references to items in the singular should be understood to include items in the plural, and vice versa, unless explicitly stated otherwise or clear from the context. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. The use of any and all examples, or exemplary language ("e.g.," "such as," "including," or the like) provided herein, is intended merely to better illuminate the embodiments and does not pose a limitation on the scope of the embodiments or the claims.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

SEQUENCES OF THE DISCLOSURE WITH SEQ ID NO IDENTIFIERS

| GENE HOMOLOGUES, ORTHOLOGUES OR PARALOGS | | | |
|---|---|---|---|
| NAME | SOURCE | NUCLEIC ACID SEQ ID NO: | COMMENTS |
| manBp | A. niger | 1 | Native promoter of manB gene |
| amyBp | A. oryzae | 2 | Native promoter of amyB gene |
| srpBp | A. niger | 3 | Native promoter of srpB gene |
| mbfAp | A. niger | 4 | Native promoter of mbfA gene |
| pyrG | A. niger | 5 | Native pyrG gene |
| aygA.1 crRNA protospacer sequence | Artificial | 6 | |
| aygA.3 crRNA protospacer sequence | Artificial | 7 | |
| Control crRNA protospacersequence | Artificial | 8 | |
| DJV_03_pyrG_insertion_in_AygA | Artificial | 9 | pyrG with promoter and terminator (lowercase) flanked by 5' and 3' regions of homology (uppercase) to the AygA gene |
| DJV_07_4bp_insertion_in_AygA | Artificial | 10 | 4 bp insertion (lowercase) flanked by 5' and 3' regions of homology (uppercase) to the AygA gene |
| FungiSNP_9 | A. niger | 11 | |
| FungiSNP_12 | A. niger | 12 | |
| FungiSNP_18 | A. niger | 13 | A. niger orthologue of S. cerevisiae SLN1 |
| FungiSNP_40 | A. niger | 14 | |
| Ypd1 orthologue | A. niger | 15 | A. niger orthologue of S. cerevisiae Ypd1 |
| Ssk1 orthologue | A. niger | 16 | A. niger orthologue of S. cerevisiae Ssk1 |
| Skn7 orthologue #1 | A. niger | 17 | A. niger orthologue of S. cerevisiae Skn7 |
| Skn7 orthologue #2 | A. niger | 18 | A. niger orthologue of S. cerevisiae Skn7 |
| Ssk2 orthologue | A. niger | 19 | A. niger orthologue of S. cerevisiae Ssk2 |

Numbered Embodiments of the Disclosure

Other subject matter contemplated by the present disclosure is set out in the following numbered embodiments:

1. A method for isolating clonal transformants from a transformation mixture containing homokaryotic and heterokaryotic transformants, the method comprising:

(a) dispensing a discrete volume of a liquid suspension including a predetermined concentration of a DNA source and a predetermined concentration of a protoplast source to a reaction area in a first substrate including a plurality of reaction areas, the dispensing configured to generate, in each reaction area from the plurality of reaction areas, a transformation output in liquid media subjected to a one-to-many distribution to a series of growth areas such that a percentage of growth areas, from the series of growth areas, that result in a growth that is derived from the transformation output is below a predetermined threshold value;

(b) distributing equal volumes of the transformation output in liquid media from each individual reaction area from the plurality of reaction areas, to the series of growth areas, the series of growth areas being distributed across a plurality of second substrates to spatially separate transformants; and (c) determining, from the series of growth areas, a subset of growth areas that include clonal populations derived from a single transformant.

2. The method of claim 1, wherein the threshold value is approximately 10%, approximately 20%, approximately 30%, approximately 40%, approximately 50%, approximately 60%, approximately 70%, approximately 80%, or approximately 90%.

3. The method of claim 1, wherein the dispensing results in a probability greater than 0.5 that at least 10%, at least 20%, at least 30%, at least 40%, at least 50%, or at least 60% or all of the growth areas that result in growth include no more than a single transformant.

4. The method of claim 3, wherein at least 10%, at least 20%, at least 30%, at least 40%, at least 50%, or at least 60% or all of the growth areas that result in growth include clonal populations that are homokaryotic at a specified locus.

5. The method of claim 1, further comprising:
culturing the growth areas, following the distributing the transformation output in each reaction to the series of growth areas, under predefined conditions for a predefined period of time to allow growth of colonies; and
screening the series of growth areas for the presence or absence of growth that is derived from a single clonal transformant resulting in a clonal population of a desired strain.

6. The method of claim 5, wherein the screening includes optically distinguishing the presence or absence of growth in the plurality of growth areas.

7. The method of claim 1, wherein the cell is a non-sporulating filamentous fungus.

8. The method of claim 1, wherein the cell is of a fungal strain from the phylum Ascomycota or the phylum Basidiomycota.

9. A method for isolating clonal populations derived from single clonal transformants, the method comprising:
(a) dispensing a discrete volume of a liquid suspension including a DNA source and a protoplast to each individual reaction area in a first substrate including a plurality of reaction areas, the dispensing configured to generate, in each reaction area from the plurality of reaction areas, a transformation output in liquid media such that the transformation output when subjected to a one-to-many distribution to a series of growth areas leads to a percentage of growth areas, from the series of growth areas, that result in a growth that is derived from no more than a single transformant, the percentage being at least one of above or below a predefined threshold value;
(b) dispensing, in a high-throughput one-to-many manner, a discrete volume of transformation output in liquid media from each individual reaction area from the plurality of reaction areas, to the series of growth areas distributed across a plurality of second substrates with each second substrate from the plurality of second substrates including a plurality of growth areas mapped to correspond to the plurality of reaction areas included in the first substrate;
(c) culturing growth in each growth area of the series of growth areas distributed across the plurality of second substrates; and
(d) selecting, from the series of growth areas, a subset of growth areas that include clonal populations derived from a single viable clonal transformant.

10. The method of claim 9, wherein the threshold value is chosen based on an efficacy of transformation associated with the transformation output.

11. The method of claim 9, wherein the dispensing results in a probability greater than 0.5 that no more than at most 50%, at most 60%, at most 70%, at most 80%, at most 90%, or at most 95% or all of the individual growth areas include growth derived from a successful transformant.

12. The method of claim 9, further comprising screening, following the culturing growth in each growth area of the series of growth areas, the series of growth areas for the presence or absence of growth that is derived from a single clonal transformant resulting in a clonal population of a desired strain.

13. The method of claim 12, wherein the screening includes optically distinguishing the presence or absence of growth in the plurality of reactions areas.

14. The method of claim 9, wherein the cell is a non-sporulating filamentous fungus.

15. The method of claim 9, wherein the cell is either an Ascomycete or a Basidiomycete.

16. The method of claim 9, further comprising diluting, by a predetermined amount, the transformation output in liquid media from each individual reaction area from the plurality of reaction areas, to generate a diluted transformation output from each individual reaction area from the plurality of reaction areas, the dispensing in a high-throughput one-to-many manner at (b) being the dispensing of the diluted transformation output from each individual reaction area from the plurality of reaction areas.

17. The method of claim 9, wherein the dispensing in a high-throughput, one-to-many manner, the discrete volume of transformation output in liquid media from each individual reaction area from the plurality of reaction areas, is done without any dilution of the discrete volume of transformation output in liquid media.

18. A high-throughput method for engineering a transformant cell, the method comprising:
(a) selecting a set of volumes of liquid suspension including a DNA source sample and a protoplast source associated with the cell, each volume of the liquid suspension from the set of volumes of the liquid suspension being different, by at least one predetermined property, from the remaining volumes of the set of volumes of the liquid suspension;
(b) distributing the set of volumes of the liquid suspension across a plurality of reaction areas, each reaction area from the plurality of reaction areas including a discrete quantity of the liquid suspension;
(c) transforming the quantity of liquid suspension included in each reaction area from the plurality of reaction areas to generate a transformation output from a set of transformation outputs;
(d) distributing the transformation output from the set of transformation outputs in a one-to-many manner to a series of growth areas from a plurality of growth areas; and
(e) evaluating the plurality of growth areas to calculate at least one of (i) a number of growth areas that included a successful transformant, or (ii) a number of growth areas that included growth of a clonal population derived from a single clonal transformant.

19. The method of claim 18, wherein the predetermined property is at least one of a volume of DNA source, a concentration of DNA, a molar ratio of specified DNA ends included in the DNA source sample, or a ratio of concentration of DNA source and concentration of protoplast source.

20. The method of claim 18, wherein the predetermined property is a concentration of DNA chosen from concentrations between 1.00× to 5.00×.

21. The method of claim 18, wherein the predetermined property is a dilution chosen from concentrations between 1×/1 to 1×/10.

22. The method of claim 18, further comprising adjusting a composition of the liquid suspension based on the set of transformation outputs to maximize the number of growth areas that included growth of a clonal population derived from a single clonal transformant.

23. The method of claim 18, further comprising screening the set of growth areas to select the volumes of liquid suspension that resulted in a desired range of number of growth areas that included growth of a clonal population derived from a single clonal transformant.

24. The method of claim 23, wherein the screening includes optically distinguishing the presence or absence of growth in the plurality of growth areas.

25. The method of claim 18, wherein the cell is a non-sporulating filamentous fungus.

26. The method of claim 18, wherein the cell is either an Ascomycete or a Basidiomycete.

27. A high-throughput method for engineering a transformant cell, the method comprising:

(a) dispensing discrete volumes of a liquid suspension, obtained from a reaction area from a plurality of reaction areas in a first substrate, to a series of growth areas from a plurality of series of growth areas distributed across a plurality of second substrates, the plurality of reaction areas including a set of transformants, the dispensing configured to generate a set of growth outputs including colonies derived from the set of transformants; and (b) evaluating the set of growth outputs to calculate at least one of (i) a number of growth outputs that included colonies derived from a successful transformant, or (ii) a number of growth outputs that included colonies derived from a single clonal transformant.

28. A high-throughput method for engineering a transformant cell, the method comprising:

(a) selecting a set of volumes of a liquid suspension including a DNA source and a protoplast source, each volumes of the liquid suspension from the set of volumes of the liquid suspension being different from the remaining volumes of the set of volumes of the liquid suspension;

(b) dispensing a discrete quantity of the liquid suspension to a plurality of reaction areas in a first substrate such that each volume of the liquid suspension from the set of volumes of the liquid suspension is dispensed to an individual reaction area in the first substrate including the plurality of reaction areas;

(c) transforming the quantity of liquid suspension in each reaction area from the plurality of reaction areas to generate a transformation output from a set of transformation outputs;

(d) distributing equal quantities of each transformation output from the set of transformation outputs from each individual reaction area from the plurality of reaction areas, to a series of growth areas from a plurality of series of growth areas distributed across a plurality of second substrates, to generate a set of growth outputs including colonies derived from the set of transformation outputs; and (d) evaluating the set of growth outputs to calculate at least one of (i) a number of transformation outputs that included a growth output derived from a successful transformant, or (ii) a number of transformation outputs that resulted in growth output derived from a single clonal transformant.

29. A system for high-throughput engineering of a cell, the system comprising:

a memory including a set of instructions;

a processor coupled to the memory and configured to execute the set of instructions, the set of instructions including instructions to:

select a set of volumes of a reaction mixture in liquid media, the reaction mixture including a DNA source and a protoplast source, and each volume of the reaction mixture from the set of volumes of the reaction mixture being selected to be used to generate a transformant output from a set of transformant outputs;

receive data associated with the set of transformant outputs generated using the set of dilutions of the reaction mixture in liquid media;

receive data associated with a set of growth outputs generated using the set of transformation outputs, each transformation output from the set of transformation outputs being used to generate a series of growth outputs from a plurality of series of growth outputs in a one-to-many manner; and calculate a measure of rate of transformation based on at least one of the data associated with the set of transformant outputs or the data associated with a set of growth outputs.

30. The system of claim 29, the processor being further configured to:

determine, based on the measure of rate of transformation, a desired concentration of the reaction mixture to be used for engineering the cell.

31. A system for high-throughput liquid handling, the system comprising:

a pipetting unit including a pipettor including a shaft and a pipetting end extending from a distal end of the pipettor shaft;

a motor unit coupled to the pipetting unit and configured to:

actuate the pipetting unit over a predefined path, releasably engage the pipetting end with a tip configured to hold a discreet amount of a liquid suspension including a predetermined concentration of at least one of a DNA source, a protoplast, and a transformation output, transfer, when the pipetting end is engaged with the tip and when the pipetting unit is transitioned from a first configuration to a second configuration, the discreet amount of liquid suspension from a source of the liquid suspension to the tip, and transfer, when the pipetting end is engaged with the tip and when the pipetting unit is transitioned from the second configuration to the first configuration, the discreet amount of liquid suspension from the tip to a destination of the mixture; and an electronics unit, operatively coupled to the pipetting unit and the motor unit, the electronics unit configured to control the motor unit.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

The invention claimed is:

1. A method for isolating clonal transformants from a transformation mixture containing homokaryotic and heterokaryotic transformants, the method comprising:

(a) dispensing a discrete volume of a liquid suspension including a predetermined concentration of a DNA source, the DNA source being foreign DNA prepared by assembling DNA fragments, and a predetermined concentration of a protoplast source, the protoplast source being fungal cells, to a reaction area in a first substrate including a plurality of reaction areas, the dispensing configured to generate, in each reaction area from the plurality of reaction areas, a transformation output in liquid media subject to a one-to-many distribution to a series of liquid growth areas such that a percentage of liquid growth areas, from the series of liquid growth areas, that result in a growth that is derived from the transformation output, is below a predetermined threshold value;
(b) distributing equal volumes of the transformation output in liquid media from each individual reaction area from the plurality of reaction areas, to the series of liquid growth areas, the series of liquid growth areas being distributed across a plurality of second substrates to spatially separate transformants; and
(c) determining, from the series of liquid growth areas, a subset of liquid growth areas that include clonal populations derived from a single transformant.

2. The method of claim 1, wherein the threshold value is approximately 10%, approximately 20%, approximately 30%, approximately 40%, approximately 50%, approximately 60%, approximately 70%, approximately 80%, or approximately 90%.

3. The method of claim 1, wherein the dispensing results in a probability greater than 0.5 that at least 10%, at least 20%, at least 30%, at least 40%, at least 50%, at least 60% or all of the liquid growth areas that result in growth include no more than a single transformant.

4. The method of claim 3, wherein at least 10%, at least 20%, at least 30%, at least 40%, at least 50%, or at least 60% or all of the liquid growth areas that result in growth include clonal populations that are homokaryotic at a specified locus.

5. The method of claim 1, further comprising:
culturing the liquid growth areas, following the distributing the transformation output in each reaction to the series of liquid growth areas, under predefined conditions for a predefined period of time to allow growth of colonies; and
screening the series of liquid growth areas for the presence or absence of growth that is derived from a single clonal transformant resulting in a clonal population of a desired strain.

6. The method of claim 5, wherein the screening includes optically distinguishing the presence or absence of growth in the plurality of liquid growth areas.

7. The method of claim 1, wherein the fungal cells in the protoplast source are from a non-sporulating filamentous fungus.

8. The method of claim 1, wherein the fungal cells in the protoplast source are from a fungal strain from the phylum Ascomycota.

9. The method of claim 1, wherein the determining the subset of liquid growth areas includes identifying one or more liquid growth areas that include clonal populations derived from a single transformant that is homokaryotic.

10. A method for isolating clonal populations derived from single clonal transformants, the method comprising:
(a) dispensing a discrete volume of a liquid suspension including a DNA source, the DNA source being foreign DNA prepared by assembling DNA fragments, and a protoplast source, the protoplast source being fungal cells, to each individual reaction area in a first substrate including a plurality of reaction areas, the dispensing configured to generate, in each reaction area from the plurality of reaction areas, a transformation output in liquid media such that the transformation output when subject to a one-to-many distribution to a series of liquid growth areas leads to a percentage of liquid growth areas, from the series of liquid growth areas, that result in a growth that is derived from no more than a single transformant, the percentage being at least one of above or below a predefined threshold value;
(b) dispensing, in a high-throughput one-to-many manner, a discrete volume of transformation output in liquid media from each individual reaction area from the plurality of reaction areas, to the series of liquid growth areas distributed across a plurality of second substrates with each second substrate from the plurality of second substrates including a plurality of liquid growth areas mapped to correspond to the plurality of reaction areas included in the first substrate;
(c) culturing growth in each liquid growth area of the series of liquid growth areas distributed across the plurality of second substrates; and
(d) selecting, from the series of liquid growth areas, a subset of liquid growth areas that include clonal populations derived from a single viable clonal transformant.

11. The method of claim 10, wherein the threshold value is chosen based on an efficacy of transformation associated with the transformation output.

12. The method of claim 10, wherein the dispensing results in a probability greater than 0.5 that no more than at most 50%, at most 60%, at most 70%, at most 80%, at most 90%, or at most 95% or all of the individual liquid growth areas include growth derived from a successful transformant.

13. The method of claim 10, further comprising screening, following the culturing growth in each liquid growth area of the series liquid growth areas, the series of liquid growth areas for the presence or absence of growth that is derived from a single clonal transformant resulting in a clonal population of a desired strain.

14. The method of claim 13, wherein the screening includes optically distinguishing the presence or absence of growth in the plurality of reactions areas.

15. The method of claim 10, wherein the fungal cells in the protoplast source are from a non-sporulating filamentous fungus.

16. The method of claim 10, wherein the fungal cells in the protoplast source are from an Ascomycete.

17. The method of claim 10, further comprising:
diluting, by a predetermined amount, the transformation output in liquid media from each individual reaction area from the plurality of reaction areas, to generate a diluted transformation output from each individual reaction area from the plurality of reaction areas, the dispensing in a high-throughput one-to-many manner at (b) being the dispensing of the diluted transformation output from each individual reaction area from the plurality of reaction areas.

18. The method of claim 10, wherein the dispensing in a high-throughput, one-to-many manner, the discrete volume of transformation output in liquid media from each individual reaction area from the plurality of reaction areas, is done without any dilution of the discrete volume of transformation output in liquid media.

19. A high-throughput method for engineering a transformant cell, the method comprising:
(a) selecting a set of volumes of liquid suspension including a DNA source sample, the DNA source sample including foreign DNA prepared by assembling DNA fragments, and a protoplast source associated with the cell, the protoplast source being fungal cells, each volume of the liquid suspension from the set of volumes of the liquid suspension being different, by at least one predetermined property, from the remaining volumes of the set of volumes of the liquid suspension;
(b) distributing the set of volumes of the liquid suspension across a plurality of reaction areas, each reaction area from the plurality of reaction areas including a discrete quantity of the liquid suspension;
(c) transforming the quantity of liquid suspension included in each reaction area from the plurality of reaction areas to generate a transformation output from a set of transformation outputs;
(d) distributing the transformation output from the set of transformation outputs in a one-to-many manner to a series of liquid growth areas from a plurality of liquid growth areas; and
(e) evaluating the plurality of liquid growth areas to calculate at least one of (i) a number of liquid growth areas that included a successful transformant, or (ii) a number of liquid growth areas that included growth of a clonal population derived from a single clonal transformant.

20. The method of claim 19, wherein the predetermined property is a concentration of DNA.

21. The method of claim 19, wherein the predetermined property is a concentration of DNA, with each volume of the liquid suspension from the set of volumes of the liquid suspension having a concentration of DNA chosen from concentrations between 1.00× to 5.00×.

22. The method of claim 19, wherein the predetermined property is a concentration of DNA based on a dilution of the DNA source sample, with each volume of the liquid suspension from the set of volumes of the liquid suspension having a dilution chosen from concentrations between 1×/1 to 1×/10.

23. The method of claim 19, further comprising adjusting a composition of the liquid suspension based on the set of transformation outputs to maximize the number of liquid growth areas that included growth of a clonal population derived from a single clonal transformant.

24. The method of claim 19, further comprising screening the set of liquid growth areas to select the volumes of liquid suspension that resulted in a desired range of number of liquid growth areas that included growth of a clonal population derived from a single clonal transformant.

25. The method of claim 24, wherein the screening includes optically distinguishing the presence or absence of growth in the plurality of liquid growth areas.

26. The method of claim 19, wherein the fungal cells in the protoplast source are from a non-sporulating filamentous fungus.

27. The method of claim 19, wherein the fungal cells in the protoplast source are from an Ascomycete.

28. The method of claim 19, further comprising: calculating a measure of rate of transformation associated with each transformation output from the set of transformation outputs based on the number of liquid growth areas that included a successful transformant.

29. The method of claim 19, further comprising: identifying a subset of the transformation outputs from the set of transformation outputs, such that each transformation output from the subset of the transformation outputs, when distributed to a series of liquid growth areas, resulted in a proportion of liquid growth areas that included growth of a clonal population derived from a single clonal transformant, the proportion being greater than a threshold value.

30. The method of claim 19, further comprising:
determining a subset of the transformation outputs from the set of transformation outputs, such that each transformation output from the subset of the transformation, when distributed to a series of liquid growth areas, resulted in
(i) a first proportion of growth areas that included a successful transformant, the first proportion being greater than a first threshold value;
(ii) (ii) a second proportion of liquid growth areas that included growth of a clonal population derived from a single clonal transformant, the second proportion being greater than a second threshold value;
identifying a subset of volumes of liquid suspension including the DNA source sample from the set of volumes of liquid suspension including a DNA source sample to be suitable for high-throughput engineering of the transformant cell.

* * * * *

UNITED STATES PATENT AND TRADEMARK OFFICE
CERTIFICATE OF CORRECTION

PATENT NO. : 11,479,779 B2
APPLICATION NO. : 17/387634
DATED : October 25, 2022
INVENTOR(S) : Benjamin Knox et al.

It is certified that error appears in the above-identified patent and that said Letters Patent is hereby corrected as shown below:

In the Claims

At Column 90, Claim number 13, Line number 32:
"the series liquid growth areas, the series of liquid growth"
Should read:
-- the series of liquid growth areas, the series of liquid growth --

At Column 92, Claim number 30, Line number 30:
"(i) a first proportion of growth areas that included a"
Should read:
-- (i) a first proportion of liquid growth areas that included a --

At Column 92, Claim number 30, Line number 36:
"greater than a second threshold value;"
Should read:
-- greater than a second threshold value; and --

Signed and Sealed this
Third Day of January, 2023

Katherine Kelly Vidal
*Director of the United States Patent and Trademark Office*